US012698342B2

(12) United States Patent
Jikoh et al.

(10) Patent No.: US 12,698,342 B2
(45) Date of Patent: Aug. 4, 2026

(54) THERAPY FOR DRUG-RESISTANT CANCER BY ADMINISTRATION OF ANTI-HER2 ANTIBODY/DRUG CONJUGATE

(71) Applicant: DAIICHI SANKYO COMPANY, LIMITED, Tokyo (JP)

(72) Inventors: Takahiro Jikoh, Tokyo (JP); Yusuke Ogitani, Tokyo (JP); Kazutaka Yoshihara, Tokyo (JP); Seiko Endo, Tokyo (JP); Yoshihiko Fujisaki, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 158 days.

(21) Appl. No.: 16/334,008

(22) PCT Filed: Oct. 5, 2017

(86) PCT No.: PCT/JP2017/036215
§ 371 (c)(1),
(2) Date: Mar. 16, 2019

(87) PCT Pub. No.: WO2018/066626
PCT Pub. Date: Apr. 12, 2018

(65) Prior Publication Data

US 2019/0330368 A1 Oct. 31, 2019

(30) Foreign Application Priority Data

Oct. 7, 2016 (JP) ................................ 2016-199341
May 16, 2017 (JP) ................................ 2017-097589
Sep. 8, 2017 (JP) ................................ 2017-172814

(51) Int. Cl.

| | |
|---|---|
| ***C07K 16/32*** | (2006.01) |
| ***A61K 31/4015*** | (2006.01) |
| ***A61K 31/4741*** | (2006.01) |
| ***A61K 47/68*** | (2017.01) |
| ***A61P 35/00*** | (2006.01) |

(52) U.S. Cl.
CPC .......... *C07K 16/32* (2013.01); *A61K 31/4015* (2013.01); *A61K 31/4741* (2013.01); *A61K 47/68037* (2023.08); *A61P 35/00* (2018.01)

(58) Field of Classification Search
CPC .......... A61K 47/6803; A61K 2039/505; A61K 2039/545; A61K 47/6851; A61K 47/6855; A61P 35/00
See application file for complete search history.

(56) References Cited

U.S. PATENT DOCUMENTS

| | | | | |
|---|---|---|---|---|
| 5,677,171 | A | 10/1997 | Hudziak et al. | |
| 5,821,337 | A | 10/1998 | Carter et al. | |
| 5,834,476 | A | 11/1998 | Terasawa et al. | |
| 5,837,673 | A | 11/1998 | Tsujihara et al. | |
| 5,892,043 | A | 4/1999 | Tsujihara et al. | |
| 6,214,345 | B1 | 4/2001 | Firestone et al. | |
| 6,291,671 | B1 | 9/2001 | Inoue et al. | |
| 6,835,807 | B1 | 12/2004 | Susaki et al. | |
| 7,585,491 | B2 | 9/2009 | Govindan | |
| 7,837,980 | B2 | 11/2010 | Alley et al. | |
| 8,591,897 | B2 * | 11/2013 | Bryant | G16H 20/10 424/174.1 |
| 8,609,095 | B2 * | 12/2013 | Pedersen | A61K 39/395 424/174.1 |
| 8,802,820 | B2 | 8/2014 | Chamberlain et al. | |
| 10,155,821 | B2 * | 12/2018 | Naito | A61K 47/6869 |
| 11,795,236 | B2 * | 10/2023 | Naito | C07D 491/22 |
| 2003/0148931 | A1 | 8/2003 | Takahashi et al. | |
| 2003/0166513 | A1 | 9/2003 | Imura et al. | |
| 2004/0185053 | A1 | 9/2004 | Govindan | |
| 2005/0123536 | A1 | 6/2005 | Law et al. | |
| 2005/0276812 | A1 | 12/2005 | Ebens et al. | |
| 2006/0018899 | A1 | 1/2006 | Kao et al. | |
| 2006/0193865 | A1 | 8/2006 | Govindan | |
| 2007/0071764 | A1 | 3/2007 | Sullivan et al. | |
| 2008/0050310 | A1 | 2/2008 | Ebens, Jr. et al. | |
| 2008/0131363 | A1 | 6/2008 | Govindan et al. | |
| 2008/0161245 | A1 | 7/2008 | Kratz et al. | |
| 2008/0305044 | A1 | 12/2008 | McDonagh et al. | |
| 2009/0274713 | A1 | 11/2009 | Chari et al. | |
| 2009/0286258 | A1 | 11/2009 | Kaur et al. | |
| 2011/0059076 | A1 | 3/2011 | Mcdonagh et al. | |

(Continued)

FOREIGN PATENT DOCUMENTS

| | | | |
|---|---|---|---|
| CA | 2927832 | A1 | 11/2011 |
| CA | 2859255 | A1 | 6/2013 |

(Continued)

OTHER PUBLICATIONS

Ogitani et al Clin. Cancer Res. vol. 22 p. 5097 (Mar. 2016). (Year: 2016).*

(Continued)

*Primary Examiner* — Julie Wu
(74) *Attorney, Agent, or Firm* — Foley & Lardner LLP

(57) ABSTRACT

As treatment effective for HER2-expressing cancer having resistance or refractoriness to an existing anti-HER2 drug, there are provided a therapeutic agent and a treatment method using an antibody-drug conjugate in which a linker and a drug represented by the formula: -(Succinimid-3-yl-N)—$CH_2CH_2CH_2CH_2CH_2$—C(=O)-GGFG (SEQ ID NO: 5) —NH—$CH_2$—O—$CH_2$—C(=O)—(NH-DX) are conjugated to an anti-HER2 antibody.

32 Claims, 14 Drawing Sheets

Specification includes a Sequence Listing.

(56) References Cited

U.S. PATENT DOCUMENTS

| | | | |
|---|---|---|---|
| 2011/0070248 A1 | 3/2011 | Ichikawa et al. |
| 2011/0293513 A1 | 12/2011 | Govindan et al. |
| 2012/0121615 A1 | 5/2012 | Flygare et al. |
| 2012/0171201 A1 | 7/2012 | Sapra |
| 2012/0201809 A1 | 8/2012 | Bhat et al. |
| 2013/0123178 A1 | 5/2013 | Dimarchi et al. |
| 2015/0297748 A1 | 10/2015 | Masuda et al. |
| 2015/0352224 A1 | 12/2015 | Naito et al. |
| 2016/0287722 A1 | 10/2016 | Govindan |

FOREIGN PATENT DOCUMENTS

| | | |
|---|---|---|
| CN | 101023100 A | 8/2007 |
| CN | 101490087 A | 7/2009 |
| CN | 102481364 A | 5/2012 |
| EP | 0 495 432 A1 | 7/1992 |
| EP | 0 737 686 A1 | 10/1996 |
| EP | 0 916 348 A1 | 5/1999 |
| EP | 1 155 702 A1 | 11/2001 |
| EP | 2 907 824 A1 | 8/2015 |
| EP | 2 910 573 A1 | 8/2016 |
| JP | H05-059061 A | 3/1993 |
| JP | H08-337584 A | 12/1996 |
| JP | H10-095802 A | 4/1998 |
| JP | H1171280 A | 3/1999 |
| JP | H11-092405 A | 4/1999 |
| JP | 2002-060351 A | 2/2002 |
| JP | 2005-511627 A | 4/2005 |
| JP | 2006-511526 A | 4/2006 |
| JP | 2008-521828 A | 6/2008 |
| JP | 2009-538629 A | 11/2009 |
| JP | 2011-519864 A | 7/2011 |
| JP | 2011-524001 A | 8/2011 |
| JP | 2012-509259 A | 4/2012 |
| JP | 2012-100671 A | 5/2012 |
| JP | 2013-500253 A | 1/2013 |
| JP | 2013-534535 A | 9/2013 |
| JP | 2013-534906 A | 9/2013 |
| KR | 1020010052385 A | 6/2001 |
| KR | 1020110044808 A | 4/2011 |
| RU | 2404810 C2 | 7/2008 |
| TW | I232930 | 5/2005 |
| TW | 200817434 A | 4/2008 |
| WO | WO-97/46260 A1 | 12/1997 |
| WO | WO-00/25825 A1 | 5/2000 |
| WO | WO-01/00244 A2 | 1/2001 |
| WO | WO-02/00734 A1 | 1/2002 |
| WO | WO 03/043583 A2 | 5/2003 |
| WO | WO-2005/112919 A2 | 12/2005 |
| WO | WO 2006/065533 A2 | 6/2006 |
| WO | WO 2006/092230 A2 | 9/2006 |
| WO | WO-2011/011474 A1 | 1/2011 |
| WO | WO-2011/068845 A1 | 6/2011 |
| WO | WO 2013/163229 A1 | 10/2013 |
| WO | WO 2013/188740 A1 | 12/2013 |
| WO | WO-2014/057687 A1 | 4/2014 |
| WO | WO-2014/061277 A1 | 4/2014 |
| WO | WO-2014/107024 A1 | 7/2014 |
| WO | WO-2015/115091 A1 | 8/2015 |

OTHER PUBLICATIONS

NCT02564900, 13 pages (Year: 2015).*

Carceller Drugs of Today vol. 51(11) p. 669 (Nov. 2015), (Year: 2015).*

Russian Office Action dated Mar. 5, 2019 in corresponding application No. 2016143351.

Sievers et al, Antibody-Drug Conjugates in Cancer Therapy, Annual Review of Medicine, 2013, vol. 64, No. 1, pp. 15-29.

United States Office Action dated Apr. 5, 2019 in U.S. Appl. No. 15/821,697.

International Searching Authority, "International Search Report," issued in connection with International Patent Application No. PCT/JP2017/036215, dated Nov. 21, 2017.

International Searching Authority, "Written Opinion," issued in connection with International Patent Application No. PCT/JP2017/036215, dated Nov. 21, 2017.

Adams et al., "Humanization of a recombinant monoclonal antibody to produce a therapeutic HER dimerization inhibitor, pertuzumab," Cancer Immunol. Immunother., vol. 55, 2006, pp. 717-727.

Alley et al., "Antibody-drug conjugates: targeted drug delivery for cancer," Current Opinion in Chemical Biology, vol. 14, 2010, pp. 529-537.

Barginear et al., "Trastuzumab-DM1: A Review of the Novel Immuno-Conjugate for HER2-Overexpressing Breast Cancer," The Open Breast Cancer Journal, vol. 1, 2009, pp. 25-30.

Barok et al., "Trastuzumab-DM1 is highly effective in preclinical models of HER2-positive gastric cancer," Cancer Letters, vol. 306, 2011, pp. 172-179.

Baselga et al., "Phase II Study of Weekly Intravenous Recombinant Humanized Anti-p185$^{HER2}$ Monoclonal Antibody in Patients with HER2/*neu*-Overexpressing Metastatic Breast Cancer," Journal of Clinical Oncology, vol. 14, No. 3, Mar. 1996, pp. 737-744.

Beck, Alain, "The Next Generation of Antibody-drug Conjugates Comes of Age," Discovery Medicine, vol. 10, No. 53, Oct. 16, 2010 (8 pages).

Behrens et al., "Methods for site-specific drug conjugation to antibodies," mAbs, vol. 6, No. 1, 2014, pp. 46-53.

Burke et al., "Design, Synthesis, and Biological Evaluation of Antibody-Drug Conjugates Comprised of Potent Camptothecin Analogues", Bioconjugate Chemistry, vol. 20, No. 6, 2009, pp. 1242-1250.

Burris, III et al., "Phase II Study of the Antibody Drug Conjugate Trastuzumab-DM1 for the Treatment of Human Epidermal Growth Factor Receptor 2 (HER2)-Positive Breast Cancer After Prior HER2-Directed Therapy," Journal of Clinical Oncology, vol. 29, No. 4, Feb. 1, 2011, pp. 398-405.

Cardillo et al., "Humanized Anti-Trop-2 IgG-SN-38 Conjugate for Effective Treatment of Diverse Epithelial Cancers: Preclinical Studies in Human Cancer Xenograft Models and Monkeys," Clinical Cancer Research, vol. 17, No. 10, Mar. 3, 2011, pp. 3157-3169.

Coussens et al., "Tyrosine Kinase Receptor with Extensive Homology to EGF Receptor Shares Chromosomal Location with *neu* Oncogene," Science, vol. 230, Dec. 1985, pp. 1132-1139.

Damle, Nitin K., "Tumour-targeted chemotherapy with immunoconjugates of calicheamicin," Expert Opinion Biol. Ther., vol. 4, No. 9, 2004, pp. 1445-1452.

De Jager et al., "DX-8951f: Summary of Phase I Clinical Trials," Ann. N.Y. Acad. Sci., vol. 922, 2000, pp. 260-273.

Di Fiore et al., "*erb*B-2 Is a Potent Oncogene When Overexpressed in NIH/3T3 Cells," Science, vol. 237, Jul. 1987, pp. 178-182.

Ducry et al., "Antibody-Drug Conjugates: Linking Cytotoxic Payloads to Monoclonal Antibodies," Bioconjugate Chem., vol. 21, No. 1, 2010, pp. 5-13.

Esteva et al., "A Phase II Study of Intravenous Exatecan Mesylate (DX-8951f) Administered Daily for 5 Days Every 3 Weeks to Patients with Metastatic Breast Carcinoma," American Cancer Society, 2003, 900-907.

Fendly et al., "Characterization of Murine Monoclonal Antibodies Reactive to Either the Human Epidermal Growth Factor Receptor or HER2/*neu* Gene Product," Cancer Research, vol. 50, Mar. 1, 1990, pp. 1550-1558.

Fukushige et al., "Localization of a Novel v-*erb*B-Related Gene, c-*erb*B-2, on Human Chromosome 17 and Its Amplification in a Gastric Cancer Cell Line," Molecular and Cellular Biology, vol. 6, No. 3, Mar. 1986, pp. 955-958.

Graus-Porta et al., "ERbB-2, the preferred heterodimerization partner of all ErbB receptors, is a mediator of lateral signaling," The EMBO Journal, vol. 16, No. 7, 1997, pp. 1647-1655.

Gravalos et al., "HER2 in gastric cancer: a new prognostic factor and a novel therapeutic target," Annals of Oncology, vol. 19, 2008, pp. 1523-1529.

Hardwick et al., "Immunohistochemical detection of p53 and *c-erb*B-2 in oesophageal carcinoma; no correlation with prognosis," European Journal of Surgical Oncology, vol. 23, 1997, pp. 30-35.

(56) References Cited

OTHER PUBLICATIONS

Hudis, M.D., Clifford A., "Trastuzumab—Mechanism of Action and Use in Clinical Practice," The New England Journal of Medicine, vol. 357, No. 1, 2007, pp. 39-51.
Hudziak et al., "Increased expression of the putative growth factor receptor p185$^{HER2}$ causes transformation and tumorigenesis of NIH 3T3 cells," Proc. Natl. Acad. Sci. USA, vol. 84, Oct. 1987, pp. 7159-7163.
Inoue et al., "CM-Dextran-Polyalcohol-Camptothecin Conjugate: DE-310 with a Novel Carrier System and Its Preclinical Data," Polymer Drugs in the Clinical Stage, 2003, pp. 145-153.
Joto et al., "DX-8951F, A Water-Soluble Camptothecin Analog, Exhibits Potent Antitumor Activity Against a Human Lung Cancer Cell Line and its SN-38-Resistant Variant," Int. J. Cancer, vol. 72, 1997, pp. 680-686.
Kaptain et al., "Her-2/*neu* and Breast Cancer," Diagnostic Molecular Pathology, vol. 10, No. 3, 2001, pp. 139-152.
Karunagaran et al., "ErbB-2 is a common auxiliary subunit of NDF and EGF receptors: implications for breast cancer," The EMBO Journal, vol. 15, No. 2, 1996, pp. 254-264.
Korkaya et al., "HER2 regulates the mammary stem/progenitor cell population driving tumorigenesis and invasion," Oncogene, vol. 27, 2008, pp. 6120-6130.
Kumazawa et al., "Antitumor activity of DX-8951f: a new camptothecin derivative," Expert Opinion Invest. Drugs vol. 7, No. 4, 1998, pp. 625-632.
Kumazawa et al., "DE-310, a novel macromolecular carrier system for the camptothecin analog DX-8951f: Potent antitumor activities in various murine tumor models," Cancer Sci., vol. 95, No. 2, Feb. 2004, pp. 168-175.
Kumazawa et al., "Potent and broad antitumor effects of DX-8951f, a water-soluble camptothecin derivative, against various human tumors xenografted in nude mice," Cancer Chemother. Pharmacol., vol. 42, 1998, pp. 210-220.
Loganzo et al., "Tumor Cells Chronically Treated with a Trastuzumab-Maytansinoid Antibody-Drug Conjugate Develop Varied Resistance Mechanisms but Respond to Alternate Treatments," Molecular Cancer Therapeutics, vol. 14, No. 4, Apr. 2015, pp. 952-963.
Masubuchi, N., "Pharmacokinetics of DE-310, a novel macromolecular carrier system for the camptothecin analog DX-8951f, in tumor-bearing mice," Pharmazie, vol. 59, No. 5, 2004, pp. 374-377.
Mitsui et al., "A New Water-soluble Camptothecin Derivative, DX-8951f, Exhibits Potent Antitumor Activity against Human Tumors in vitro and in vivo," Jpn. J. Cancer Res, vol. 86, Aug. 1995, pp. 776-782.
Nakada et al., "Novel antibody drug conjugates containing exatecan derivative-based cytotoxic payloads," Bioorganic & Medicinal Chemistry Letters, vol. 26, 2016, pp. 1542-1545.
Ochi et al., "A possible mechanism for the long-lasting antitumor effect of the macromolecular conjugate DE-310: mediation by cellular uptake and drug release of its active camptothecin analog DX-8951," Cancer Chemother Pharmacol, vol. 55, 2005, pp. 323-332.
Ogitani et al., "DS-8201a, A Novel HER2-Targeting ADC with a Novel DNA Topoisomerase I Inhibitor, Demonstrates a Promising Antitumor Efficacy with Differentiation from T-DM1," Clinical Cancer Research, vol. 22, No. 20, Oct. 15, 2016, pp. 5097-5108.
Oguma et al., "Validation study of a method for assaying DE-310, a macromolecular carrier conjugate containing an anti-tumor camptothecin derivative, and the free drug in tumor tissue by high performance liquid chromatography/atmospheric pressure chemical ionization tandem mass spectrometry," Biomedical Chromatography, vol. 19, 2005, pp. 19-26.
Senter et al., "The discovery and development of brentuximab vedotin for use in relapsed Hodgkin lymphoma and systemic anaplastic large cell lymphoma," Nature Biotechnology, vol. 30, No. 7, Jul. 2012, pp. 631-637.
Shen et al., "Conjugation site modulates the in vivo stability and therapeutic activity of antibody-drug conjugates," Nature Biotechnology, vol. 30, Jan. 22, 2012, pp. 184-189.
Shiose et al., "Systematic Research of Peptide Spacers Controlling Drug Release from Macromolecular Prodrug System, Carboxymethyldextran Polyalcohol-Peptide-Drug Conjugates," Bioconjugate Chem., vol. 20, 2009, pp. 60-70.
Slamon et al., "Human Breast Cancer: Correlation of Relapse and Survival with Amplification of the HER-2/*neu* Oncogene," Science, vol. 235, Jan. 9, 1987, pp. 177-182.
Slamon et al., "Studies of the HER-2/*neu* Proto-oncogene in Human Breast and Ovarian Cancer," Science, vol. 244, May 12, 1989, pp. 707-712.
Sliwkowski et al., "Coexpression of *erb*B2 and *erb*B3 Proteins Reconstitutes a High Affinity Receptor for Heregulin." The Journal of Biological Chemistry, vol. 269, No. 20, 1994, pp. 14661-14665.
Sliwkowski et al., "Nonclinical Studies Addressing the Mechanism of Action of Trastuzumab (Herceptin)," Seminars in Oncology, vol. 26, No. 4, Suppl. 12, Aug. 1999, No. 60-70.
Soepenberg et al., "Liquid chromatographic assays for DE-310, a novel camptothecin analog, and two major enzymatic products in human matrices," Journal of Chromatography B, vol. 799, 2004, pp. 15-22.
Soepenberg et al., "Phase I and Pharmacokinetic Study of DE-310 in Patients with Advanced Solid Tumors," Clinical Cancer Research, vol. 11, Jan. 15, 2005, pp. 703-711.
Takegawa et al., "DS-8201a, a new HER2-targeting antibody-drug conjugate incorporating a novel DNA topoisomerase I inhibitor, overcomes HER2-positive gastric cancer T-DM1 resistance," International Journey of Cancer, vol. 141, 2017, pp. 1682-1689.
Takiguchi et al., "Antitumor Effect of DX-8951, a Novel Camptothecin Analog, on Human Pancreatic Tumor Cells and Their CPT-11-resistant Variants Cultured in vitro and Xenografted in Nude Mice," Jpn. J. Cancer Res., vol. 88, Aug. 1997, pp. 760-769.
Abstract of: Tamura et al., "Single agent activity of DS-8201a, a HER2-targeting antibody-drug conjugate, in breast cancer patients previously treated with T-DM1: Phase 1 dose escalation," Annals of Oncology, vol. 27, Supplement 6, 2016, pp. vi552-vi587.
Tan et al., "Antibody-drug conjugates with modified linker-payloads overcome resistance to a trastuzumab-maytansinoid conjugate in multiple cultured tumor cell models," Cancer Research, vol. 74, No. 19, Oct. 2014, Supplement Abstract 1830.
Vogel et al., "Efficacy and Safety of Trastuzumab as a Single Agent in First-Line Treatment of *HER2*-Overexpressing Metastatic Breast Cancer," Journal of Clinical Oncology, vol. 20, No. 3, Feb. 1, 2002, pp. 719-726.
Wente et al., "DE-310, a macromolecular prodrug of the topoisomerase-I-inhibitor exatecan (DX-8951), in patients with operable solid tumors," Investigational New Drugs, vol. 23, 2005, pp. 339-347.
Yano et al., "Comparison of HER2 gene amplification assessed by fluorescence in situ hybridization and HER2 protein expression assessed by immunohistochemistry in gastric cancer," Oncology Reports, vol. 15, 2006, pp. 65-71.
Extended European Search Report dated May 12, 2020 for corresponding European Patent Application No. 17858462.9.
Niikura et al: "Loss of Human Epidermal Growth Factor Receptor 2(HER2) Expression in Metastatic Sites of HER2-Overexpressing Primary Breast Tumors", Journal of Clinical Oncology, vol. 30, No. 6, Feb. 20, 2012 (Feb. 20, 2012), pp. 593-599.
Ogitani et al., "Bystander killing effect of DS-8201a, a novel anti-human epidermal growth factor receptor 2 antibody-drug conjugate, in tumors with human epidermal growth factor receptor 2 heterogeneity," Cancer Science, vol. 107, 2016, pp. 1039-1046.
Tamura et al, Single agent activity of DS-8201a, a HER2-targeting antibody-drug conjugate, in breast cancer patients previously treated with T-DM1: Phase 1 dose escalation, Annals of Oncology, vol. 27, Supplement 6, 2016, pp. vi552-vi587.
Acchione et al, Impact of linker and conjugation chemistry on antigen binding, Fc receptor binding and thermal stability of model antibody-drug conjugates, mAbs, 2012, pp. 362-372.
Colombian Reconsideration Petition dated Mar. 15, 2018 in corresponding application No. NC2016/0000187.
Rowinsky, Preclinical and Clinical Development of Exatecan(DX-8951f), Camptothecins in Cancer Therapy, 2005, pp. 317-318.

* cited by examiner

FIG. 1

SEQ ID NO: 1 - Amino acid sequence of heavy chain of humanized anti-HER2 monoclonal antibody EVQLVESGGGLVQPGGSLRLSCAASGFNIKDTYIHWVRQAPGKGLEWVARIYPTNGYTRYADSV
KGRFTISADTSKNTAYLQMNSLRAEDTAVYYCSRWGGDGFYAMDYWGQGTLVTVSSASTKGPSV
FPLAPSSKSTSGGTAALGCLVKDYFPEPVTVSWNSGALTSGVHTFPAVLQSSGLYSLSSVVTVP
SSSLGTQTYICNVNHKPSNTKVDKKVEPKSCDKTHTCPPCPAPELLGGPSVFLFPPKPKDTLMI
SRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLSP
GK

FIG. 2

SEQ ID NO: 2 - Amino acid sequence of light chain of humanized anti-HER2 monoclonal antibody DIQMTQSPSSLSASVGDRVTITCRASQDVNTAVAWYQQKPGKAPKLLIYSASFLYSGVPSRFSG
SRSGTDFTLTISSLQPEDFATYYCQQHYTTPPTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKVY
ACEVTHQGLSSPVTKSFNRGEC

THERAPY FOR DRUG-RESISTANT CANCER BY ADMINISTRATION OF ANTI-HER2 ANTIBODY/DRUG CONJUGATE

RELATED APPLICATIONS

The present application claims priority under 37 U.S.C. § 371 to International Patent Application No. PCT/JP2017/036215, filed Oct. 5, 2017, which claims priority to and the benefit of Japanese Patent Application Nos. 2016-199341, filed on Oct. 7, 2016, 2017-097589, filed on May 16, 2017, and 2017-172814, filed on Sep. 8, 2017. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, created on Nov. 11, 2020, is named 122622-0105 SL.txt and is 8,390 bytes in size.

TECHNICAL FIELD

The present invention relates to the treatment of drug-resistant cancer (hereinafter, also simply referred to as "resistant cancer"), in particular, cancer that has acquired resistance, with an antibody-drug conjugate having exatecan conjugated to an anti-HER2 antibody via a linker structure.

BACKGROUND ART

An antibody-drug conjugate (ADC) having a drug with cytotoxicity conjugated to an antibody, whose antigen is expressed on the surface of cancer cells and which also binds to an antigen capable of cellular internalization, and therefore can deliver the drug selectively to cancer cells, is thus expected to cause accumulation of the drug within cancer cells and to kill the cancer cells (Non-patent Literatures 1 to 3). As an ADC, Mylotarg (registered trademark; INN: gemtuzumab ozogamicin) in which calicheamicin is conjugated to an anti-CD33 antibody is approved as a therapeutic agent for acute myeloid leukemia. Further, Adcetris (registered trademark; INN: brentuximab vedotin), in which auristatin E is conjugated to an anti-CD30 antibody, has been approved as a therapeutic agent for Hodgkin's lymphoma and anaplastic large cell lymphoma (Non-patent Literature 4). Kadcyla (registered trademark; T-DM1; INN: trastuzumab emtansine; Non-patent Literature 34) in which an anti-HER2 antibody trastuzumab is conjugated to an antitumor drug maytansinoid (DM1) via a linker structure, has been further approved. The drugs contained in ADCs which have been approved until now target DNA or tubulin.

With regard to an antitumor agent, camptothecin derivatives, as low-molecular-weight compounds that inhibit topoisomerase I to exhibit an antitumor effect, are known. Among these, an antitumor compound represented by the following formula:

[Formula 1]

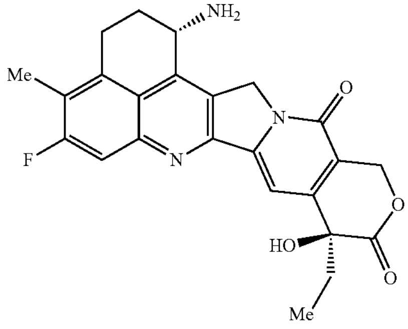

(exatecan, IUPAC name: (1S,9S)-1-amino-9-ethyl-5-fluoro-1,2,3,9,12,15-hexahydro-9-hydroxy-4-methyl-10H,13H-benzo[de]pyrano[3',4':6,7]indolizino[1,2-b]quinolin-10,13-dione (which can also be referred to as chemical name: (1S,9S)-1-amino-9-ethyl-5-fluoro-2,3-dihydro-9-hydroxy-4-methyl-1H,12H-benzo[de]pyrano[3',4':6,7]indolizino[1,2-b]quinolin-10,13(9H,15H)-dione)) is a water soluble derivative of camptothecin (Patent Literatures 1 and 2). Unlike Irinotecan currently used in clinical settings, this compound does not require activation by an enzyme for exhibiting its antitumor effect. Further, its inhibitory activity on topoisomerase I was observed to be higher than SN-38 which is the main pharmaceutically active substance of irinotecan and topotecan also used in clinical settings, and higher in vitro cytocidal activity was confirmed against various cancer cells. In particular, it was confirmed to have the effect against cancer cells that have resistance to SN-38 or the like due to expression of P-glycoprotein. Further, in a human tumor subcutaneously transplanted mouse model, it was confirmed to have a potent antitumor effect, and thus has undergone clinical studies, but has not been placed on the market yet (Non-patent Literatures 5 to 10). It remains unclear whether or not exatecan acts effectively as a drug for an ADC.

DE-310 is a complex in which exatecan is conjugated to a biodegradable carboxymethyldextran polyalcohol polymer via a GGFG peptide spacer (SEQ ID NO: 5) (Patent Literature 3). By converting exatecan into the form of a polymer prodrug, a high blood retention property can be maintained and also a high targeting property to tumor areas is passively increased by utilizing the increased permeability of newly formed blood vessels within tumors and retention property in tumor tissues. With DE-310, through cleavage of the peptide spacer by enzyme, exatecan and exatecan with glycine connected to an amino group are continuously released as main active substance, and as a result, the pharmacokinetics are improved. DE-310 was found to have higher effectiveness than exatecan administered alone even though the total dosage of exatecan contained in DE-310 is lower than in the case of administration of exatecan alone according to various tumor evaluation models in non-clinical studies. A clinical study was conducted for DE-310, and effective cases were also confirmed, including a report suggesting that the main active substance accumulates in tumors more than in normal tissues. However, there is also a report indicating that accumulation of DE-310 and the main active substance in tumors is not much different from accumulation in normal tissues in humans, and thus no passive targeting is observed in humans (Non-patent Literatures 11 to 14). As a result, DE-310 was not also commercialized, and it remains unclear whether or not exatecan effectively acts as a drug directed to such targeting.

As a compound relating to DE-310, a complex in which a structure moiety represented by —NH—$(CH_2)_4$—C(═O)— is inserted between the -GGFG- spacer (SEQ ID NO: 5) and exatecan to form -GGFG-NH—$(CH_2)_4$—C(═O)—("GGFG" disclosed as SEQ ID NO: 5) used as a spacer structure is also known (Patent Literature 4). However, the antitumor effect of said complex is not known at all.

HER2 is one of the products of a typical growth factor receptor type oncogene identified as human epidermal cell growth factor receptor 2-related oncogene, and is a transmembrane receptor protein having a molecular weight of 185 kDa and having a tyrosine kinase domain (Non-patent Literature 15). The DNA sequence and amino acid sequence of HER2 are disclosed on a public database, and can be referred to, for example, under Accession No. M11730 (GenBank), NP_004439.2 (NCBI), or the like.

HER2 (neu, ErbB-2) is one of the members of the EGFR (epidermal growth factor receptor) family and is activated by autophosphorylation at intracellular tyrosine residues by its homodimer formation or heterodimer formation with another EGFR receptor HER1 (EGFR, ErbB-1), HER3 (ErbB-3), or HER4 (ErbB-4) (Non-patent Literatures 16 to 18), thereby playing an important role in cell growth, differentiation, and survival in normal cells and cancer cells (Non-patent Literatures 19 and 20). HER2 is overexpressed in various cancer types such as breast cancer, gastric cancer, and ovarian cancer (Non-patent Literatures 21 to 26) and has been reported to be a negative prognosis factor for breast cancer (Non-patent Literatures 27 and 28).

Trastuzumab is a humanized antibody of a mouse anti-HER2 antibody 4D5 (Non-patent Literature 29 and Patent Literature 5), named as recombinant humanized anti-HER2 monoclonal antibody (huMAb4D5-8, rhuMAb HER2, Herceptin (registered trademark)) (Patent Literature 6). Trastuzumab specifically binds to the extracellular domain IV of HER2 and induces antibody-dependent cellular cytotoxicity (ADCC) or exerts an anticancer effect via the inhibition of signal transduction from HER2 (Non-patent Literatures 30 and 31). Trastuzumab is highly effective for tumors overexpressing HER2 (Non-patent Literature 32) and as such, was launched in 1999 in the USA and in 2001 in Japan as a therapeutic agent for patients with metastatic breast cancer overexpressing HER2.

Although the therapeutic effect of trastuzumab on breast cancer has been adequately proven (Non-patent Literature 33), allegedly about 15% of patients with breast cancer overexpressing HER2 who have received a wide range of conventional anticancer therapies are responders to trastuzumab. About 85% of patients of this population have no or merely weak response to trastuzumab treatment.

Thus, the need for a therapeutic agent targeting HER2 expression-related diseases has been recognized for patients affected by tumors overexpressing HER2 with no or weak response to trastuzumab or HER2-related disorders. T-DM1 having an antitumor drug conjugated to trastuzumab via a linker structure, and pertuzumab (Perjeta (registered trademark); Non-patent Literature 35 and Patent Literature 7) designed to target the extracellular domain II of HER2 and inhibit heterodimer formation have been developed. However, their responsiveness, activity strength, and accepted indications are still insufficient, and there are unsatisfied needs for targeting HER2.

As an antibody-drug conjugate, an antibody-drug conjugate having an anti-HER2 antibody and exatecan as components is known, and it has been revealed that, particularly, an antibody-drug conjugate having a structure given below has excellent properties (Patent Literature 8). Specifically, this is an antibody-drug conjugate in which a linker and a drug represented by the following formula are conjugated to an anti-HER2 antibody:

-(Succinimid-3-yl-N)—$CH_2CH_2CH_2CH_2CH_2$—C(═O)-GGFG-NH—$CH_2$—O—$CH_2$—C(═O)—(NH-DX) position ("GGFG" disclosed as SEQ ID NO: 5)

wherein

-(Succinimid-3-yl-N)- has a structure represented by the following formula:

[Formula 2]

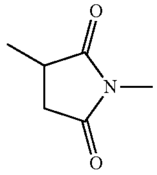

which is connected to the anti-HER2 antibody at position 3 thereof via a thioether bond and is connected to the methylene group in the linker structure containing this structure on the nitrogen atom at position 1, and —(NH-DX) represents a group represented by the following formula:

[Formula 3]

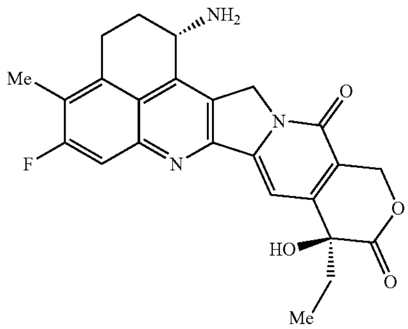

wherein the nitrogen atom of the amino group at position 1 is the connecting.

In the anti-HER2 antibody-drug conjugate described above, the drug-linker structure represented by the following formula:

-(Succinimid-3-yl-N)—$CH_2CH_2CH_2CH_2CH_2$—C(═O)-GGFG-NH—$CH_2$—O—$CH_2$—C(═O)—(NH-DX)

("GGFG" disclosed as SEQ ID NO: 5) are conjugated per molecule of the anti-HER2 antibody. Eight units at the maximum of this drug-linker structure can be connected to the interchain disulfide bond sites (2 sites between the heavy chain and the heavy chain, and 2 sites between the heavy chain and the light chain) of the antibody via thioether bonds. An anti-HER2 antibody-drug conjugate having almost 8 units of the drug-linker structure conjugated, which is close to this maximum number, has been obtained. It has been revealed that such an antibody-drug conjugate having a large number of conjugated drug molecules per antibody molecule exerts an excellent anticancer effect. For example, preclinical research using cancer-bearing mice has confirmed that the antibody-drug conjugate has cytocidal activity even if the expression of HER2 in cancer cells is low expression (Patent Literature 8 and Non-patent Literature 36). Hence, the anti-HER2 antibody-drug conjugate described above is expected as an excellent anticancer drug and is under clinical trial.

CITATION LIST

Patent Literatures

[Patent Literature 1] Japanese Patent Laid-Open No. 5-59061
[Patent Literature 2] Japanese Patent Laid-Open No. 8-337584
[Patent Literature 3] International Publication No. WO 1997/46260
[Patent Literature 4] International Publication No. WO 2000/25825
[Patent Literature 5] U.S. Pat. No. 5,677,171
[Patent Literature 6] U.S. Pat. No. 5,821,337
[Patent Literature 7] International Publication No. WO 01/00244
[Patent Literature 8] International Publication No. WO 2015/115091

Non-Patent Literatures

[Non-patent Literature 1] Ducry, L., et al., Bioconjugate Chem. (2010) 21, 5-13.
[Non-patent Literature 2] Alley, S. C., et al., Current Opinion in Chemical Biology (2010) 14, 529-537.
[Non-patent Literature 3] Damle N. K. Expert Opin. Biol. Ther. (2004) 4, 1445-1452.
[Non-patent Literature 4] Senter P. D., et al., Nature Biotechnology (2012) 30, 631-637.
[Non-patent Literature 5] Kumazawa, E., Tohgo, A., Exp. Opin. Invest. Drugs (1998) 7, 625-632.
[Non-patent Literature 6] Mitsui, I., et al., Jpn J. Cancer Res. (1995) 86, 776-782.
[Non-patent Literature 7] Takiguchi, S., et al., Jpn J. Cancer Res. (1997) 88, 760-769.
[Non-patent Literature 8] Joto, N. et al. Int J Cancer (1997) 72, 680-686.
[Non-patent Literature 9] Kumazawa, E. et al., Cancer Chemother. Pharmacol. (1998) 42, 210-220.
[Non-patent Literature 10] De Jager, R., et al., Ann N Y Acad Sci (2000) 922, 260-273.
[Non-patent Literature 11] Inoue, K. et al., Polymer Drugs in the Clinical Stage, Edited by Maeda et al. (2003) 145-153.
[Non-patent Literature 12] Kumazawa, E. et al., Cancer Sci (2004) 95, 168-175.
[Non-patent Literature 13] Soepenberg, O. et al., Clinical Cancer Research, (2005) 11, 703-711.
[Non-patent Literature 14] Wente M. N. et al., Investigational New Drugs (2005) 23, 339-347.
[Non-patent Literature 15] Coussens L, et al., Science. 1985; 230(4730):1132-1139.
[Non-patent Literature 16] Graus-Porta G, et al., EMBO J. 1997; 16; 1647-1655.
[Non-patent Literature 17] Karunagaran D, et al., EMBO J. 1996; 15:254-264.
[Non-patent Literature 18] Sliwkowski M X, et al., J. Biol. Chem. 1994; 269:14661-14665.
[Non-patent Literature 19] Di Fiore P P, et al., Science. 1987; 237:178-182.
[Non-patent Literature 20] Hudziak R M, et al., Proc Natl Acad Sci USA. 1987; 84:7159-7163.
[Non-patent Literature 21] Hardwick R, et al., Eur. J Surg Oncol. 1997 (23):30-35.
[Non-patent Literature 22] Korkaya H, et al., Oncogene. 2008; 27(47):6120-6130.
[Non-patent Literature 23] Yano T, et al., Oncol Rep. 2006; 15(1):65-71.
[Non-patent Literature 24] Slamon D J, et al., Science. 1987; 235:177-182.
[Non-patent Literature 25] Gravalos C, et al., Ann Oncol 19: 1523-1529, 2008.
[Non-patent Literature 26] Fukushige S et al., Mol Cell Biol 6: 955-958, 1986.
[Non-patent Literature 27] Slamon D J, et al. Science. 1989; 244:707-712.
[Non-patent Literature 28] Kaptain S et al., Diagn Mol Pathol 10:139-152, 2001.
[Non-patent Literature 29] Fendly. et al., Cancer Research 1990(50):1550-1558.
[Non-patent Literature 30] Sliwkowski M X, et al., Semin Oncol. 1999; 26(4, Suppl 12):60-70.
[Non-patent Literature 31] Hudis C A, et al., N Engl J Med. 357: 39-51, 2007.
[Non-patent Literature 32] Vogel C L, et al., J Clin Oncol. 2002; 20(3):719-726.
[Non-patent Literature 33] Baselga et al., J. Clin. Oncol. 14:737-744 (1996).
[Non-patent Literature 34] Burris, III et al., J Clin Oncol 2011; 29:398-405.
[Non-patent Literature 35] Adams C W, et al., Cancer Immunol Immunother. 2006; 6:717-727.
[Non-patent Literature 36] Ogitani Y. et al., Clinical Cancer Research, 2016, Oct. 15; 22(20):5097-5108, Epub 2016 Mar. 29.

SUMMARY OF INVENTION

Technical Problem

It is known that when administration for treatment is continued, an anticancer drug is confirmed to temporarily have an effect, but loses its therapeutic effect due to the acquired resistance (hereinafter, also referred to as "secondary resistance" in the present invention) of cancer cells. For example, it is known that as a result of treating HER2-expressing cancer with trastuzumab emtansine, cancer that has acquired resistance or refractoriness to trastuzumab emtansine occurs newly. Thus, there is a demand for a medicine that can provide a novel treatment method effective for cancer that has acquired such resistance (hereinafter, also referred to as "secondary resistant cancer" in the present invention). A main object of the present invention is to provide a therapeutic agent and a treatment method having a sufficient therapeutic effect even on HER2-expressing cancer that has acquired resistance or refractoriness by treatment with an existing anti-HER2 drug.

Furthermore, Cancer originally having resistance or refractoriness to existing anti-HER2 drug, albeit expressing HER2 (in other words, HER2-expressing cancer having resistance or refractoriness intrinsic to the cancer to an existing anti-HER2 drug independently of treatment with the existing anti-HER2 drug) is known. Examples of such HER2-expressing cancer can include HER2 low-expressing cancer and solid cancer other than breast cancer and gastric cancer (e.g., colorectal cancer and non-small cell lung cancer). Another main object of the present invention is to provide a therapeutic agent and a treatment method having a sufficient therapeutic effect even on such HER2-expressing cancer.

Solution to Problem

The present inventors found in preclinical and clinical trials that an antibody-drug conjugate in which a linker and a drug represented by the following formula:

-(Succinimid-3-yl-N)—$CH_2CH_2CH_2CH_2CH_2$—C(═O)-GGFG-NH—$CH_2$—O—$CH_2$—C(═O)—(NH-DX)

("GGFG" disclosed as SEQ ID NO: 5) are conjugated to an anti-HER2 antibody exhibits an excellent antitumor effect on HER2-expressing cancer having resistance or refractoriness to an existing anti-HER2 drug and has also favorable safety profile. This antibody-drug conjugate can be expected to offer effective treatment even for secondary resistant cancer.

Specifically, the present invention provides the following [1] to [144].

[1] A therapeutic agent for HER2-expressing cancer having resistance or refractoriness to an existing anti-HER2 drug, comprising an antibody-drug conjugate in which a linker and a drug represented by the following formula are conjugated to an anti-HER2 antibody:

(Succinimid-3-yl-N)—$CH_2CH_2CH_2CH_2CH_2$—C(═O)-GGFG-NH—$CH_2$—O—$CH_2$—C(═O)—(NH-DX)

("GGFG" disclosed as SEQ ID NO: 5)

wherein (Succinimid-3-yl-N)- has a structure represented by the following formula:

[Formula 4]

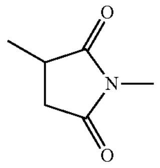

which is connected to the anti-HER2 antibody at position 3 thereof via a thioether bond and is connected to the methylene group in the linker structure containing this structure on the nitrogen atom at position 1, (NH-DX) represents a group represented by the following formula:

[Formula 5]

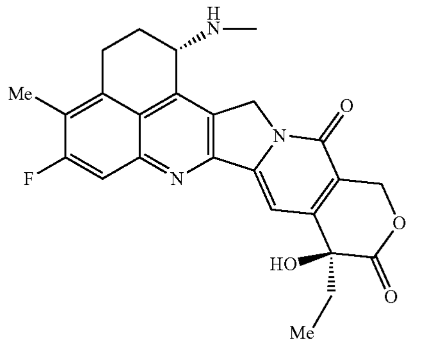

wherein the nitrogen atom of the amino group at position 1 is the connecting position, and GGFG-represents the tetrapeptide residue of -Gly-Gly-Phe-Gly- (SEQ ID NO: 5).

[2] The therapeutic agent according to [1], wherein the resistance or refractoriness is resistance or refractoriness acquired by the cancer due to treatment with the existing anti-HER2 drug.

[3] The therapeutic agent according to [1], wherein the resistance or refractoriness is resistance or refractoriness intrinsic to the cancer independently of treatment with the existing anti-HER2 drug.

[4] The therapeutic agent according to any of [1] to [3], wherein the existing anti-HER2 drug is at least one selected from the group consisting of trastuzumab emtansine, trastuzumab, pertuzumab, and lapatinib.

[5] The therapeutic agent according to any of [1] to [3], wherein the existing anti-HER2 drug is trastuzumab emtansine.

[6] The therapeutic agent according to any of [1] to [3], wherein the existing anti-HER2 drug is trastuzumab.

[7] The therapeutic agent according to any of [1] to [6], for use in administrating to a patient having a history of treatment with an existing anticancer drug.

[8] The therapeutic agent according to [7], wherein the existing anticancer drug comprises at least one selected from the group consisting of trastuzumab emtansine, trastuzumab, pertuzumab, lapatinib, irinotecan, cisplatin, carboplatin, oxaliplatin, fluorouracil, gemcitabine, capecitabine, paclitaxel, docetaxel, doxorubicin, epirubicin, cyclophosphamide, mitomycin C, a tegafur-gimeracil-oteracil combination drug, cetuximab, panitumumab, bevacizumab, ramucirumab, regorafenib, a trifluridine-tipiracil combination drug, gefitinib, erlotinib, afatinib, methotrexate, and pemetrexed.

[9] The therapeutic agent according to [7], wherein the existing anticancer drug comprises trastuzumab emtansine.

[10] The therapeutic agent according to [7], wherein the existing anticancer drug comprises trastuzumab.

[11] The therapeutic agent according to [7], wherein the existing anticancer drug comprises irinotecan.

[12] The therapeutic agent according to any of [1] to [11], wherein an average number of units of the drug-linker structure conjugated per antibody molecule of the antibody-drug conjugate is in a range of 7 to 8.

[13] The therapeutic agent according to any of [1] to [11], wherein an average number of units of the drug-linker structure conjugated per antibody molecule of the antibody-drug conjugate is in a range of 7.5 to 8.

[14] The therapeutic agent according to any of [1] to [13], wherein the anti-HER2 antibody in the antibody-drug conjugate is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

[15] The therapeutic agent according to any of [1] to [13], wherein the anti-HER2 antibody in the antibody-drug conjugate is an antibody comprising a heavy chain consisting of the amino acid sequence represented by SEQ ID NO: 1 and a light chain consisting of the amino acid sequence represented by SEQ ID NO: 2.

[16] The therapeutic agent according to any of [1] to [15], wherein a dose per administration of the antibody-drug conjugate is in a range of 5.4 mg/kg to 8 mg/kg.

[17] The therapeutic agent according to any of [1] to [15], wherein a dose per administration of the antibody-drug conjugate is 5.4 mg/kg.

[18] The therapeutic agent according to any of [1] to [15], wherein a dose per administration of the antibody-drug conjugate is 6.4 mg/kg.

[19] The therapeutic agent according to any of [1] to [15], wherein a dose per administration of the antibody-drug conjugate is 7.4 mg/kg.

[20] The therapeutic agent according to any of [1] to [15], wherein a dose per administration of the antibody-drug conjugate is 8 mg/kg.

[21] The therapeutic agent according to any of [1] to [20], wherein the antibody-drug conjugate is administered once every 3 weeks.

[22] The therapeutic agent according to any of [1] to [21], for use in treatment of at least one cancer selected from the group consisting of breast cancer, gastric cancer, colorectal cancer, non-small cell lung cancer, esophageal cancer, salivary gland cancer, esophagogastric junction adenocarcinoma, bile duct cancer, Paget's disease, pancreatic cancer, ovarian cancer, uterine cancer and sarcoma.

[23] The therapeutic agent according to any of [1] to [21], for use in treatment of breast cancer.

[24] The therapeutic agent according to any of [1] to [21], for use in treatment of gastric cancer.

[25] The therapeutic agent according to any of [1] to [21], for use in treatment of gastric cancer and esophagogastric junction adenocarcinoma.

[26] The therapeutic agent according to any of [1] to [21], for use in treatment of colorectal cancer.

[27] The therapeutic agent according to any of [1] to [21], for use in treatment of non-small cell lung cancer.

[28] The therapeutic agent according to any of [1] to [21], for use in treatment of salivary gland cancer.

[29] The therapeutic agent according to any of [1] to [28], wherein the HER2-expressing cancer is HER2-overexpressing cancer.

[30] The therapeutic agent according to [29], wherein the HER2-overexpressing cancer is cancer given a score of 3+ for the expression of HER2 in an immunohistochemical method.

[31] The therapeutic agent according to [29], wherein the HER2-overexpressing cancer is cancer given a score of 2+ for the expression of HER2 in an immunohistochemical method and determined as positive for the expression of HER2 in an in situ hybridization method.

[32] The therapeutic agent according to any of [1] to [28], wherein the HER2-expressing cancer is HER2 low-expressing cancer.

[33] The therapeutic agent according to [32], wherein the HER2 low-expressing cancer is cancer given a score of 2+ for the expression of HER2 in an immunohistochemical method and determined as negative for the expression of HER2 in an in situ hybridization method.

[34] The therapeutic agent according to [32], wherein the HER2 low-expressing cancer is cancer given a score of 1+ for the expression of HER2 in an immunohistochemical method.

[35] The therapeutic agent according to any of [1] to [34], for use in treatment of inoperable or recurrent cancer.

[36] The therapeutic agent according to any of [1] to [35], comprising a pharmaceutically acceptable formulation component.

[37] A method for treating HER2-expressing cancer having resistance or refractoriness to an existing anti-HER2 drug, comprising administering an antibody-drug conjugate in which a linker and a drug represented by the following formula are conjugated to an anti-HER2 antibody to a patient in need of the treatment of the HER2-expressing cancer having resistance or refractoriness to an existing anti-HER2 drug:

-(Succinimid-3-yl-N)—$CH_2CH_2CH_2CH_2CH_2$—C(═O)-GGFG-NH—$CH_2$—O—$CH_2$—C(═O)—(NH-DX) ("GGFG" disclosed as SEQ ID NO: 5)

wherein (Succinimid-3-yl-N)- has a structure represented by the following formula:

[Formula 6]

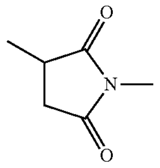

which is connected to the anti-HER2 antibody at position 3 thereof via a thioether bond and is connected to the methylene group in the linker structure containing this structure on the nitrogen atom at position 1, (NH-DX) represents a group represented by the following formula:

[Formula 7]

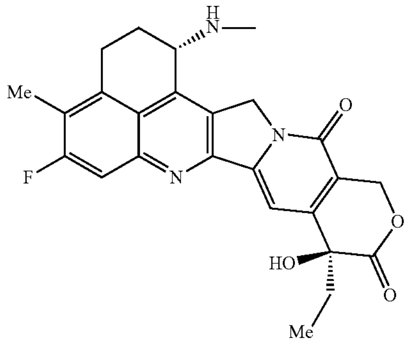

wherein the nitrogen atom of the amino group at position 1 is the connecting position, and -GGFG- represents the tetrapeptide residue of -Gly-Gly-Phe-Gly- (SEQ ID NO: 5).

[38] The method according to [37], wherein the resistance or refractoriness is resistance or refractoriness acquired by the cancer due to treatment with the existing anti-HER2 drug.

[39] The method according to [37], wherein the resistance or refractoriness is resistance or refractoriness intrinsic to the cancer independently of treatment with the existing anti-HER2 drug.

[40] The method according to any of [37] to [39], wherein the existing anti-HER2 drug is at least one selected from the group consisting of trastuzumab emtansine, trastuzumab, pertuzumab, and lapatinib.

[41] The method according to any of [37] to [39], wherein the existing anti-HER2 drug is trastuzumab emtansine.

[42] The method according to any of [37] to [39], wherein the existing anti-HER2 drug is trastuzumab.

[43] The method according to any of [37] to [42], which is performed for a patient having a history of treatment with an existing anticancer drug.

[44] The method according to [43], wherein the existing anticancer drug comprises at least one selected from the group consisting of trastuzumab emtansine, trastuzumab, pertuzumab, lapatinib, irinotecan, cisplatin, carboplatin, oxaliplatin, fluorouracil, gemcitabine, capecitabine, paclitaxel, docetaxel, doxorubicin, epirubicin, cyclophosphamide, mitomycin C, a tegafur-gimeracil-oteracil combination drug, cetuximab, panitumumab, bevacizumab, ramucirumab, regorafenib, a trifluridine-tipiracil combination drug, gefitinib, erlotinib, afatinib, methotrexate, and pemetrexed.

[45] The method according to [43], wherein the existing anticancer drug comprises trastuzumab emtansine.

[46] The method according to [43], wherein the existing anticancer drug comprises trastuzumab.

[47] The method according to [43], wherein the existing anticancer drug comprises irinotecan.

[48] The method according to any of [37] to [47], wherein an average number of units of the drug-linker structure conjugated per antibody molecule of the antibody-drug conjugate is in a range of 7 to 8.

[49] The method according to any of [37] to [47], wherein an average number of units of the drug-linker structure conjugated per antibody molecule of the antibody-drug conjugate is in a range of 7.5 to 8.

[50] The method according to any of [37] to [49], wherein the anti-HER2 antibody in the antibody-drug conjugate is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

[51] The method according to any of [37] to [49], wherein the anti-HER2 antibody in the antibody-drug conjugate is an antibody comprising a heavy chain consisting of the amino acid sequence represented by SEQ ID NO: 1 and a light chain consisting of the amino acid sequence represented by SEQ ID NO: 2.

[52] The method according to any of [37] to [51], wherein a dose per administration of the antibody-drug conjugate is in a range of 5.4 mg/kg to 8 mg/kg.

[53] The method according to any of [37] to [51], wherein a dose per administration of the antibody-drug conjugate is 5.4 mg/kg.

[54] The method according to any of [37] to [51], wherein a dose per administration of the antibody-drug conjugate is 6.4 mg/kg.

[55] The method according to any of [37] to [51], wherein a dose per administration of the antibody-drug conjugate is 7.4 mg/kg.

[56] The method according to any of [37] to [51], wherein a dose per administration of the antibody-drug conjugate is 8 mg/kg.

[57] The method according to any of [37] to [56], wherein the antibody-drug conjugate is administered once every 3 weeks.

[58] The method according to any of [37] to [57], for use in treatment of at least one cancer selected from the group consisting of breast cancer, gastric cancer, colorectal cancer, non-small cell lung cancer, esophageal cancer, salivary gland cancer, esophagogastric junction adenocarcinoma, bile duct cancer, Paget's disease, pancreatic cancer, ovarian cancer, uterine cancer and sarcoma.

[59] The method according to any of [37] to [57], for use in treatment of breast cancer.

[60] The method according to any of [37] to [57], for use in treatment of gastric cancer.

[61] The method according to any of [37] to [57], for use in treatment of gastric cancer and esophagogastric junction adenocarcinoma.

[62] The method according to any of [37] to [57], for use in treatment of colorectal cancer.

[63] The method according to any of [37] to [57], for use in treatment of non-small cell lung cancer.

[64] The method according to any of [37] to [57], for use in treatment of salivary gland cancer.

[65] The method according to any of [37] to [64], wherein the HER2-expressing cancer is HER2-overexpressing cancer.

[66] The method according to [65], wherein the HER2-overexpressing cancer is cancer given a score of 3+ for the expression of HER2 in an immunohistochemical method.

[67] The method according to [65], wherein the HER2-overexpressing cancer is cancer given a score of 2+ for the expression of HER2 in an immunohistochemical method and determined as positive for the expression of HER2 in an in situ hybridization method.

[68] The method according to any of [37] to [64], wherein the HER2-expressing cancer is HER2 low-expressing cancer.

[69] The method according to [68], wherein the HER2 low-expressing cancer is cancer given a score of 2+ for the expression of HER2 in an immunohistochemical method and determined as negative for the expression of HER2 in an in situ hybridization method.

[70] The method according to [68], wherein the HER2 low-expressing cancer is cancer given a score of 1+ for the expression of HER2 in an immunohistochemical method.

[71] The method according to any of [37] to [70], for use in treatment of inoperable or recurrent cancer.

[72] The method according to any of [37] to [71], wherein the antibody-drug conjugate is administered together with a pharmaceutically acceptable formulation component.

[73] An antibody-drug conjugate in which a linker and a drug represented by the following formula are conjugated to an anti-HER2 antibody, for use as a therapeutic agent for HER2-expressing cancer having resistance or refractoriness to an existing anti-HER2 drug:

-(Succinimid-3-yl-N)—$CH_2CH_2CH_2CH_2CH_2$—C(=O)-GGFG-NH—$CH_2$—O—$CH_2$—C(=O)—(NH-DX) ("GGFG" disclosed as SEQ ID NO: 5)

wherein (Succinimid-3-yl-N)- has a structure represented by the following formula:

[Formula 8]

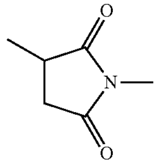

which is connected to the anti-HER2 antibody at position 3 thereof via a thioether bond and is connected to the methylene group in the linker structure containing this structure on the nitrogen atom at position 1, (NH-DX) represents a group represented by the following formula:

[Formula 9]

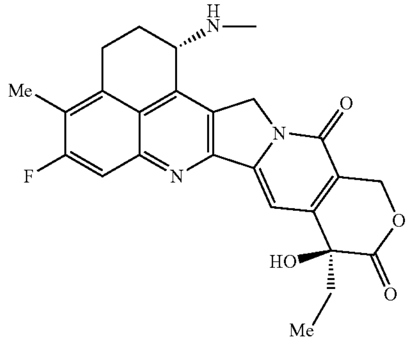

wherein the nitrogen atom of the amino group at position 1 is the connecting position, and -GGFG- represents the tetrapeptide residue of -Gly-Gly-Phe-Gly- (SEQ ID NO: 5).

[74] The antibody-drug conjugate according to [73], wherein the resistance or refractoriness is resistance or refractoriness acquired by the cancer due to treatment with the existing anti-HER2 drug.

[75] The antibody-drug conjugate according to [73], wherein the resistance or refractoriness is resistance or refractoriness intrinsic to the cancer independently of treatment with the existing anti-HER2 drug.

[76] The antibody-drug conjugate according to any of [73] to [75], wherein the existing anti-HER2 drug is at least one selected from the group consisting of trastuzumab emtansine, trastuzumab, pertuzumab, and lapatinib.

[77] The antibody-drug conjugate according to any of [73] to [75], wherein the existing anti-HER2 drug is trastuzumab emtansine.

[78] The antibody-drug conjugate according to any of [73] to [75], wherein the existing anti-HER2 drug is trastuzumab.

[79] The antibody-drug conjugate according to any of [73] to [78], for use in administrating to a patient having a history of treatment with an existing anticancer drug.

[80] The antibody-drug conjugate according to [79], wherein the existing anticancer drug comprises at least one selected from the group consisting of trastuzumab emtansine, trastuzumab, pertuzumab, lapatinib, irinotecan, cisplatin, carboplatin, oxaliplatin, fluorouracil, gemcitabine, capecitabine, paclitaxel, docetaxel, doxorubicin, epirubicin, cyclophosphamide, mitomycin C, a tegafur-gimeracil-oteracil combination drug, cetuximab, panitumumab, bevacizumab, ramucirumab, regorafenib, a trifluridine-tipiracil combination drug, gefitinib, erlotinib, afatinib, methotrexate, and pemetrexed.

[81] The antibody-drug conjugate according to [79], wherein the existing anticancer drug comprises trastuzumab emtansine.

[82] The antibody-drug conjugate according to [79], wherein the existing anticancer drug comprises trastuzumab.

[83] The antibody-drug conjugate according to [79], wherein the existing anticancer drug comprises irinotecan.

[84] The antibody-drug conjugate according to any of [73] to [83], wherein an average number of units of the drug-linker structure conjugated per antibody molecule of the antibody-drug conjugate is in a range of 7 to 8.

[85] The antibody-drug conjugate according to any of [73] to [83], wherein an average number of units of the drug-linker structure conjugated per antibody molecule of the antibody-drug conjugate is in a range of 7.5 to 8.

[86] The antibody-drug conjugate according to any of [73] to [85], wherein the anti-HER2 antibody in the antibody-drug conjugate is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

[87] The antibody-drug conjugate according to any of [73] to [85], wherein the anti-HER2 antibody in the antibody-drug conjugate is an antibody comprising a heavy chain consisting of the amino acid sequence represented by SEQ ID NO: 1 and a light chain consisting of the amino acid sequence represented by SEQ ID NO: 2.

[88] The antibody-drug conjugate according to any of [73] to [87], wherein a dose per administration of the antibody-drug conjugate is in a range of 5.4 mg/kg to 8 mg/kg.

[89] The antibody-drug conjugate according to any of [73] to [87], wherein a dose per administration of the antibody-drug conjugate is 5.4 mg/kg.

[90] The antibody-drug conjugate according to any of [73] to [87], wherein a dose per administration of the antibody-drug conjugate is 6.4 mg/kg.

[91] The antibody-drug conjugate according to any of [73] to [87], wherein a dose per administration of the antibody-drug conjugate is 7.4 mg/kg.

[92] The antibody-drug conjugate according to any of [73] to [87], wherein a dose per administration of the antibody-drug conjugate is 8 mg/kg.

[93] The antibody-drug conjugate according to any of [73] to [92], wherein the antibody-drug conjugate is administered once every 3 weeks.

[94] The antibody-drug conjugate according to any of [73] to [93], for use in treatment of at least one cancer selected from the group consisting of breast cancer, gastric cancer, colorectal cancer, non-small cell lung cancer, esophageal cancer, salivary gland cancer, esophagogastric junction adenocarcinoma, bile duct cancer, Paget's disease, pancreatic cancer, ovarian cancer, uterine cancer and sarcoma.

[95] The antibody-drug conjugate according to any of [73] to [93], for use in treatment of breast cancer.

[96] The antibody-drug conjugate according to any of [73] to [93], for use in treatment of gastric cancer.

[97] The antibody-drug conjugate according to any of [73] to [93], for use in treatment of gastric cancer and esophagogastric junction adenocarcinoma.

[98] The antibody-drug conjugate according to any of [73] to [93], for use in treatment of colorectal cancer.

[99] The antibody-drug conjugate according to any of [73] to [93], for use in treatment of non-small cell lung cancer.

[100] The antibody-drug conjugate according to any of [73] to [93], for use in treatment of salivary gland cancer.

[101] The antibody-drug conjugate according to any of [73] to [100], wherein the HER2-expressing cancer is HER2-overexpressing cancer.

[102] The antibody-drug conjugate according to [101], wherein the HER2-overexpressing cancer is cancer given a score of 3+ for the expression of HER2 in an immunohistochemical method.

[103] The antibody-drug conjugate according to [101], wherein the HER2-overexpressing cancer is cancer given a score of 2+ for the expression of HER2 in an immunohistochemical method and determined as positive for the expression of HER2 in an in situ hybridization method.

[104] The antibody-drug conjugate according to any of [73] to [100], wherein the HER2-expressing cancer is HER2 low-expressing cancer.

[105] The antibody-drug conjugate according to [104], wherein the HER2 low-expressing cancer is cancer given a score of 2+ for the expression of HER2 in an immunohistochemical method and determined as negative for the expression of HER2 in an in situ hybridization method.

[106] The antibody-drug conjugate according to [104], wherein the HER2 low-expressing cancer is cancer given a score of 1+ for the expression of HER2 in an immunohistochemical method.

[107] The antibody-drug conjugate according to any of [73] to [106], for use in treatment of inoperable or recurrent cancer.

[108] The antibody-drug conjugate according to any of [73] to [107], which is administered together with a pharmaceutically acceptable formulation component.

[109] Use of an antibody-drug conjugate in which a linker and a drug represented by the following formula are conjugated to an anti-HER2 antibody, for the production of a medicine for treating HER2-expressing cancer having resistance or refractoriness to an existing anti-HER2 drug:

-(Succinimid-3-yl-N)—$CH_2CH_2CH_2CH_2CH_2$—C(=O)-GGFG-NH—$CH_2$—O—$CH_2$—C(=O)—(NH-DX) ("GGFG" disclosed as SEQ ID NO: 5)

wherein (Succinimid-3-yl-N)- has a structure represented by the following formula:

[Formula 10]

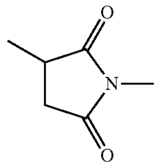

which is connected to the anti-HER2 antibody at position 3 thereof via a thioether bond and is connected to the methylene group in the linker structure containing this structure on the nitrogen atom at position 1, (NH-DX) represents a group represented by the following formula:

[Formula 11]

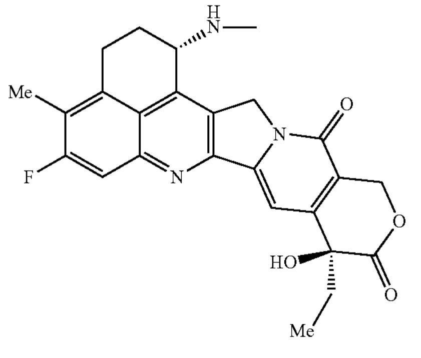

wherein the nitrogen atom of the amino group at position 1 is the connecting position, and -GGFG- represents the tetrapeptide residue of -Gly-Gly-Phe-Gly- (SEQ ID NO: 5).

[110] The use according to [109], wherein the resistance or refractoriness is resistance or refractoriness acquired by the cancer due to treatment with the existing anti-HER2 drug.

[111] The use according to [109], wherein the resistance or refractoriness is resistance or refractoriness intrinsic to the cancer independently of treatment with the existing anti-HER2 drug.

[112] The use according to any of [109] to [111], wherein the existing anti-HER2 drug is at least one selected from the group consisting of trastuzumab emtansine, trastuzumab, pertuzumab, and lapatinib.

[113] The use according to any of [109] to [111], wherein the existing anti-HER2 drug is trastuzumab emtansine.

[114] The use according to any of [109] to [111], wherein the existing anti-HER2 drug is trastuzumab.

[115] The use according to any of [109] to [114], which is for the production of the medicine for use in administrating to a patient having a history of treatment with an existing anticancer drug.

[116] The use according to [115], wherein the existing anticancer drug comprises at least one selected from the group consisting of trastuzumab emtansine, trastuzumab, pertuzumab, lapatinib, irinotecan, cisplatin, carboplatin, oxaliplatin, fluorouracil, gemcitabine, capecitabine, paclitaxel, docetaxel, doxorubicin, epirubicin, cyclophosphamide, mitomycin C, a tegafur-gimeracil-oteracil combination drug, cetuximab, panitumumab, bevacizumab, ramucirumab, regorafenib, a trifluridine-tipiracil combination drug, gefitinib, erlotinib, afatinib, methotrexate, and pemetrexed.

[117] The use according to [115], wherein the existing anticancer drug comprises trastuzumab emtansine.

[118] The use according to [115], wherein the existing anticancer drug comprises trastuzumab.

[119] The use according to [115], wherein the existing anticancer drug comprises irinotecan.

[120] The use according to any of [109] to [119], wherein an average number of units of the drug-linker structure conjugated per antibody molecule of the antibody-drug conjugate is in a range of 7 to 8.

[121] The use according to any of [109] to [119], wherein an average number of units of the drug-linker structure conjugated per antibody molecule of the antibody-drug conjugate is in a range of 7.5 to 8.

[122] The use according to any of [109] to [121], wherein the anti-HER2 antibody in the antibody-drug conjugate is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

[123] The use according to any of [109] to [121], wherein the anti-HER2 antibody in the antibody-drug conjugate is an antibody comprising a heavy chain consisting of the amino acid sequence represented by SEQ ID NO: 1 and a light chain consisting of the amino acid sequence represented by SEQ ID NO: 2.

[124] The use according to any of [109] to [123], wherein a dose per administration of the antibody-drug conjugate is in a range of 5.4 mg/kg to 8 mg/kg.

[125] The use according to any of [109] to [123], wherein a dose per administration of the antibody-drug conjugate is 5.4 mg/kg.

[126] The use according to any of [109] to [123], wherein a dose per administration of the antibody-drug conjugate is 6.4 mg/kg.

[127] The use according to any of [109] to [123], wherein a dose per administration of the antibody-drug conjugate is 7.4 mg/kg.

[128] The use according to any of [109] to [123], wherein a dose per administration of the antibody-drug conjugate is 8 mg/kg.

[129] The use according to any of [109] to [128], wherein the antibody-drug conjugate is administered once every 3 weeks.

[130] The use according to any of [109] to [129], which is for the production of the medicine for use in treatment of at least one cancer selected from the group consisting of breast cancer, gastric cancer, colorectal cancer, non-small cell lung cancer, esophageal cancer, salivary gland cancer, esophagogastric junction adenocarcinoma, bile duct cancer, Paget's disease, pancreatic cancer, ovarian cancer, uterine cancer and sarcoma.

[131] The use according to any of [109] to [129], which is for the production of the medicine for use in treatment of breast cancer.

[132] The use according to any of [109] to [129], which is for the production of the medicine for use in treatment of gastric cancer.

[133] The use according to any of [109] to [129], which is for the production of the medicine for use in treatment of gastric cancer and esophagogastric junction adenocarcinoma.

[134] The use according to any of [109] to [129], which is for the production of the medicine for use in treatment of colorectal cancer.

[135] The use according to any of [109] to [129], which is for the production of the medicine for use in treatment of non-small cell lung cancer.

[136] The use according to any of [109] to [129], which is for the production of the medicine for use in treatment of salivary gland cancer.

[137] The use according to any of [109] to [136], wherein the HER2-expressing cancer is HER2-overexpressing cancer.

[138] The use according to [137], wherein the HER2-overexpressing cancer is cancer given a score of 3+ for the expression of HER2 in an immunohistochemical method.

[139] The use according to [137], wherein the cancer overexpressing HER2 is HER2-overexpressing cancer given a score of 2+ for the expression of HER2 in an immunohistochemical method and determined as positive for the expression of HER2 in an in situ hybridization method.

[141] The use according to any of [109] to [136], wherein the HER2-expressing cancer is HER2 low-expressing cancer.

[141] The use according to [140], wherein the HER2 low-expressing cancer is cancer given a score of 2+ for the expression of HER2 in an immunohistochemical method and determined as negative for the expression of HER2 in an in situ hybridization method.

[142] The use according to [140], wherein the HER2 low-expressing cancer is cancer given a score of 1+ for the expression of HER2 in an immunohistochemical method.

[143] The use according to any of [109] to [142], which is for the production of the medicine for use in treatment of inoperable or recurrent cancer.

[144] The use according to any of [109] to [143], wherein the medicine comprises a pharmaceutically acceptable formulation component.

The present invention can also be defined as follows.

[1] Use of an antibody-drug conjugate in which a linker and a drug represented by the following formula are conjugated to an anti-HER2 antibody, a salt thereof, or a hydrate thereof for the treatment of resistant cancer:

-(Succinimid-3-yl-N)—$CH_2CH_2CH_2CH_2CH_2$—C(═O)-GGFG-NH—$CH_2$—O—$CH_2$—C(═O)—(NH-DX) ("GGFG" disclosed as SEQ ID NO: 5)

wherein (Succinimid-3-yl-N)- has a structure represented by the following formula:

[Formula 12]

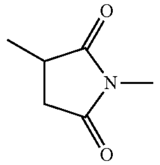

which is connected to the anti-HER2 antibody at position 3 thereof via a thioether bond and is connected to the methylene group in the linker structure containing this structure on the nitrogen atom at position 1, and (NH-DX) represents a group represented by the following formula:

[Formula 13]

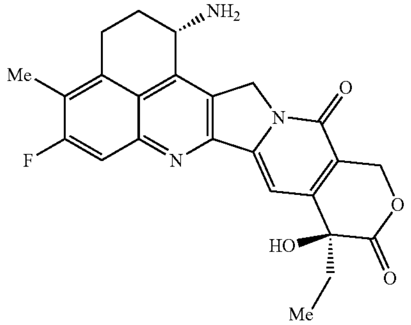

wherein the nitrogen atom of the amino group at position 1 is the connecting position.

[2] The use according to [1], wherein the resistant cancer is secondary resistant cancer.

[3] The use according to [2], wherein the secondary resistance is secondary resistance caused by the administration of an antibody-drug conjugate comprising an anti-HER2 antibody.

[4] The use according to [2] or [3], wherein the secondary resistance is secondary resistance acquired by the administration of T-DM1 which is an anti-HER2 antibody-drug conjugate.

[5] The use according to [2], wherein the secondary resistance is secondary resistance caused by the administration of an anti-HER2 antibody.

[6] The use according to any of [1] to [5], wherein an average number of units of the drug-linker structure conjugated per antibody molecule of the antibody-drug conjugate is in a range of 2 to 8.

[7] The use according to any of [1] to [5], wherein an average number of units of the drug-linker structure conjugated per antibody molecule of the antibody-drug conjugate is in a range of 3 to 8.

[8] The use according to any of [1] to [5], wherein an average number of units of the drug-linker structure conjugated per antibody molecule of the antibody-drug conjugate is in a range of 7 to 8.

[9] The use according to any of [1] to [5], wherein an average number of units of the drug-linker structure conjugated per antibody molecule of the antibody-drug conjugate is in a range of 7.5 to 8.

[10] The use according to any of [1] to [9], wherein the dose of the antibody-drug conjugate is in a range of 0.8 mg/kg to 8 mg/kg.

[11] The use according to any of [1] to [10], wherein the antibody-drug conjugate is administered once every 3 weeks.

[12] The use according to any of [1] to [11], wherein the resistant cancer is lung cancer, urothelial cancer, colorectal cancer, prostate cancer, ovarian cancer, pancreatic cancer, breast cancer, bladder cancer, gastric cancer, gastrointestinal stromal tumor, uterine cervix cancer, esophageal cancer, squamous cell carcinoma, peritoneal cancer, liver cancer, hepatocellular cancer, colon cancer, rectal cancer, colorectal cancer, endometrial cancer, uterine cancer, salivary gland cancer, kidney cancer, vulval cancer, thyroid cancer, penis cancer, leukemia, malignant lymphoma, plasmacytoma, myeloma, or sarcoma.

[13] A pharmaceutical composition for treatment of resistant cancer, comprising an antibody-drug conjugate in which a linker and a drug represented by the following formula are conjugated to an anti-HER2 antibody, a salt thereof, or a hydrate thereof as an active component, and a pharmaceutically acceptable formulation component:

-(Succinimid-3-yl-N)—$CH_2CH_2CH_2CH_2CH_2$—C(═O)-GGFG-NH—$CH_2$—O—$CH_2$—C(═O)—(NH-DX) ("GGFG" disclosed as SEQ ID NO: 5)

wherein (Succinimid-3-yl-N)- has a structure represented by the following formula:

[Formula 14]

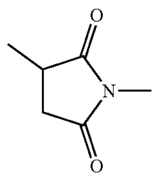

which is connected to the anti-HER2 antibody at position 3 thereof via a thioether bond and is connected to the methylene group in the linker structure containing this structure on the nitrogen atom at position 1, and (NH-DX) represents a group represented by the following formula:

[Formula 15]

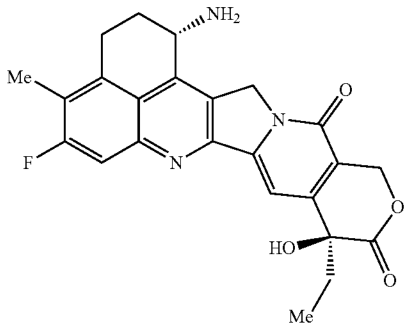

wherein the nitrogen atom of the amino group at position 1 is the connecting position.

[14] The pharmaceutical composition for treatment according to [13], wherein the resistant cancer is secondary resistant cancer.

[15] The pharmaceutical composition for treatment according to [13], wherein the secondary resistance is secondary resistance caused by the administration of an antibody-drug conjugate comprising an anti-HER2 antibody.

[16] The pharmaceutical composition for treatment according to [14] or [15], wherein the secondary resistance is secondary resistance acquired by the administration of T-DM1 which is an anti-HER2 antibody-drug conjugate.

[17] The pharmaceutical composition for treatment according to [14], wherein the secondary resistance is secondary resistance caused by the administration of an anti-HER2 antibody.

[18] The pharmaceutical composition for treatment according to any of [13] to [17], wherein an average number of units of the drug-linker structure conjugated per antibody molecule of the antibody-drug conjugate is in a range of 2 to 8.

[19] The pharmaceutical composition for treatment according to any of [13] to [17], wherein an average number of units of the drug-linker structure conjugated per antibody molecule of the antibody-drug conjugate is in a range of 3 to 8.

[20] The pharmaceutical composition for treatment according to any of [13] to [17], wherein an average number of units of the drug-linker structure conjugated per antibody molecule of the antibody-drug conjugate is in a range of 7 to 8.

[21] The pharmaceutical composition for treatment according to any of [13] to [17], wherein an average number of units of the drug-linker structure conjugated per antibody molecule of the antibody-drug conjugate is in a range of 7.5 to 8.

[22] The pharmaceutical composition for treatment according to any of [13] to [21], wherein a dose of the antibody-drug conjugate is in a range of 0.8 mg/kg to 8 mg/kg.

[23] The pharmaceutical composition for treatment according to any of [13] to [21], which is administered once every 3 weeks.

[24] The pharmaceutical composition for treatment according to any of [13] to [23], wherein the resistant cancer is lung cancer, urothelial cancer, colorectal cancer, prostate cancer, ovarian cancer, pancreatic cancer, breast cancer, bladder cancer, gastric cancer, gastrointestinal stromal tumor, uterine cervix cancer, esophageal cancer, squamous cell carcinoma, peritoneal cancer, liver cancer, hepatocellular cancer, colon cancer, rectal cancer, colorectal cancer, endometrial cancer, uterine cancer, salivary gland cancer, kidney cancer, vulval cancer, thyroid cancer, penis cancer, leukemia, malignant lymphoma, plasmacytoma, myeloma, or sarcoma.

[25] A method for treating resistant cancer, comprising administering an antibody-drug conjugate in which a linker and a drug represented by the following formula are conjugated to an anti-HER2 antibody, a salt thereof, or a hydrate thereof:

-(Succinimid-3-yl-N)—$CH_2CH_2CH_2CH_2CH_2$—C(═O)-GGFG-NH—$CH_2$—O—$CH_2$—C(═O)—(NH-DX) ("GGFG" disclosed as SEQ ID NO: 5)

wherein (Succinimid-3-yl-N)- has a structure represented by the following formula:

[Formula 16]

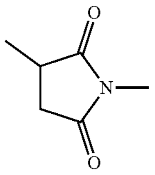

which is connected to the anti-HER2 antibody at position 3 thereof via a thioether bond and is connected to the methylene group in the linker structure containing this structure on the nitrogen atom at position 1, and (NH-DX) represents a group represented by the following formula:

[Formula 17]

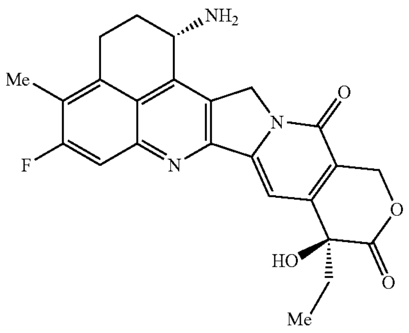

wherein the nitrogen atom of the amino group at position 1 is the connecting position.

[26] The treatment method according to [25], wherein the resistant cancer is secondary resistant cancer.

[27] The treatment method according to [26], wherein the secondary resistance is secondary resistance caused by the administration of an antibody-drug conjugate comprising an anti-HER2 antibody.

[28] The treatment method according to [26] or [27], wherein the secondary resistance is secondary resistance acquired by the administration of T-DM1 which is an anti-HER2 antibody-drug conjugate.

[29] The treatment method according to [26], wherein the secondary resistance is secondary resistance caused by the administration of an anti-HER2 antibody.

[30] The treatment method according to any of [25] to [29], wherein an average number of units of the drug-linker structure conjugated per antibody molecule of the antibody-drug conjugate is in a range of 2 to 8.

[31] The treatment method according to any of [25] to [29], wherein an average number of units of the drug-linker structure conjugated per antibody molecule of the antibody-drug conjugate is in a range of 3 to 8.

[32] The treatment method according to any of [25] to [29], wherein an average number of units of the drug-linker structure conjugated per antibody molecule of the antibody-drug conjugate is in a range of 7 to 8.

[33] The treatment method according to any of [25] to [29], wherein an average number of units of the drug-linker structure conjugated per antibody molecule of the antibody-drug conjugate is in a range of 7.5 to 8.

[34] The treatment method according to any of [25] to [33], wherein a dose of the antibody-drug conjugate is in a range of 0.8 mg/kg to 8 mg/kg.

[35] The treatment method according to any of [25] to [34], wherein the antibody-drug conjugate is administered once every 3 weeks.

[36] The treatment method according to any of [25] to [35], wherein the resistant cancer is lung cancer, urothelial cancer, colorectal cancer, prostate cancer, ovarian cancer, pancreatic cancer, breast cancer, bladder cancer, gastric cancer, gastrointestinal stromal tumor, uterine cervix cancer, esophageal cancer, squamous cell carcinoma, peritoneal cancer, liver cancer, hepatocellular cancer, colon cancer, rectal cancer, colorectal cancer, endometrial cancer, uterine cancer, salivary gland cancer, kidney cancer, vulval cancer, thyroid cancer, penis cancer, leukemia, malignant lymphoma, plasmacytoma, myeloma, or sarcoma.

[37] A pharmaceutical composition for treatment comprising an antibody-drug conjugate in which a linker and a drug represented by the following formula are conjugated to an anti-HER2 antibody, a salt thereof, or a hydrate thereof as an active component, and a pharmaceutically acceptable formulation component, and being applied to a patient with cancer that exhibits resistance to an anticancer drug:

-(Succinimid-3-yl-N)—$CH_2CH_2CH_2CH_2CH_2$—C(═O)-GGFG-NH—$CH_2$—O—$CH_2$—C(═O)—(NH-DX) ("GGFG" disclosed as SEQ ID NO: 5)

wherein (Succinimid-3-yl-N)- has a structure represented by the following formula:

[Formula 18]

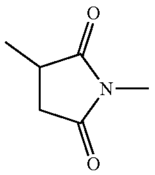

which is connected to the anti-HER2 antibody at position 3 thereof via a thioether bond and is connected to the methylene group in the linker structure containing this structure on the nitrogen atom at position 1, and (NH-DX) represents a group represented by the following formula:

[Formula 19]

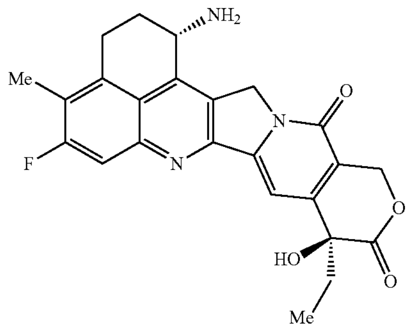

wherein the nitrogen atom of the amino group at position 1 is the connecting position.

[38] The pharmaceutical composition for treatment according to [37], which is applied to a cancer patient having a history of treatment with the anticancer drug.

[39] The pharmaceutical composition for treatment according to [37] or [38], which is used instead of or in combination with an additional anticancer drug.

[40] The pharmaceutical composition for treatment according to any of [37] to [39], wherein the resistance to an anticancer drug is secondary resistance.

[41] The pharmaceutical composition for treatment according to any of [37] to [40], wherein the anticancer drug is an antibody-drug conjugate comprising an anti-HER2 antibody.

[42] The pharmaceutical composition for treatment according to [41], wherein the anticancer drug is trastuzumab emtansine (T-DM1).

[43] The pharmaceutical composition for treatment according to any of [37] to [40], wherein the anticancer drug is an anti-HER2 antibody.

[44] The pharmaceutical composition for treatment according to any of [37] to [43], wherein an average number of units of the drug-linker structure conjugated per antibody molecule of the antibody-drug conjugate is in a range of 2 to 8.

[45] The pharmaceutical composition for treatment according to any of [37] to [43], wherein an average number of units of the drug-linker structure conjugated per antibody molecule of the antibody-drug conjugate is in a range of 3 to 8.

[46] The pharmaceutical composition for treatment according to any of [37] to [43], wherein an average number of units of the drug-linker structure conjugated per antibody molecule of the antibody-drug conjugate is in a range of 7 to 8.

[47] The pharmaceutical composition for treatment according to any of [37] to [43], wherein an average number of units of the drug-linker structure conjugated per antibody molecule of the antibody-drug conjugate is in a range of 7.5 to 8.

[48] The pharmaceutical composition for treatment according to any of [37] to [47], wherein a dose of the antibody-drug conjugate is in a range of 0.8 mg/kg to 8 mg/kg.

[49] The pharmaceutical composition for treatment according to any of [37] to [48], which is administered once every 3 weeks.

[50] The pharmaceutical composition for treatment according to any of [37] to [49], wherein the resistant cancer is lung cancer, urothelial cancer, colorectal cancer, prostate cancer, ovarian cancer, pancreatic cancer, breast cancer, bladder cancer, gastric cancer, gastrointestinal stromal tumor, uterine cervix cancer, esophageal cancer, squamous cell carcinoma, peritoneal cancer, liver cancer, hepatocellular cancer, colon cancer, rectal cancer, colorectal cancer, endometrial cancer, uterine cancer, salivary gland cancer, kidney cancer, vulval cancer, thyroid cancer, penis cancer, leukemia, malignant lymphoma, plasmacytoma, myeloma, or sarcoma.

Advantageous Effects of Invention

The therapeutic agent comprising an antibody-drug conjugate, used in the present invention exhibits an excellent antitumor effect on HER2-expressing cancer having resistance or refractoriness to an existing anti-HER2 drug and exhibits a high antitumor effect even on secondary resistant cancer. The therapeutic agent has also favorable safety profile and can therefor provide an effective treatment method.

BRIEF DESCRIPTION OF DRAWINGS

FIG. 1 shows an amino acid sequence of a heavy chain of a humanized anti-HER2 monoclonal antibody (SEQ ID NO: 1).

FIG. 2 shows an amino acid sequence of a light chain of a humanized anti-HER2 monoclonal antibody (SEQ ID NO: 2).

DESCRIPTION OF EMBODIMENTS

Figure 3:
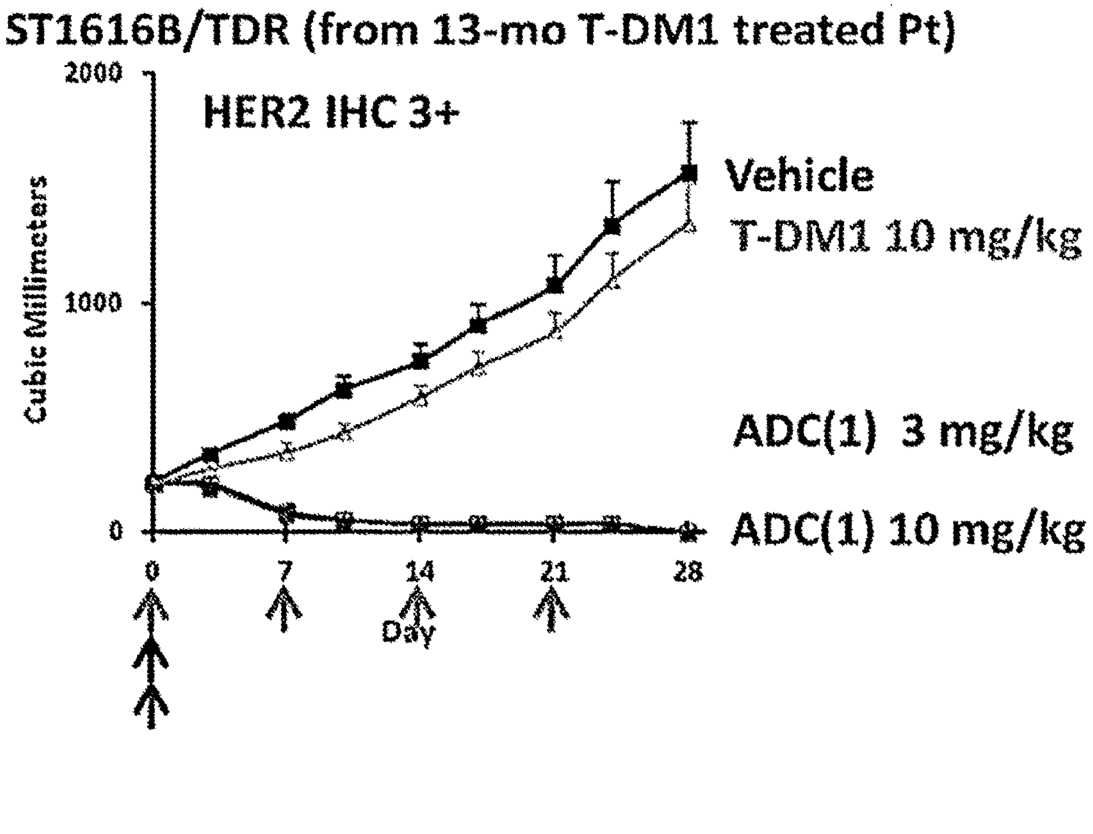
FIG. 3 is a diagram showing the antitumor effect of an antibody-drug conjugate (1) or T-DM1 on a nude mouse with subcutaneously transplanted tumor of HER2-positive human breast cancer ST1616B/TDR that acquired secondary resistance to T-DM1. In the drawing, the abscissa depicts days after initial administration, and the ordinate depicts tumor volume.

Hereinafter, preferred modes for carrying out the present invention are described with reference to the drawings. The embodiments described below are given merely for illustrating one example of a typical embodiment of the present invention and are not intended to limit the scope of the present invention.

The antibody-drug conjugate used in the present invention is an anti-HER2 antibody-drug conjugate in which a linker and a drug represented by the following formula are connected to an anti-HER2 antibody.

-(Succinimid-3-yl-N)—$CH_2CH_2CH_2CH_2CH_2$—C(=O)-GGFG-NH—$CH_2$—O—$CH_2$—C(=O)—(NH-DX) ("GGFG" disclosed as SEQ ID NO: 5)

In the formula, -(Succinimid-3-yl-N)- has a structure represented by the following formula:

[Formula 20]

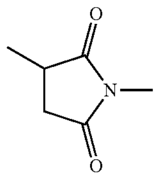

which is connected to the anti-HER2 antibody at position 3 thereof via a thioether bond and is connected to the methylene group in the linker structure containing this structure on the nitrogen atom at position 1.

-(NH-DX) is a group represented by the following formula:

[Formula 21]

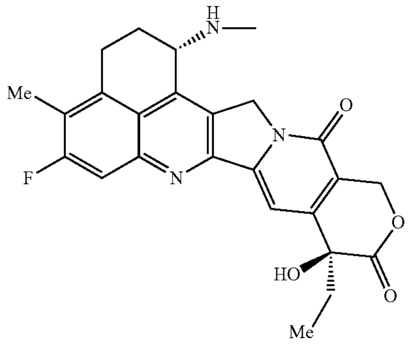

wherein the nitrogen atom of the amino group at position 1 is the connecting position.

-GGFG- represents the tetrapeptide residue of -Gly-Gly-Phe-Gly- (SEQ ID NO: 5).

In this specification, a partial structure consisting of the linker and the drug in the antibody-drug conjugate is referred to as a "drug-linker structure". This drug-linker structure is connected to a thiol group (in other words, the sulfur atom of a cysteine residue) formed at the interchain disulfide bond sites (2 sites between the heavy chain and the heavy chain, and 2 sites between the heavy chain and the light chain) of the antibody.

The anti-HER2 antibody-drug conjugate used in the present invention can have a structure represented by the following formula:

[Formula 22]

Anti-HER2 antibody

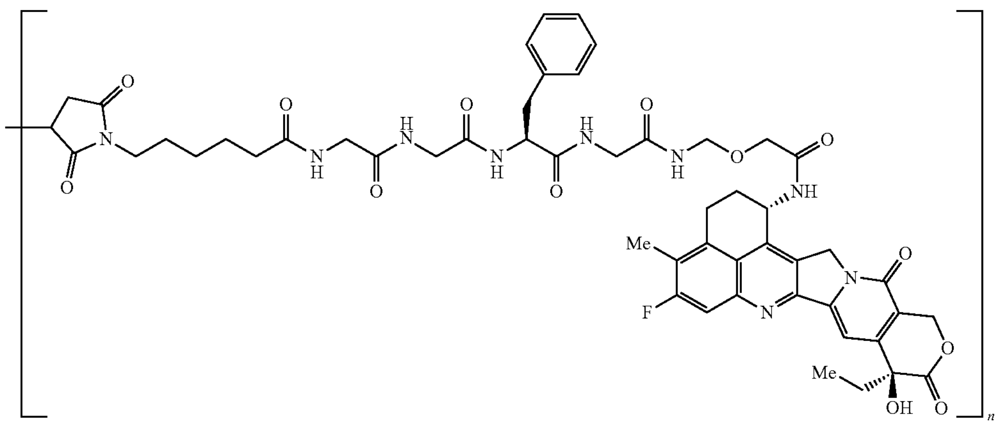

Here, the drug-linker structure is conjugated to the anti-HER2 antibody via a thioether bond. Furthermore, n has the same meaning as DAR (drug-to-antibody ratio) and represents the number of conjugated drug molecules per antibody molecule. DAR is an average value, i.e., a numeric value defined and indicated as the average number of conjugated drug molecules. In the case of the antibody-drug conjugate of the present invention, n is 2 to 8, preferably 3 to 8, more preferably 7 to 8, and further preferably 7.5 to 8, and n of about 8 can be preferably used.

Hereinafter, the antibody-drug conjugate used in the present invention is explained in detail hereinbelow.

[Antibody]

The anti-HER2 antibody used in the anti-HER2 antibody-drug conjugate used in the present invention may be derived from any species, and preferred examples of the species can include humans, rats, mice, and rabbits. In case when the antibody is derived from other than human species, it is preferably chimerized or humanized using a well known technique. The antibody of the present invention may be a polyclonal antibody or a monoclonal antibody and is preferably a monoclonal antibody.

The anti-HER2 antibody is the antibody, which is capable of targeting tumor cells, that is, possesses a property of recognizing a tumor cell, a property of binding to a tumor cell, a property of internalizing in a tumor cell, cytocidal activity against tumor cells, or the like, and can be conjugated with a drug having antitumor activity via a linker to form an antibody-drug conjugate.

The binding activity of the antibody against tumor cells can be confirmed using flow cytometry. The internalization of the antibody into tumor cells can be confirmed using (1) an assay of visualizing an antibody incorporated in cells under a fluorescence microscope using a secondary antibody (fluorescently labeled) binding to the therapeutic antibody (Cell Death and Differentiation (2008) 15, 751-761), (2) an assay of measuring a fluorescence intensity incorporated in cells using a secondary antibody (fluorescently labeled) binding to the therapeutic antibody (Molecular Biology of the Cell, Vol. 15, 5268-5282, December 2004), or (3) a Mab-ZAP assay using an immunotoxin binding to the therapeutic antibody wherein the toxin is released upon incorporation into cells to inhibit cell growth (Bio Techniques 28: 162-165, January 2000). As the immunotoxin, a recombinant complex protein of a diphtheria toxin catalytic domain and protein G may be used.

The antitumor activity of the antibody can be confirmed in vitro by determining inhibitory activity against cell growth. For example, a cancer cell line overexpressing a target protein for the antibody is cultured, and the antibody is added at varying concentrations into the culture system to determine an inhibitory activity against focus formation, colony formation, and spheroid growth. The antitumor activity can be confirmed in vivo, for example, by administering the antibody to a nude mouse with a transplanted tumor cell line highly expressing the target protein, and determining change in the cancer cell.

Since the compound conjugated in the antibody-drug conjugate exerts an antitumor effect, it is preferred but not essential that the antibody itself should have an antitumor effect. For the purpose of specifically and selectively exerting the cytotoxic activity of the antitumor compound against tumor cells, it is important and also preferred that the antibody should have the property of internalizing to migrate into tumor cells.

The anti-HER2 antibody can be obtained by a procedure known in the art. For example, the antibody of the present invention can be obtained using a method usually carried out in the art, which involves immunizing animals with an antigenic polypeptide and collecting and purifying antibodies produced in vivo. The origin of the antigen is not limited to humans, and the animals may be immunized with an antigen derived from a non-human animal such as a mouse, a rat and the like. In this case, the cross-reactivity of antibodies binding to the obtained heterologous antigen with human antigens can be tested to screen for an antibody applicable to a human disease.

Alternatively, antibody-producing cells which produce antibodies against the antigen are fused with myeloma cells according to a method known in the art (e.g., Kohler and Milstein, Nature (1975) 256, p. 495-497; and Kennet, R. ed., Monoclonal Antibodies, p. 365-367, Plenum Press, N.Y. (1980)) to establish hybridomas, from which monoclonal antibodies can in turn be obtained.

The antigen can be obtained by genetically engineering host cells to produce a gene encoding the antigenic protein. Specifically, vectors that permit expression of the antigen gene are prepared and transferred to host cells so that the gene is expressed. The antigen thus expressed can be purified. The antibody can also be obtained by a method of immunizing animals with the above-described genetically engineered antigen-expressing cells or a cell line expressing the antigen.

The anti-HER2 antibodies that can be used in the present invention are not particularly limited and are preferably, for example, those having properties as described below.

(1) An anti-HER2 antibody having the following properties:
(a) specifically binding to HER2, and
(b) having an activity of internalizing in HER2-expressing cells by binding to HER2.

(2) The antibody according to (1) above, wherein the antibody binds to the extracellular domain of HER2.

(3) The antibody according to (1) or (2) above, wherein the antibody is a monoclonal antibody.

(4) The antibody according to any of (1) to (3) above, wherein the antibody has an antibody-dependent cellular cytotoxicity (ADCC) activity and/or a complement-dependent cytotoxicity (CDC) activity (5) The antibody according to any of (1) to (4) above, wherein the antibody is a mouse monoclonal antibody, a chimeric monoclonal antibody, or a humanized monoclonal antibody.

(6) The antibody according to any of (1) to (5) above, wherein the antibody is a humanized monoclonal antibody comprising a heavy chain consisting of the amino acid sequence represented by SEQ ID NO: 1 and a light chain consisting of the amino acid sequence represented by SEQ ID NO: 2.

(7) The antibody according to any of (1) to (6) above, wherein the antibody lacks a lysine residue at the carboxyl terminus of the heavy chain.

(8) The antibody according to (7) above, wherein the antibody comprises a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

(9) An antibody obtained by a method for producing the antibody according to any of (1) to (8) above, the method comprising the steps of: culturing a host cell transformed with an expression vector containing a polynucleotide encoding the antibody; and collecting the antibody of interest from the cultures obtained in the preceding step.

Hereinafter, the anti-HER2 antibody used in the invention is described.

The terms "cancer" and "tumor" as used herein are used with the same meaning.

The term "gene" as used herein includes not only DNA, but also mRNA thereof, cDNA thereof and cRNA thereof.

The term "polynucleotide" as used herein is used with the same meaning as a nucleic acid and also includes DNA, RNA, probes, oligonucleotides, and primers.

The terms "polypeptide", "protein" and "protein" as used herein are used without distinction.

The term "cell" as used herein also includes cells in an animal individual and cultured cells.

The term "HER2" as used herein is used with the same meaning as HER2 protein.

Examples of the anti-HER2 antibody as used herein can include, but not particularly limited to, pertuzumab (International Patent Publication No. WO 01/00245) and trastuzumab (U.S. Pat. No. 5,821,337). Trastuzumab is preferred. However, the anti-HER2 antibody of the present invention is not limited thereto as long as it is an anti-HER2 antibody specifically binding to HER2, and more preferably having an activity of internalizing in HER2-expressing cells by binding to HER2.

The term "trastuzumab" as used herein is also called HERCEPTIN (registered trademark), huMAb4D5-8, or rhuMAb4D5-8 and is a humanized antibody comprising a heavy chain consisting of an amino acid sequence consisting of amino acid residues 1 to 449 of SEQ ID NO: 1 (FIG. 1) and a light chain consisting of an amino acid sequence consisting of amino acid residues 1 to 214 of SEQ ID NO: 2 (FIG. 2).

The term "specifically binding" as used herein means binding that is not nonspecific adsorption. Examples of the criterion for determining whether the binding is specific or not can include dissociation constant (hereinafter referred to as "Kd"). The Kd value of the antibody for the HER2 protein is preferably $1\times10^{-3}$ M or smaller, $5\times10^{-6}$ M or smaller, $2\times10^{-6}$ M or smaller, or $1\times10^{-6}$ M or smaller, more preferably $5\times10^{-7}$ M or smaller, $2\times10^{-7}$ M or smaller, or $1\times10^{-7}$ M or smaller, further preferably $5\times10^{-8}$ M or smaller, $2\times10^{-8}$ M or smaller, or $1\times10^{-8}$ M or smaller, and most preferably $5\times10^{-9}$ M or smaller, $2\times10^{-9}$ M or smaller, or $1\times10^{-9}$ M or smaller. The binding between the HER2 protein and the antibody can be measured using a method known in the art, such as surface plasmon resonance, ELISA, or RIA.

The term "CDR" as used herein refers to a complementarity determining region (CDR). It is known that each heavy and light chain of an antibody molecule has three complementarity determining regions (CDRs). The CDR is also called the hypervariable domain, and is present in a variable region of each heavy and light chain of an antibody. It is a site which has unusually high variability in its primary structure, and there are three separate CDRs in the primary structure of each heavy and light polypeptide chain. In this specification, as for the CDRs of an antibody, the CDRs of the heavy chain are represented by CDRH1, CDRH2, and CDRH3 from the amino-terminal side of the amino acid sequence of the heavy chain, and the CDRs of the light chain are represented by CDRL1, CDRL2, and CDRL3 from the amino-terminal side of the amino acid sequence of the light chain. These sites are proximate to one another in the tertiary structure and determine the specificity for an antigen to which the antibody binds.

The phrase "hybridization is performed under stringent conditions" as used herein refers to a process in which hybridization is performed under conditions under which identification can be achieved by performing hybridization at 68° C. in a commercially available hybridization solution ExpressHyb Hybridization Solution (manufactured by Clontech, Inc.) or by performing hybridization at 68° C. in the presence of 0.7 to 1.0 M NaCl using a filter having DNA immobilized thereon, followed by performing washing at 68° C. using 0.1 to 2×SSC solution (1×SSC solution is composed of 150 mM NaCl and 15 mM sodium citrate) or under conditions equivalent thereto.

1. HER2

HER2 is one of the oncogene products of a typical growth factor receptor oncogene identified as human epidermal cell growth factor receptor 2-related oncogene, and is a transmembrane receptor protein having a molecular weight of 185 kDa and having a tyrosine kinase domain. HER2 is a member of the EGFR family consisting of HER1 (EGFR, ErbB-1), HER2 (neu, ErbB-2), HER3 (ErbB-3), and HER4 (ErbB-4) and is known to be autophosphorylated at intracellular tyrosine residues by its homodimer formation or heterodimer formation with another EGFR receptor HER1, HER3, or HER4 and is itself activated in that manner, thereby playing an important role in cell growth, differentiation, and survival in normal cells and tumor cells.

As for the HER2 protein to be used in the present invention, the HER2 protein can be directly purified from HER2-expressing cells of a human or a non-human mammal (such as a rat or a mouse) and used, or a cell membrane fraction of the above-described cells can be prepared and used. Further, HER2 can be obtained by in vitro synthesis thereof or production thereof in a host cell through genetic engineering. In the genetic engineering, specifically, after HER2 cDNA is integrated into a vector capable of expressing HER2 cDNA, the HER2 protein can be obtained by synthesizing it in a solution containing an enzyme, a substrate and an energy substance required for transcription and translation, or by expressing HER2 in another prokaryotic or eucaryotic transformed host cell. Alternatively, the above-described genetically engineered HER2-expressing cells, or a cell line expressing HER2 may be used as the HER2 protein.

The DNA sequence and amino acid sequence of HER2 are disclosed on a public database, and can be referred to, for example, under Accession No. M11730 (GenBank), NP_004439.2 (NCBI), or the like.

Further, a protein which consists of an amino acid sequence wherein one or several amino acids are substituted, deleted and/or added in any of the above-described amino acid sequences of HER2 and also has a biological activity equivalent to that of the protein is also included in HER2.

Human HER2 protein is composed of a signal sequence consisting of N-terminal 22 amino acid residues, an extracellular domain consisting of 630 amino acid residues, a transmembrane domain consisting of 23 amino acid residues, and an intracellular domain consisting of 580 amino acid residues.

2. Production of Anti-HER2 Antibody

The antibody against HER2 of the present invention can be obtained according to, for example, a method usually carried out in the art, which involves immunizing animals with HER2 or an arbitrary polypeptide selected from the amino acid sequence of HER2 and collecting and purifying antibodies produced in vivo. The biological species of HER2 to be used as an antigen is not limited to being human, and an animal can be immunized with HER2 derived from an animal other than humans such as a mouse or a rat or with rat p185neu. In this case, by examining the cross-reactivity between an antibody binding to the obtained heterologous HER2 and human HER2, an antibody applicable to a human disease can be selected.

Further, a monoclonal antibody can be obtained from a hybridoma established by fusing antibody-producing cells which produce an antibody against HER2 with myeloma cells according to a known method (for example, Kohler and Milstein, Nature, (1975) 256, pp. 495-497; Kennet, R. ed., Monoclonal Antibodies, pp. 365-367, Plenum Press, N.Y. (1980)).

HER2 to be used as an antigen can be obtained by expressing HER2 gene in a host cell using genetic engineering.

Specifically, a vector capable of expressing HER2 gene is produced, and the resulting vector is transfected into a host cell to express the gene, and then, the expressed HER2 is purified.

Alternatively, the above-described genetically engineered HER2-expressing cells, or a cell line expressing HER2 may be used as the HER2 protein. The anti-HER2 antibody can be obtained by a procedure known in the art. Hereinafter, a method of obtaining an antibody against HER2 is specifically described.

(1) Preparation of Antigen

Examples of the antigen to be used for producing the anti-HER2 antibody include HER2, or a polypeptide consisting of a partial amino acid sequence comprising at least 6 consecutive amino acids of HER2, or a derivative obtained by adding a given amino acid sequence or carrier thereto.

HER2 can be purified directly from human tumor tissues or tumor cells and used. Further, HER2 can be obtained by synthesizing it in vitro or by producing it in a host cell by genetic engineering.

With respect to the genetic engineering, specifically, after HER2 cDNA is integrated into a vector capable of expressing HER2 cDNA, HER2 can be obtained by synthesizing it in a solution containing an enzyme, a substrate and an energy substance required for transcription and translation, or by expressing HER2 in another prokaryotic or eucaryotic transformed host cell.

Further, the antigen can also be obtained as a secretory protein by expressing a fusion protein obtained by ligating the extracellular domain of HER2, which is a membrane protein, to the constant region of an antibody in an appropriate host-vector system.

HER2 cDNA can be obtained by, for example, a so-called PCR method in which a polymerase chain reaction is performed using a cDNA library expressing HER2 cDNA as a template and primers which specifically amplify HER2 cDNA (PCR; Saiki, R. K., et al., Science, (1988) 239, pp. 487-489).

As the in vitro synthesis of the polypeptide, for example, Rapid Translation System (RTS) manufactured by Roche Diagnostics, Inc. can be exemplified, but it is not limited thereto.

Examples of the prokaryotic host cells include *Escherichia coli* and *Bacillus subtilis*. In order to transform the host cells with a target gene, the host cells are transformed by a plasmid vector comprising a replicon, i.e., a replication origin derived from a species compatible with the host, and a regulatory sequence. Further, the vector preferably has a sequence capable of imposing phenotypic selectivity on the transformed cell.

Examples of the eucaryotic host cells include vertebrate cells, insect cells, and yeast cells. As the vertebrate cells, for example, simian COS cells (Gluzman, Y., Cell, (1981) 23, pp. 175-182, ATCC CRL-1650; ATCC: American Type Culture Collection), murine fibroblasts NIH3T3 (ATCC No. CRL-1658), and dihydrofolate reductase-deficient strains (Urlaub, G. and Chasin, L. A., Proc. Natl. Acad. Sci. USA (1980) 77, pp. 4126-4220) of Chinese hamster ovarian cells (CHO cells; ATCC: CCL-61); and the like are often used, however, the cells are not limited thereto.

The thus obtained transformant can be cultured according to a method usually carried out in the art, and by the culturing of the transformant, a target polypeptide is produced intracellularly or extracellularly.

A suitable medium to be used for the culturing can be selected from various commonly used culture media depending on the employed host cells. If *Escherichia coli* is employed, for example, an LB medium supplemented with an antibiotic such as ampicillin or IPMG as needed can be used.

A recombinant protein produced intracellularly or extracellularly by the transformant through such culturing can be separated and purified by any of various known separation methods utilizing the physical or chemical property of the protein.

Specific examples of the methods include treatment with a common protein precipitant, ultrafiltration, various types of liquid chromatography such as molecular sieve chromatography (gel filtration), adsorption chromatography, ion exchange chromatography, and affinity chromatography, dialysis, and a combination thereof.

Further, by attaching a tag of six histidine residues (SEQ ID NO: 13) to a recombinant protein to be expressed, the protein can be efficiently purified with a nickel affinity column. Alternatively, by attaching the IgG Fc region to a recombinant protein to be expressed, the protein can be efficiently purified with a protein A column.

By combining the above-described methods, a large amount of a target polypeptide can be easily produced in high yield and high purity.

The above-described transformant itself may be used as the antigen. A cell line expressing HER2 may also be used as the antigen. Examples of such a cell line can include human breast cancer lines SK-BR-3, BT-474, KPL-4, and JIMT-1, a human gastric cancer line NCI-N87, and a human ovarian cancer line SK-OV-3. The cell line of the present invention is not limited to these cell lines as long as it expresses HER2.

(2) Production of Anti-HER2 Monoclonal Antibody

Examples of the antibody specifically bind to HER2 include a monoclonal antibody specifically bind to HER2, and a method of obtaining such antibody is as described below.

The production of a monoclonal antibody generally requires the following operational steps of:

(a) purifying a biopolymer to be used as an antigen, or preparing antigen-expressing cells;

(b) preparing antibody-producing cells by immunizing an animal by injection of the antigen, collecting the blood, assaying its antibody titer to determine when the spleen is excised;

(c) preparing myeloma cells (hereinafter referred to as "myeloma");

(d) fusing the antibody-producing cells with the myeloma;

(e) screening a group of hybridomas producing a desired antibody;

(f) dividing the hybridomas into single cell clones (cloning);

(g) optionally, culturing the hybridoma or rearing an animal implanted with the hybridoma for producing a large amount of monoclonal antibody;

(h) examining the thus produced monoclonal antibody for biological activity and binding specificity, or assaying the same for properties as a labeled reagent; and the like.

Hereinafter, the method of producing a monoclonal antibody will be described in detail following the above steps, however, the method is not limited thereto, and, for example, antibody-producing cells other than spleen cells and myeloma can be used.

(a) Purification of Antigen

As the antigen, HER2 prepared by the method as described above or a partial peptide thereof can be used.

Further, a membrane fraction prepared from recombinant cells expressing HER2 or the recombinant cells expressing HER2 themselves, and also a partial peptide of the protein of the present invention chemically synthesized by a method known to those skilled in the art can also be used as the antigen.

Furthermore, a HER2-expressing cell line can also be used as the antigen.

(b) Preparation of Antibody-Producing Cells

The antigen obtained in the step (a) is mixed with an adjuvant such as Freund's complete or incomplete adjuvant or auxiliary agent such as aluminum potassium sulfate and the resulting mixture is used as an immunogen to immunize an experimental animal. Another method involves immunizing an experimental animal with antigen-expressing cells as an immunogen. As the experimental animal, any animal used in a known hybridoma production method can be used without hindrance. Specifically, for example, a mouse, a rat, a goat, sheep, cattle, a horse, or the like can be used. However, from the viewpoint of ease of availability of myeloma cells to be fused with the extracted antibody-producing cells, a mouse or a rat is preferably used as the animal to be immunized.

Further, the strain of a mouse or a rat to be used is not particularly limited, and in the case of a mouse, for example, various strains such as A, AKR, BALB/c, BDP, BA, CE, C3H, 57BL, C57BL, C57L, DBA, FL, HTH, HT1, LP, NZB, NZW, RF, R III, SJL, SWR, WB, and 129 and the like can be used, and in the case of a rat, for example, Wistar, Low, Lewis, Sprague, Dawley, ACI, BN, Fischer and the like can be used.

These mice and rats are commercially available from breeders/distributors of experimental animals, for example, CLEA Japan, Inc. and Charles River Laboratories Japan, Inc.

As the animal to be immunized, in consideration of compatibility of fusing with myeloma cells described below, in the case of a mouse, BALB/c strain, and in the case of a rat, Wistar and Low strains are particularly preferred.

Further, in consideration of antigenic homology between humans and mice, it is also preferred to use a mouse having decreased biological function to remove auto-antibodies, that is, a mouse with an autoimmune disease.

The age of such mouse or rat at the time of immunization is preferably 5 to 12 weeks of age, more preferably 6 to 8 weeks of age.

In order to immunize an animal with HER2 or a recombinant thereof, for example, a known method described in detail in, for example, Weir, D. M., Handbook of Experimental Immunology Vol. I. II. III., Blackwell Scientific Publications, Oxford (1987); Kabat, E. A. and Mayer, M. M., Experimental Immunochemistry, Charles C Thomas Publisher Springfield, Illinois (1964) or the like can be used.

Among these immunization methods, a preferred specific method in the present invention is, for example, as follows.

That is, first, a membrane protein fraction serving as the antigen or cells caused to express the antigen is/are intradermally or intraperitoneally administrated to an animal. However, the combination of both routes of administration is preferred for increasing the immunization efficiency, and when intradermal administration is performed in the first half and intraperitoneal administration is performed in the latter half or only at the last dosing, the immunization efficiency can be particularly increased.

The administration schedule of the antigen varies depending on the type of animal to be immunized, individual difference or the like. However, in general, an administration schedule in which the frequency of administration of the antigen is 3 to 6 times and the dosing interval is 2 to 6 weeks is preferred, and an administration schedule in which the frequency of administration of the antigen is 3 to 4 times and the dosing interval is 2 to 4 weeks is more preferred.

Further, the dose of the antigen varies depending on the type of animal, individual differences or the like, however, the dose is generally set to 0.05 to 5 mg, preferably about 0.1 to 0.5 mg.

A booster immunization is performed 1 to 6 weeks, preferably 1 to 4 weeks, more preferably 1 to 3 weeks after the administration of the antigen as described above. When the immunogen is cells, $1\times10^6$ to $1\times10^7$ cells are used.

The dose of the antigen at the time of performing the booster immunization varies depending on the type or size of animal or the like, however, in the case of, for example, a mouse, the dose is generally set to 0.05 to 5 mg, preferably 0.1 to 0.5 mg, more preferably about 0.1 to 0.2 mg. When the immunogen is cells, $1\times10^6$ to $1\times10^7$ cells are used.

Spleen cells or lymphocytes including antibody-producing cells are aseptically removed from the immunized animal after 1 to 10 days, preferably 2 to 5 days, more preferably 2 to 3 days from the booster immunization. At this time, the antibody titer is measured, and if an animal having a sufficiently increased antibody titer is used as a supply source of the antibody-producing cells, the subsequent procedure can be carried out more efficiently.

Examples of the method of measuring the antibody titer to be used here include an RIA method and an ELISA method, but the method is not limited thereto. For example, if an ELISA method is employed, the measurement of the antibody titer in the invention can be carried out according to the procedures as described below.

First, a purified or partially purified antigen is adsorbed to the surface of a solid phase such as a 96-well plate for ELISA, and the surface of the solid phase having no antigen adsorbed thereto is covered with a protein unrelated to the antigen such as bovine serum albumin (BSA). After washing the surface, the surface is brought into contact with a serially-diluted sample (for example, mouse serum) as a primary antibody to allow the antibody in the sample to bind to the antigen.

Further, as a secondary antibody, an antibody labeled with an enzyme against a mouse antibody is added and is allowed to bind to the mouse antibody. After washing, a substrate for the enzyme is added and a change in absorbance which occurs due to color development induced by degradation of the substrate or the like is measured and the antibody titer is calculated based on the measurement.

The separation of the antibody-producing cells from the spleen cells or lymphocytes of the immunized animal can be carried out according to a known method (for example, Kohler et al., Nature (1975), 256, p. 495; Kohler et al., Eur. J. Immunol. (1977), 6, p. 511; Milstein et al., Nature (1977), 266, p. 550; Walsh, Nature (1977), 266, p. 495). For example, in the case of spleen cells, a general method in which the antibody-producing cells are separated by homogenizing the spleen to obtain the cells through filtration with a stainless steel mesh and suspending the cells in Eagle's Minimum Essential Medium (MEM) can be employed.

(c) Preparation of Myeloma Cells (Hereinafter Referred to as "Myeloma")

The myeloma cells to be used for cell fusion are not particularly limited and suitable cells can be selected from known cell lines. However, in consideration of convenience when a hybridoma is selected from fused cells, it is preferred to use an HGPRT (hypoxanthine-guanine phosphoribosyl transferase) deficient strain whose selection procedure has been established.

More specifically, examples of the HGPRT-deficient strain include X63-Ag8(X63), NS1-ANS/1(NS1), P3X63-Ag8.U1(P3U1), X63-Ag8.653(X63.653), SP2/0-Ag14(SP2/0), MPC11-45.6TG1.7(45.6TG), FO, 5149/5XXO, and BU.1 derived from mice; 210.RSY3.Ag.1.2.3(Y3) derived from rats; and U266AR(SKO-007), GM1500•GTG-A12 (GM1500), UC729-6, LICR-LOW-HMy2(HMy2) and 8226AR/NIP4-1(NP41) derived from humans. These HGPRT-deficient strains are available from, for example, ATCC or the like.

These cell strains are subcultured in an appropriate medium such as an 8-azaguanine medium [a medium obtained by adding 8-azaguanine to an RPMI 1640 medium supplemented with glutamine, 2-mercaptoethanol, gentamicin, and fetal calf serum (hereinafter referred to as "FCS")], Iscove's Modified Dulbecco's Medium (hereinafter referred to as "IMDM"), or Dulbecco's Modified Eagle Medium (hereinafter referred to as "DMEM"). In this case, 3 to 4 days before performing cell fusion, the cells are subcultured in a normal medium (for example, an ASF104 medium (manufactured by Ajinomoto Co., Ltd.) containing 10% FCS) to ensure not less than $2\times10^7$ cells on the day of cell fusion.

(d) Cell Fusion

Fusion between the antibody-producing cells and the myeloma cells can be appropriately performed according to a known method (Weir, D. M. Handbook of Experimental Immunology Vol. I. II. III., Blackwell Scientific Publications, Oxford (1987); Kabat, E. A. and Mayer, M. M., Experimental Immunochemistry, Charles C Thomas Publisher, Springfield, Illinois (1964), etc.), under conditions such that the survival rate of cells is not excessively reduced.

As such a method, for example, a chemical method in which the antibody-producing cells and the myeloma cells are mixed in a solution containing a polymer such as polyethylene glycol at a high concentration, a physical method using electric stimulation, or the like can be used. Among these methods, a specific example of the chemical method is as described below.

That is, in the case where polyethylene glycol is used in the solution containing a polymer at a high concentration, the antibody-producing cells and the myeloma cells are mixed in a solution of polyethylene glycol having a molecular weight of 1500 to 6000, more preferably 2000 to 4000 at a temperature of from 30 to 40° C., preferably from 35 to 38° C. for 1 to 10 minutes, preferably 5 to 8 minutes.

(e) Selection of a Group of Hybridomas

The method of selecting hybridomas obtained by the above-described cell fusion is not particularly limited. Usually, an HAT (hypoxanthine, aminopterin, thymidine) selection method (Kohler et al., Nature (1975), 256, p. 495; Milstein et al., Nature (1977), 266, p. 550) is used.

This method is effective when hybridomas are obtained using the myeloma cells of an HGPRT-deficient strain which cannot survive in the presence of aminopterin. That is, by culturing unfused cells and hybridomas in an HAT medium, only hybridomas resistant to aminopterin are selectively allowed to survive and proliferate.

(f) Division into Single Cell Clone (Cloning)

As a cloning method for hybridomas, a known method such as a methylcellulose method, a soft agarose method, or a limiting dilution method can be used (see, for example, Barbara, B. M. and Stanley, M. S.: Selected Methods in Cellular Immunology, W. H. Freeman and Company, San Francisco (1980)). Among these methods, particularly, a three-dimensional culture method such as a methylcellulose method is preferred. For example, the group of hybridomas produced by cell fusion are suspended in a methylcellulose medium such as ClonaCell-HY Selection Medium D (manufactured by StemCell Technologies, Inc., #03804) and cultured. Then, the formed hybridoma colonies are collected, whereby monoclonal hybridomas can be obtained. The collected respective hybridoma colonies are cultured, and a hybridoma which has been confirmed to have a stable antibody titer in an obtained hybridoma culture supernatant is selected as a HER2 monoclonal antibody-producing hybridoma strain.

(g) Preparation of Monoclonal Antibody by Culturing Hybridoma

By culturing the thus selected hybridoma, a monoclonal antibody can be efficiently obtained. However, prior to culturing, it is preferred to perform screening of a hybridoma which produces a target monoclonal antibody.

In such screening, a known method can be employed.

The measurement of the antibody titer in the invention can be carried out by, for example, an ELISA method explained in item (b) described above.

The hybridoma obtained by the method described above can be stored in a frozen state in liquid nitrogen or in a freezer at −80° C. or below.

After completion of cloning, the medium is changed from an HT medium to a normal medium, and the hybridoma is cultured.

Large-scale culture is performed by rotation culture using a large culture bottle or by spinner culture. From the supernatant obtained by the large-scale culture, a monoclonal antibody which specifically binds to the protein of the invention can be obtained by purification using a method known to those skilled in the art such as gel filtration.

Further, the hybridoma is injected into the abdominal cavity of a mouse of the same strain as the hybridoma (for example, the above-described BALB/c) or a Nu/Nu mouse to proliferate the hybridoma, whereby the ascites containing a large amount of the monoclonal antibody of the invention can be obtained.

In the case where the hybridoma is administrated in the abdominal cavity, if a mineral oil such as 2,6,10,14-tetramethyl pentadecane (pristane) is administrated 3 to 7 days prior thereto, a larger amount of the ascites can be obtained.

For example, an immunosuppressant is previously injected into the abdominal cavity of a mouse of the same strain as the hybridoma to inactivate T cells. 20 days thereafter, $10^6$ to $10^7$ hybridoma clone cells are suspended in a serum-free medium (0.5 ml), and the suspension is administrated in the abdominal cavity of the mouse. In general, when the abdomen is expanded and filled with the ascites, the ascites is collected from the mouse. By this method, the monoclonal antibody can be obtained at a concentration which is about 100 times or much higher than that in the culture solution.

The monoclonal antibody obtained by the above-described method can be purified by a method described in, for example, Weir, D. M.: Handbook of Experimental Immunology Vol. I, II, III, Blackwell Scientific Publications, Oxford (1978).

The thus obtained monoclonal antibody has high antigen specificity for HER2. Examples of the monoclonal antibody of the present invention can include, but are not particularly limited to, a mouse monoclonal antibody 4D5 (ATCC CRL 10463).

(h) Assay of Monoclonal Antibody

The isotype and subclass of the thus obtained monoclonal antibody can be determined as follows.

First, examples of the identification method include an Ouchterlony method, an ELISA method, and an RIA method.

An Ouchterlony method is simple, but when the concentration of the monoclonal antibody is low, a condensation operation is required.

On the other hand, when an ELISA method or an RIA method is used, by directly reacting the culture supernatant with an antigen-adsorbed solid phase and using antibodies corresponding to various types of immunoglobulin isotypes and subclasses as secondary antibodies, the isotype and subclass of the monoclonal antibody can be identified.

In addition, as a simpler method, a commercially available identification kit (for example, Mouse Typer Kit manufactured by Bio-Rad Laboratories, Inc.) or the like can also be used.

Further, the quantitative determination of a protein can be performed by the Folin Lowry method and a method of calculation based on the absorbance at 280 nm (1.4 (OD 280)=Immunoglobulin 1 mg/ml).

Further, even when the monoclonal antibody is separately and independently obtained by performing again the steps of (a) to (h) in (2), it is possible to obtain an antibody having a cytotoxic activity equivalent to that of the HER2 antibody obtained in the the step of (g). As one example of such an antibody, an antibody which binds to the same epitope as the HER2 antibody obtained in the step of (g) can be exemplified. If a newly produced monoclonal antibody binds to a partial peptide or a partial tertiary structure to which the anti-HER2 antibody binds, it can be determined that the monoclonal antibody binds to the same epitope as the anti-HER2 antibody. Further, by confirming that the monoclonal antibody competes with the anti-HER2 antibody for the binding to HER2 (that is, the monoclonal antibody inhibits the binding between the anti-HER2 antibody and HER2), it can be determined that the monoclonal antibody binds to the same epitope as the anti-HER2 antibody even if the specific epitope sequence or structure has not been determined. When it is confirmed that the monoclonal antibody binds to the same epitope as the anti-HER2 antibody, the monoclonal antibody is strongly expected to have an antigen-binding affinity or biological activity equivalent to that of the anti-HER2 antibody.

(3) Other Antibodies

The antibody of the invention includes not only the above-described monoclonal antibody against HER2 but also a recombinant antibody obtained by artificial modification for the purpose of decreasing heterologous antigenicity to humans such as a chimeric antibody, a humanized antibody and a human antibody. These antibodies can be produced using a known method.

As the chimeric antibody, an antibody in which antibody variable and constant regions are derived from different species, for example, a chimeric antibody in which a mouse- or rat-derived antibody variable region is connected to a human-derived antibody constant region can be exemplified (see Proc. Natl. Acad. Sci. USA, 81, 6851-6855, (1984)). Examples of the chimeric antibody of the present invention can include, but are not particularly limited to, a chimeric antibody 4D5 comprising a heavy chain constant region of human IgG1 or IgG2.

As the humanized antibody, an antibody obtained by integrating only a complementarity determining region (CDR) of a heterologous antibody into a human-derived antibody (see Nature (1986) 321, pp. 522-525), and an antibody obtained by grafting a part of the amino acid residues of the framework of a heterologous antibody as well as the CDR sequence of the heterologous antibody to a human antibody by a CDR-grafting method (WO 90/07861), and an antibody humanized using gene conversion mutagenesis strategy (U.S. Pat. No. 5,821,337) can be exemplified.

The term "several" as used herein refers to 1 to 10, 1 to 9, 1 to 8, 1 to 7, 1 to 6, 1 to 5, 1 to 4, 1 to 3, or 1 or 2.

As the amino acid substitution in this specification, a conservative amino acid substitution is preferred. The conservative amino acid substitution refers to a substitution occurring within a group of amino acids related to amino acid side chains. Preferred amino acid groups are as follows: an acidic group (aspartic acid and glutamic acid); a basic group (lysine, arginine, and histidine); a non-polar group (alanine, valine, leucine, isoleucine, proline, phenylalanine, methionine, and tryptophan); and an uncharged polar family (glycine, asparagine, glutamine, cysteine, serine, threonine, and tyrosine). More preferred amino acid groups are as follows: an aliphatic hydroxy group (serine and threonine); an amide-containing group (asparagine and glutamine); an aliphatic group (alanine, valine, leucine, and isoleucine); and an aromatic group (phenylalanine, tryptophan, and tyrosine). Such an amino acid substitution is preferably performed within a range which does not impair the properties of a substance having the original amino acid sequence.

By combining a sequence having a high homology with the above-described heavy chain amino acid sequence with a sequence having a high homology with the above-described light chain amino acid sequence, it is possible to select an antibody having a biological activity equivalent to that of each of the above-described antibodies. Such a homology is generally a homology of 80% or more, preferably a homology of 90% or more, more preferably a homology of 95% or more, most preferably a homology of 99% or more. Further, by combining an amino acid sequence wherein one to several amino acid residues are substituted, deleted or added in the heavy chain or light chain amino acid sequence, it is also possible to select an antibody having a biological activity equivalent to that of each of the above-described antibodies. The term "homology" as used herein is used with the same meaning as "identity".

The homology between two amino acid sequences can be determined using default parameters of Blast algorithm version 2.2.2 (Altschul, Stephen F., Thomas L. Madden, Alejandro A. Schaeffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402). The Blast algorithm can be used also through the Internet by accessing the site ncbi.nlm.nih.gov/blast.

Further, the antibody of the invention includes a human antibody which binds to HER2. An anti-HER2 human antibody refers to an anti-HER2 antibody having only a human-derived amino acid sequence. The anti-HER2 human antibody can be obtained by a method using a human antibody-producing mouse having a human chromosome fragment comprising heavy and light chain genes of a human antibody (see Tomizuka, K. et al., Nature Genetics (1997) 16, pp. 133-143; Kuroiwa, Y. et al., Nucl. Acids Res. (1998) 26, pp. 3447-3448; Yoshida, H. et al., Animal Cell Technology: Basic and Applied Aspects vol. 10, pp. 69-73 (Kitagawa, Y., Matuda, T. and Iijima, S. eds.), Kluwer Academic Publishers, 1999; Tomizuka, K. et al., Proc. Natl. Acad. Sci. USA (2000) 97, pp. 722-727, etc.).

Such a human antibody-producing mouse can be created specifically as follows. A genetically modified animal in which endogenous immunoglobulin heavy and light chain gene loci have been disrupted, and instead, human immunoglobulin heavy and light chain gene loci have been introduced via a yeast artificial chromosome (YAC) vector or the like is created by producing a knockout animal and a transgenic animal and mating these animals.

Further, according to a recombinant DNA technique, by using cDNAs encoding each of such a heavy chain and a light chain of a human antibody, and preferably a vector comprising such cDNAs, eukaryotic cells are transformed, and a transformant cell which produces a recombinant human monoclonal antibody is cultured, whereby the antibody can also be obtained from the culture supernatant.

Here, as the host, for example, eukaryotic cells, preferably mammalian cells such as CHO cells, lymphocytes, or myeloma cells can be used.

Further, a method of obtaining a phage display-derived human antibody selected from a human antibody library (see Wormstone, I. M. et al., Investigative Ophthalmology & Visual Science. (2002) 43 (7), pp. 2301-2308; Carmen, S. et al., Briefings in Functional Genomics and Proteomics (2002), 1 (2), pp. 189-203; Siriwardena, D. et al., Ophthalmology (2002) 109 (3), pp. 427-431, etc.) is also known.

For example, a phage display method in which a variable region of a human antibody is expressed on the surface of a phage as a single-chain antibody (scFv), and a phage which binds to an antigen is selected (Nature Biotechnology (2005), 23, (9), pp. 1105-1116) can be used.

By analyzing the gene of the phage selected based on the binding to an antigen, a DNA sequence encoding the variable region of a human antibody which binds to an antigen can be determined.

If the DNA sequence of scFv which binds to an antigen is determined, a human antibody can be obtained by preparing an expression vector comprising the sequence and introducing the vector into an appropriate host to express it (WO 92/01047, WO 92/20791, WO 93/06213, WO 93/11236, WO 93/19172, WO 95/01438, WO 95/15388; Annu. Rev. Immunol. (1994) 12, pp. 433-455, Nature Biotechnology (2005) 23 (9), pp. 1105-1116).

As one example of another index for use in the comparison of the properties of antibodies, the stability of antibodies can be exemplified. The differential scanning calorimetry (DSC) is a device capable of quickly and accurately measuring a thermal denaturation midpoint temperature (Tm) to be used as a favorable index of the relative conformational stability of proteins. By measuring the Tm values using DSC and comparing the values, a difference in thermal stability can be compared. It is known that the storage stability of antibodies shows some correlation with the thermal stability of antibodies (Lori Burton, et. al., Pharmaceutical Development and Technology (2007) 12, pp. 265-273), and a preferred antibody can be selected by using thermal stability as an index. Examples of other indices for selecting antibodies include the following features: the yield in an appropriate host cell is high; and the aggregability in an aqueous solution is low. For example, an antibody which shows the highest yield does not always show the highest thermal stability, and therefore, it is necessary to select an antibody most suitable for the administration to humans by making comprehensive evaluation based on the above-described indices.

A modified variant of the antibody is also included in the antibody used in the present invention. The modified variant refers to a variant obtained by subjecting the antibody of the present invention to chemical or biological modification. Examples of the chemically modified variant include variants chemically modified by linking a chemical moiety to an amino acid skeleton, chemically modified variants having a bond of a chemical moiety to an N-linked or O-linked carbohydrate chain, etc. Examples of the biologically modified variant include variants obtained by post-translational modification (such as N-linked or O-linked glycosylation, N- or C-terminal processing, deamidation, isomerization of aspartic acid, or oxidation of methionine), and variants in which a methionine residue has been added to the N terminus by being expressed in a prokaryotic host cell. Further, an antibody labeled so as to enable the detection or isolation of the antibody or an antigen of the present invention, for example, an enzyme-labeled antibody, a fluorescence-labeled antibody, and an affinity-labeled antibody are also included in the meaning of the modified variant. Such a modified variant of the antibody of the present invention is useful for improving the stability and blood retention of the antibody, reducing the antigenicity thereof, detecting or isolating an antibody or an antigen, and so on.

Further, by regulating the modification of a glycan which is linked to the antibody used in the present invention (glycosylation, defucosylation, etc.), it is possible to enhance an antibody-dependent cellular cytotoxic activity. As the technique for regulating the modification of a glycan of antibodies, WO 99/54342, WO 00/61739, WO 02/31140, etc. are known. However, the technique is not limited thereto. In the antibody of the present invention, an antibody in which the modification of a glycan is regulated is also included.

In the case where an antibody is produced by first isolating an antibody gene and then introducing the gene into an appropriate host, a combination of an appropriate host and an appropriate expression vector can be used. Specific examples of the antibody gene include a combination of a gene encoding a heavy chain sequence of an antibody described in this specification and a gene encoding a light chain sequence thereof. When a host cell is transformed, it is possible to insert the heavy chain sequence gene and the light chain sequence gene into the same expression vector, and also into different expression vectors separately.

In the case where eukaryotic cells are used as the host, animal cells, plant cells, and eukaryotic microorganisms can be used. As the animal cells, mammalian cells, for example, simian COS cells (Gluzman, Y., Cell, (1981) 23, pp. 175-182, ATCC CRL-1650), murine fibroblasts NIH3T3 (ATCC No. CRL-1658), and dihydrofolate reductase-deficient strains (Urlaub, G. and Chasin, L. A., Proc. Natl. Acad. Sci. USA (1980) 77, pp. 4126-4220) of Chinese hamster ovarian cells (CHO cells; ATCC: CCL-61) can be exemplified.

In the case where prokaryotic cells are used, for example, *Escherichia coli* and *Bacillus subtilis* can be exemplified.

By introducing a desired antibody gene into these cells through transformation, and culturing the thus transformed cells in vitro, the antibody can be obtained. In the above-described culture method, the yield may sometimes vary depending on the sequence of the antibody, and therefore, it is possible to select an antibody which is easily produced as a pharmaceutical by using the yield as an index among the antibodies having an equivalent binding activity. Therefore, in the antibody of the present invention, an antibody obtained by a method of producing an antibody, characterized by including a step of culturing the transformed host cell and a step of collecting a desired antibody from a cultured product obtained in the culturing step is also included.

It is known as to an antibody produced in a cultured mammalian cell that a lysine residue at the carboxyl terminus of the heavy chain thereof is deleted (Journal of Chromatography A, 705: 129-134 (1995)), and it is also known that two amino acid residues (glycine and lysine) at the carboxyl terminus of the heavy chain thereof are deleted and a proline residue newly located at the carboxyl terminus is amidated (Analytical Biochemistry, 360: 75-83 (2007)). However, such deletion and modification of the heavy chain sequence do not affect the antigen-binding affinity and the effector function (the activation of a complement, the antibody-dependent cellular cytotoxicity, etc.) of the antibody. Therefore, in the antibody according to the present invention, an antibody subjected to such modification and a functional fragment of the antibody is also included, and a deletion variant in which one or two amino acids have been deleted at the carboxyl terminus of the heavy chain, a variant obtained by amidation of the deletion variant (for example, a heavy chain in which the carboxyl terminal proline residue has been amidated), and the like are also included. The type of deletion variant having a deletion at the carboxyl terminus of the heavy chain of the antibody according to the invention is not limited to the above variants as long as the antigen-binding affinity and the effector function are conserved. The two heavy chains constituting the antibody according to the invention may be of one type selected from the group consisting of a full-length heavy chain and the above-described deletion variant, or may be of two types in combination selected therefrom. The ratio of the amount of each deletion variant can be affected by the type of cultured mammalian cells which produce the antibody according to the present invention and the culture conditions, however, those in which one amino acid residue at the carboxyl terminus has been deleted, preferably, in both of the two heavy chains, in the antibody according to the present invention can be exemplified.

As isotype of the antibody used in the present invention, for example, IgG (IgG1, IgG2, IgG3, IgG4) can be exemplified, and IgG1 or IgG2 can be exemplified preferably.

As the biological activity of the antibody, generally an antigen-binding activity, an activity of internalizing in cells expressing an antigen by binding to the antigen, an activity of neutralizing the activity of an antigen, an activity of enhancing the activity of an antigen, an antibody-dependent cellular cytotoxicity (ADCC) activity, a complement-dependent cytotoxicity (CDC) activity, and an antibody-dependent cell-mediated phagocytosis (ADCP) can be exemplified. The biological activity of the antibody of the present invention is a binding activity to HER2, and preferably an activity of internalizing in HER2-expressing cells by binding to HER2. Further, the antibody of the present invention may have an ADCC activity, a CDC activity, and/or an ADCP activity in addition to an activity of internalizing in cells.

The obtained antibody can be purified to homogeneity. The separation and purification of the antibody may be performed employing a conventional protein separation and purification method. For example, the antibody can be separated and purified by appropriately selecting and combining column chromatography, filter filtration, ultrafiltration, salt precipitation, dialysis, preparative polyacrylamide gel electrophoresis, isoelectric focusing electrophoresis, and the like (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but the method is not limited thereto.

Examples of such chromatography include affinity chromatography, ion exchange chromatography, hydrophobic chromatography, gel filtration chromatography, reverse phase chromatography, and adsorption chromatography.

Such chromatography can be performed employing liquid chromatography such as HPLC or FPLC.

As a column to be used in affinity chromatography, a Protein A column and a Protein G column can be exemplified. For example, as a column using a Protein A column, Hyper D, POROS, Sepharose FF (Pharmacia Corporation) and the like can be exemplified.

Further, by using a carrier having an antigen immobilized thereon, the antibody can also be purified utilizing the binding property of the antibody to the antigen.

[Antitumor Compound]

The antitumor compound to be conjugated to the anti-HER2 antibody-drug conjugate used in the present invention is explained. This antitumor compound is exatecan (IUPAC name: (1S,9S)-1-amino-9-ethyl-5-fluoro-1,2,3,9,12,15-hexahydro-9-hydroxy-4-methyl-10H,13H-benzo[de]pyrano[3',4':6,7]indolizino[1,2-b]quinolin-10,13-dione (which can also be referred to as chemical name: (1S,9S)-1-amino-9-ethyl-5-fluoro-2,3-dihydro-9-hydroxy-4-methyl-1H,12H-benzo[de]pyrano[3',4':6,7]indolizino[1,2-b]quinolin-10,13(9H,15H)-dione), one of the camptothecin derivatives. exatecan is a compound represented by the following formula:

[Formula 23]

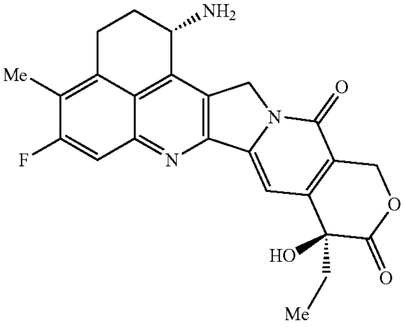

Because exatecan has a camptothecin structure, it is known that the equilibrium shifts to a structure with a closed lactone ring (closed ring) in an aqueous acidic medium (for example, pH 3 or so) but it shifts to a structure with an open lactone ring (open ring) in an aqueous basic medium (for example, pH 10 or so). It is needless to say that any antibody-drug conjugate being introduced with an exatecan residue corresponding to the closed ring structure and the open ring structure is also within the scope of the antibody-drug conjugate used in the present invention.

[Linker Structure]

With regard to the anti-HER2 antibody-drug conjugate used in the present invention, the linker structure for conjugating an antitumor compound to the anti-HER2 antibody is explained. The linker can be represented by the following formula:

-(Succinimid-3-yl-N)—$CH_2CH_2CH_2CH_2CH_2$—C(═O)-GGFG-NH—$CH_2$—O—$CH_2$—C(═O)— ("GGFG" disclosed as SEQ ID NO: 5)

wherein (Succinimid-3-yl-N)- has a structure represented by the following formula:

[Formula 24]

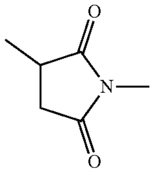

which is connected to the anti-HER2 antibody at position 3 thereof via a thioether bond and is connected to the methylene group in the linker structure containing this structure on the nitrogen atom at position 1, and -GGFG- represents the tetrapeptide residue of -Gly-Gly-Phe-Gly- (SEQ ID NO: 5).

[Compound that is Released in Tumor Cell]

With regard to the anti-HER2 antibody-drug conjugate used in the present invention, when it is transferred to the inside of tumor cells, the linker moiety is cleaved and the drug derivative having a structure represented by the formula: $NH_2$—$CH_2$—O—$CH_2$—C(═O)—(NH-DX) may be released.

It has been confirmed that, as the aminal structure in the molecule of the drug derivative is unstable, it again undergoes a self-degradation to release a compound represented by the formula:

O—$CH_2$—C(═O)—(NH-DX).

The compound can be represented by the following formula:

[Formula 25]

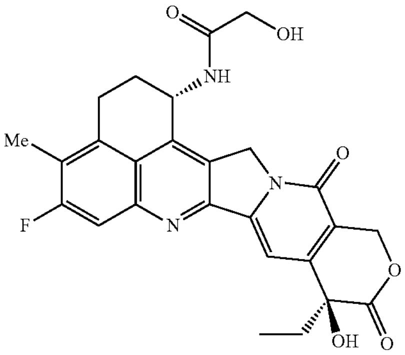

(hereinafter, also referred to as "Compound 1" in the present invention).

Compound 1 is considered as the main pharmaceutically active substance of antitumor activity possessed by the antibody-drug conjugate used in the present invention and has been confirmed to have a topoisomerase I inhibitory effect (Ogitani Y. et al., Clinical Cancer Research, 2016, Oct. 15; (20):5097-5108, Epub 2016 Mar. 29).

It is also known that the antibody-drug conjugate used in the present invention has a bystander effect (Ogitani Y. et al., Cancer Science (2016) 107, 1039-1046). After the antibody-drug conjugate used in the present invention internalizes in HER2-expressing cancer cells, this bystander effect is exerted by released Compound 1 that exerts an antitumor effect even on adjacent cancer cells expressing no HER2.

[Production Method]

The antibody-drug conjugate used in the present invention can be produced by reacting an anti-HER2 antibody having a thiol group (also referred to as a sulfhydryl group) with the following compound (hereinafter, also referred to as "Compound 2" in the present invention):

(maleimid-N-yl)-$CH_2CH_2CH_2CH_2CH_2$—C(═O)-GGFG-NH—$CH_2$—O—$CH_2$—C(═O)—(NH-DX) ("GGFG" disclosed as SEQ ID NO: 5)

wherein (maleimid-N-yl)- is a group represented by the following formula:

[Formula 26]

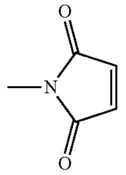

wherein the nitrogen atom is the connecting position,

—(NH-DX) is a group represented by the following formula:

[Formula 27]

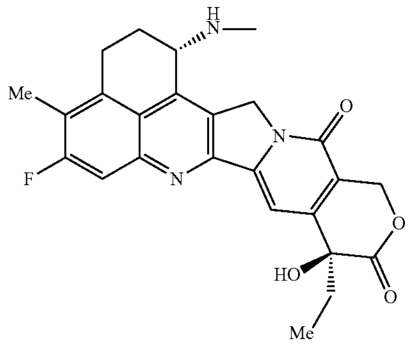

wherein the nitrogen atom of the amino group at position 1 is the connecting position, and -GGFG- represents the tetrapeptide residue of -Gly-Gly-Phe-Gly- (SEQ ID NO: 5).

Compound 2 can be produced with reference to a production method described in Examples 26, 32, and 33 of WO 2015/115091, etc. Compound 2 can be represented by the chemical name N-[6-(2,5-dioxo-2,5-dihydro-1H-pyrrol-1-yl) hexanoyl] glycylglycyl-L-phenylalanyl-N-[(2- {[(1S, 9S)-9-ethyl-5-fluoro-9-hydroxy-4-methyl-10,13-dioxo-2,3, 9,10, 13, 15-hexahydro-1H, 12H-benzo[de]pyrano[3',4':6,7] indolizino[1,2-b]quinolin-1-yl]amino}-2-oxoethoxy) methyl]glycineamide ("glycylglycyl-L-phenylalanyl" disclosed as SEQ ID NO: 14).

The anti-HER2 antibody having a sulfhydryl group can be obtained by a method well known to those skilled in the art (Hermanson, G. T, Bioconjugate Techniques, pp. 56-136, pp. 456-493, Academic Press (1996)). Examples include: the anti-HER2 antibody is reacted with a reducing agent such as tris(2-carboxyethyl)phosphine hydrochloride (TCEP) to reduce the disulfide bond in the hinge part in the antibody to form a sulfhydryl group, but it is not limited thereto.

Specifically, using 0.3 to 3 molar equivalents of TCEP as a reducing agent per disulfide at the hinge part in the antibody and reacting with the anti-HER2 antibody in a buffer solution containing a chelating agent, the anti-HER2 antibody with partially or completely reduced disulfide at the hinge part in the antibody can be obtained. Examples of the chelating agent include ethylenediamine tetraacetic acid (EDTA) and diethylenetriamine pentaacetic acid (DTPA). It can be used at the concentration of 1 mM to 20 mM. Examples of the buffer solution which may be used include a solution of sodium phosphate, sodium borate, or sodium acetate. Specifically, by reacting the anti-HER2 antibody with TCEP at 4° C. to 37° C. for 1 to 4 hours, an anti-HER2 antibody having a partially or completely reduced sulfhydryl group can be obtained.

Meanwhile, by conducting the reaction for adding a sulfhydryl group to a drug-linker moiety, the drug-linker moiety can be conjugated by a thioether bond.

Using 2 to 20 molar equivalents of Compound 2 per the anti-HER2 antibody having a sulfhydryl group, the antibody-drug conjugate (1) in which 2 to 8 drug molecules are conjugated per anti-HER2 antibody molecule can be produced. Specifically, it is sufficient that the solution containing Compound 2 dissolved therein is added to a buffer solution containing the anti-HER2 antibody having a sulfhydryl group for the reaction. Herein, examples of the buffer solution which may be used include sodium acetate solution, sodium phosphate, and sodium borate. The pH for the reaction is 5 to 9, and more preferably the reaction is performed near pH 7. Examples of the solvent for dissolving the Compound 2 include an organic solvent such as dimethyl sulfoxide (DMSO), dimethylformamide (DMF), dimethyl acetamide (DMA), and N-methyl-2-pyridone (NMP).

It is sufficient that the organic solvent solution containing Compound 2 dissolved therein is added at 1 to 20% v/v to a buffer solution containing the anti-HER2 antibody having a sulfhydryl group for the reaction. The reaction temperature is 0 to 37° C., more preferably 10 to 25° C., and the reaction time is 0.5 to 2 hours. The reaction can be terminated by deactivating the reactivity of unreacted Compound 2 with a thiol-containing reagent. Examples of the thiol-containing reagent include cysteine and N-acetyl-L-cysteine (NAC). More specifically, 1 to 2 molar equivalents of NAC are added to the Compound 2 used and, by incubating at room temperature for 10 to 30 minutes, the reaction can be terminated.

The produced antibody-drug conjugate can, after concentration, buffer exchange, purification, and measurement of antibody concentration and average number of conjugated drug molecules per antibody molecule according to common procedures described below, be subjected to identification of the antibody-drug conjugate.

Common procedure A: Concentration of aqueous solution of antibody or antibody-drug conjugate To a Amicon Ultra (50,000 MWCO, Millipore Co.) container, a solution of antibody or antibody-drug conjugate was added and the solution of the antibody or antibody-drug conjugate was concentrated by centrifugation (centrifuge for 5 to 20 minutes at 2000 G to 3800 G) using a centrifuge (Allegra X-15R, Beckman Coulter, Inc.).

Common procedure B: Measurement of antibody concentration Using a UV detector (Nanodrop 1000, Thermo Fisher Scientific Inc.), measurement of the antibody concentration was performed according to the method defined by the manufacturer. At that time, a 280 nm absorption coefficient different for each antibody was used (1.3 $mLmg^{-1}$ $cm^{-1}$ to 1.8 $mLmg^{-1}$ $cm^{-1}$).

Common Procedure C-1: Buffer Exchange for Antibody

NAP-25 column (Cat. No. 17-0852-02, GE Healthcare Japan Corporation) using Sephadex G-25 carrier was equilibrated with phosphate buffer (10 mM, pH 6.0; it is referred to as PBS6.0/EDTA in the specification) containing sodium chloride (137 mM) and ethylene diamine tetraacetic acid (EDTA, 5 mM) according to the method defined by the manufacturer. Aqueous solution of the antibody was applied in an amount of 2.5 mL to single NAP-25 column, and then the fraction (3.5 mL) eluted with 3.5 mL of PBS6.0/EDTA was collected. The resulting fraction was concentrated by the Common procedure A. After measuring the concentration of the antibody using the Common procedure B, the antibody concentration was adjusted to 10 mg/mL using PBS6.0/EDTA.

Common Procedure C-2: Buffer Exchange for Antibody

NAP-25 column (Cat. No. 17-0852-02, GE Healthcare Japan Corporation) using Sephadex G-25 carrier was equilibrated with phosphate buffer (50 mM, pH 6.5; it is referred to as PBS6.5/EDTA in the specification) containing sodium chloride (50 mM) and EDTA (2 mM) according to the method defined by the manufacturer. Aqueous solution of the antibody was applied in an amount of 2.5 mL to single NAP-25 column, and then the fraction (3.5 mL) eluted with 3.5 mL of PBS6.5/EDTA was collected. The resulting fraction was concentrated by the Common procedure A. After measuring the concentration of the antibody using the Common procedure B, the antibody concentration was adjusted to 20 mg/mL using PBS6.5/EDTA.

Common Procedure D: Purification of Antibody-Drug Conjugate

NAP-25 column was equilibrated with any buffer selected from commercially available phosphate buffer (PBS7.4, Cat. No. 10010-023, Invitrogen), sodium phosphate buffer (10 mM, pH 6.0; it is referred to as PBS6.0) containing sodium chloride (137 mM), and acetate buffer containing sorbitol (5%) (10 mM, pH 5.5; it is referred to as ABS in the specification). Aqueous solution of the antibody-drug conjugate reaction was applied in an amount of about 1.5 mL to the NAP-25 column, and then eluted with the buffer in an amount defined by the manufacturer to collect the antibody fraction. The collected fraction was again applied to the NAP-25 column and, by repeating 2 to 3 times in total the gel filtration purification process for eluting with buffer, the antibody-drug conjugate excluding non-conjugated drug linker and a low-molecular-weight compound (tris(2-carboxyethyl)phosphine hydrochloride (TCEP), N-acetyl-L-cysteine (NAC), and dimethyl sulfoxide) was obtained.

Common Procedure E: Measurement of Antibody Concentration in Antibody-Drug Conjugate and Average Number of Conjugated Drug Molecules Per Antibody Molecule (1).

The conjugated drug concentration in the antibody-drug conjugate can be calculated by measuring UV absorbance of an aqueous solution of the antibody-drug conjugate at two wavelengths of 280 nm and 370 nm, followed by performing the calculation shown below.

Because the total absorbance at any wavelength is equal to the sum of the absorbance of every light-absorbing chemical species that are present in the system (additivity of absorbance), when the molar absorption coefficients of the antibody and the drug remain the same before and after conjugation between the antibody and the drug, the antibody concentration and the drug concentration in the antibody-drug conjugate are expressed by the following equations.

$$A_{280}=A_{D,280}+A_{A,280}=\varepsilon_{D,280}C_D+\varepsilon_{A,280}C_A \qquad \text{Equation (I)}$$

$$A_{370}=A_{D,370}+A_{A,370}=\varepsilon_{D,370}C_D+\varepsilon_{A,370}C_A \qquad \text{Equation (II)}$$

In the above, $A_{280}$ represents the absorbance of an aqueous solution of the antibody-drug conjugate at 280 nm, $A_{370}$ represents the absorbance of an aqueous solution of the antibody-drug conjugate at 370 nm, $A_{A,280}$ represents the absorbance of an antibody at 280 nm, $A_{A,370}$ represents the absorbance of an antibody at 370 nm, $A_{D,280}$ represents the absorbance of a conjugate precursor at 280 nm, $A_{D,370}$ represents the absorbance of a conjugate precursor at 370 nm, $\varepsilon_{A,280}$ represents the molar absorption coefficient of an antibody at 280 nm, $\varepsilon_{A,370}$ represents the molar absorption coefficient of an antibody at 370 nm, $\varepsilon_{D,280}$ represents the molar absorption coefficient of a conjugate precursor at 280 nm, $C_D$,370 represents the molar absorption coefficient of a conjugate precursor at 370 nm, $C_A$ represents the antibody concentration in an antibody-drug conjugate, and $C_D$ represent the drug concentration in an antibody-drug conjugate.

As for $\varepsilon_{A,280}$, $\varepsilon_{A,370}$, $\varepsilon_{D,280}$, and $\varepsilon_{D,370}$ in the above, previously prepared values (estimated values based on calculation or measurement values obtained by UV measurement of the compounds) are used. For example, $\varepsilon_{A,280}$ can be estimated from the amino acid sequence of an antibody using a known calculation method (Protein Science, 1995, vol. 4, 2411-2423). $\varepsilon_{A,370}$ is generally zero. In Production Examples, as for the molar absorption coefficient of trastuzumab, $\varepsilon_{A,280}$=215400 (estimated value based on calculation) and $\varepsilon_{A,370}$=0 were used. $\varepsilon_{D,280}$ and $\varepsilon_{D,370}$ can be obtained based on Lambert-Beer's law (Absorbance=molar concentration×molar absorption coefficient×cell path length) by measuring the absorbance of a solution in which the conjugate precursor to be used is dissolved at a certain molar concentration. As for the molar absorption coefficient of a drug linker in the Examples, $\varepsilon_{D,280}$=5000 (measured average value) and $\varepsilon_{D,370}$=19000 (measured average value) were used, unless otherwise specified. By measuring $A_{280}$ and $A_{370}$ of an aqueous solution of the antibody-drug conjugate and solving the simultaneous equations (I) and (II) using the values, $C_A$ and $C_D$ can be obtained. Further, by dividing $C_D$ by $C_A$, the average number of conjugated drug molecules per antibody molecule can be obtained.

Common procedure F: Measurement (2) of average number of conjugated drug molecules per antibody molecule in antibody-drug conjugate.

The average number of conjugated drug molecules per antibody molecule in the antibody-drug conjugate can also be determined by high-performance liquid chromatography (HPLC) analysis using the following method in addition to the aforementioned Common procedure E.

[F-1. Preparation of Sample for HPLC Analysis (Reduction of Antibody-Drug Conjugate)]

An antibody-drug conjugate solution (about 1 mg/mL, 60 μL) is mixed with an aqueous solution of dithiothreitol (DTT) (100 mM, 15 μL). A sample in which the disulfide bond between the L chain and the H chain of the antibody-drug conjugate has been cleaved by incubating the mixture for 30 minutes at 37° C. is used in HPLC analysis.

[F-2. HPLC Analysis]

The HPLC analysis is performed under the following measurement conditions:

HPLC system: Agilent 1290 HPLC system (Agilent Technologies, Inc.)

Detector: ultraviolet absorption spectrometer (measurement wavelength: 280 nm)

Column: PLRP-S (2.1×50 mm, 8 μm, 1000 angstroms; Agilent Technologies, Inc., P/N PL1912-1802)

Column temperature: 80° C.

Mobile phase A: aqueous solution containing 0.04% trifluoroacetic acid (TFA)

Mobile phase B: acetonitrile solution containing 0.04% TFA

Gradient program: 29%-36% (0-12.5 min), 36%-42% (12.5-15 min), 42%-29% (15-15.1 min), and 29%-29% (15.1-25 min)

Sample injection volume: 15 μL

[F-3. Data Analysis]

[F-3-1] Compared with non-conjugated antibody L ($L_0$) and H ($H_0$) chains, drug-conjugated L (L chain connected to one drug molecule: $L_1$) and H (H chain connected to one drug molecule: $H_1$, H chain connected to two drug molecule: $H_2$, H chain connected to three drug molecules: $H_3$) chains exhibit higher hydrophobicity in proportion to the number of conjugated drug molecules and thus have a larger retention time. These chains are therefore eluted in the order of $L_0$ and $L_1$ or $H_0$, $H_1$, $H_2$, and $H_3$. Detection peaks can be assigned to any of $L_0$, $L_1$, $H_0$, $H_1$, $H_2$, and $H_3$ by the comparison of retention times with $L_0$ and $H_0$.

[F-3-2] Since the drug linker has UV absorption, peak area values are corrected in response to the number of conjugated drug linker molecules according to the following expression using the molar absorption coefficients of the L or H chain and the drug linker.

[Expression 1]

$$\text{Corrected value of the peak area of the } L \text{ chain } (Li) = \text{Peak area} \times \frac{\text{Molar absorption coefficient of the } L \text{ chain}}{\text{Molar absorption coefficient of the } L \text{ chain} + \text{The number of conjugated drug molecules} \times \text{Molar absorption coefficient of the drug}}$$

[Expression 2]

$$\text{Corrected value of the peak area of the } H \text{ chain } (Hi) = \text{Peak area} \times \frac{\text{Molar absorption coefficient of the } H \text{ chain}}{\text{Molar absorption coefficient of the } H \text{ chain} + \text{The number of conjugated drug molecules} \times \text{Molar absorption coefficient of the drug}}$$

Here, as for the molar absorption coefficient (280 nm) of the L or H chain of each antibody, a value estimated from the amino acid sequence of the L or H chain of each antibody by a known calculation method (Protein Science, 1995, vol. 4, 2411-2423) can be used. In the case of trastuzumab, a molar absorption coefficient of 26150 and a molar absorption coefficient of 81290 were used as estimated values for the L and H chains, respectively, according to its amino acid sequence. As for the molar absorption coefficient (280 nm) of the drug linker, the measured molar absorption coefficient (280 nm) of a compound in which the maleimide group was converted to succinimide thioether by the reaction of each drug linker with mercaptoethanol or N-acetylcysteine was used.

[F-3-3] The peak area ratio (%) of each chain is calculated for the total of the corrected values of peak areas according to the following expression.

[Expression 3]

$$\text{Peak area ratio of the } L \text{ chain} = \frac{A_{Li}}{A_{L0} + A_{L1}} \times 100$$

$$\text{Peak area ratio of the } H \text{ chain} = \frac{A_{Hi}}{A_{H0} + A_{H1} + A_{H2} + A_{H3}} \times 100$$

$A_{Li}$, $A_{Hi}$: Corrected values of respective peak areas of $L_i$, $H_i$

[F-3-4] The average number of conjugated drug molecules per antibody molecule in the antibody-drug conjugate is calculated according to the following expression.

$$\text{Average number of conjugated drug molecules} = (L_0 \text{ peak area ratio} \times 0 + L_1 \text{ peak area ratio} \times 1 + H_0 \text{ peak area ratio} \times 0 + H_1 \text{ peak area ratio} \times 1 + H_2 \text{ peak area ratio} \times 2 + H_3 \text{ peak area ratio} \times 3)/100 \times 2$$

The anti-HER2 antibody-drug conjugate used in the present invention, when it is left in air or recrystallized or purified, may absorb moisture or have adsorption water to turn into a hydrate, and such compounds or salts containing water are also included in the anti-HER2 antibody-drug conjugate used in the present invention.

Compounds labeled with various radioactive or non-radioactive isotopes are also included in the anti-HER2 antibody-drug conjugate used in the present invention. One or more atoms constituting the antibody-drug conjugate of the present invention may contain an atomic isotope at a non-natural ratio. Examples of atomic isotopes include deuterium ($^2H$), tritium ($^3H$), iodine-125 ($^{125}I$), and carbon-14 ($^{14}C$). Further, the compound of the present invention may be radioactive-labeled with a radioactive isotope such as tritium ($^3H$), iodine-125 ($^{125}I$), carbon-14 ($^{14}C$), copper-64 ($^{64}Cu$), zirconium-89 ($^{89}Zr$), iodine-124 ($^{124}I$), fluorine-18 ($^{18}F$), indium-111 ($^{111}I$), carbon-11 ($^{11}C$) and iodine-131 ($^{131}I$). The compound labeled with a radioactive isotope is useful as a therapeutic or prophylactic agent, a reagent for research such as an assay reagent and an agent for diagnosis such as an in vivo diagnostic imaging agent. Without being related to radioactivity, any isotope variant type of the antibody-drug conjugate used in the present invention is within the scope of the present invention.

[Medicine]

The therapeutic agent of the present invention contains the antibody-drug conjugate used in the present invention. Also, the treatment method of the present invention comprises administering the antibody-drug conjugate used in the present invention to a patient. These can be used as a therapeutic agent and a treatment method for HER2-expressing cancer having resistance or refractoriness to an existing anti-HER2 drug.

In the present invention, the term "resistance" or "refractoriness" refers to a property of having non-response to treatment with an anticancer agent and can also be expressed as "non-responsiveness" or "unresponsiveness". Furthermore, the term can also be expressed as "intolerance" because tumor growth cannot be prevented due to the non-response.

In the present invention, the term "resistance or refractoriness" may be "resistance or refractoriness acquired by the cancer due to treatment with an existing anti-HER2 drug" or may be "resistance or refractoriness intrinsic to the cancer independently of treatment with an existing anti-HER2 drug".

In the present invention, the term "HER2-expressing cancer" refers to cancer and/or tumor containing cancer cells expressing the HER2 protein on the cell surface.

In the present invention, the term "existing anti-HER2 drug" refers to a HER2-targeting drug used in clinical settings, except for the antibody-drug conjugate of the present invention, and preferably refers to an anti-HER2 drug used in standard treatment. The "existing anti-HER2 drug" is not particularly limited as long as it satisfies the requirements described above. The existing anti-HER2 drug is preferably at least one selected from the group consisting of trastuzumab emtansine (T-DM1), trastuzumab, pertuzumab, and lapatinib, more preferably trastuzumab emtansine or trastuzumab, still more preferably trastuzumab emtansine.

The therapeutic agent and the treatment method of the present invention can be preferably used for administration to a patient having a history of treatment with an existing anticancer drug.

In the present invention, the term "existing anticancer drug" refers to an anticancer drug used in clinical settings, except for the antibody-drug conjugate used in the present invention. The "existing anticancer drug" is not particularly limited as long as it satisfies the requirements described above. Preferably, the existing anticancer drug comprises at least one selected from the group consisting of trastuzumab emtansine, trastuzumab, pertuzumab, lapatinib, irinotecan (CPT-11), cisplatin, carboplatin, oxaliplatin, fluorouracil (5-FU), gemcitabine, capecitabine, paclitaxel, docetaxel, doxorubicin, epirubicin, cyclophosphamide, mitomycin C, a tegafur-gimeracil-oteracil combination drug, cetuximab, panitumumab, bevacizumab, ramucirumab, regorafenib, a trifluridine-tipiracil combination drug, gefitinib, erlotinib, afatinib, methotrexate, and pemetrexed.

In the case of the treatment of breast cancer, the "existing anticancer drug" preferably comprises at least one selected from the group consisting of trastuzumab emtansine, trastuzumab, pertuzumab, lapatinib, fluorouracil, paclitaxel, docetaxel, doxorubicin, epirubicin, cyclophosphamide, and methotrexate, more preferably comprises trastuzumab emtansine or trastuzumab, and still more preferably comprises trastuzumab emtansine.

In the case of the treatment of gastric cancer, the "existing anticancer drug" preferably comprises at least one selected from the group consisting of trastuzumab, irinotecan, cisplatin, fluorouracil, paclitaxel, docetaxel, doxorubicin, epirubicin, and mitomycin C, more preferably comprises trastuzumab and/or irinotecan, and still more preferably comprises trastuzumab.

In the case of the treatment of colorectal cancer, the "existing anticancer drug" preferably comprises at least one selected from the group consisting of irinotecan, oxaliplatin, fluorouracil, cetuximab, panitumumab, bevacizumab, ramucirumab, regorafenib, and a trifluridine-tipiracil combination drug, and more preferably comprises irinotecan.

In the case of the treatment of non-small cell lung cancer, the "existing anticancer drug" preferably comprises at least one selected from the group consisting of irinotecan, cisplatin, carboplatin, gemcitabine, gefitinib, erlotinib, afatinib, and pemetrexed.

With regard to the therapeutic agent and the treatment method of the present invention, the dose per administration of the antibody-drug conjugate used in the present invention is preferably in a range of 5.4 mg/kg (which represents that the dose per kg of body weight is 5.4 mg; the same holds true for the description below) to 8 mg/kg, more preferably 5.4 mg/kg, 6.4 mg/kg, 7.4 mg/kg, or 8 mg/kg, and still more preferably 5.4 mg/kg or 6.4 mg/kg.

In the therapeutic agent and the treatment method of the present invention, preferably, the antibody-drug conjugate used in the present invention is administered once every 3 weeks.

The therapeutic agent and the treatment method of the present invention can be preferably used for the treatment of at least one cancer selected from the group consisting of breast cancer, gastric cancer (also referred to as gastric adenocarcinoma), colorectal cancer (also referred to as colon and rectal cancer, including colon cancer and rectal cancer), non-small cell lung cancer, esophageal cancer, salivary gland cancer, esophagogastric junction adenocarcinoma, bile duct cancer, Paget's disease, pancreatic cancer, ovarian cancer, uterine cancer and sarcoma, can be more preferably used for the treatment of at least one cancer selected from the group consisting of breast cancer, gastric cancer, colorectal cancer, non-small cell lung cancer, esophageal cancer, salivary gland cancer, esophagogastric junction adenocarcinoma, bile duct cancer, and Paget's disease, and can be still more preferably used for the treatment of breast cancer, gastric cancer, colorectal cancer, or non-small cell lung cancer.

For breast cancer, treatment with the existing anti-HER2 drugs trastuzumab emtansine and trastuzumab is permitted. For gastric cancer and esophagogastric junction adenocarcinoma, treatment with the existing anti-HER2 drug trastuzumab is also permitted. Thus, in the case of using the therapeutic agent of the present invention for the treatment of at least one cancer selected from the group consisting of breast cancer, gastric cancer, and esophagogastric junction adenocarcinoma, the "resistance or refractoriness" is preferably "resistance or refractoriness acquired by the cancer due to treatment with the existing anti-HER2 drug".

On the other hand, for colorectal cancer, non-small cell lung cancer, esophageal cancer, salivary gland cancer, bile duct cancer, Paget's disease, pancreatic cancer, ovarian cancer, uterine cancer and sarcoma, any effective treatment method with an existing anti-HER2 drug has not been established. Thus, in the case of using the therapeutic agent and the treatment method of the present invention for the treatment of at least one cancer selected from the group consisting of colorectal cancer, non-small cell lung cancer, esophageal cancer, salivary gland cancer, bile duct cancer, Paget's disease, pancreatic cancer, ovarian cancer, uterine cancer and sarcoma, the "resistance or refractoriness" is preferably "resistance or refractoriness intrinsic to the cancer independently of treatment with the existing anti-HER2 drug".

The therapeutic agent and the treatment method of the present invention can be used for HER2-expressing cancer, which may be HER2-overexpressing cancer or may be HER2 low-expressing cancer.

In the present invention, the term "HER2-overexpressing cancer" is not particularly limited as long as it is recognized as HER2-overexpressing cancer by those skilled in the art. Preferred examples of the HER2-overexpressing cancer can include cancer given a score of 3+ for the expression of HER2 in an immunohistochemical method (IHC), and cancer given a score of 2+ for the expression of HER2 in an immunohistochemical method and determined as positive for the expression of HER2 in an in situ hybridization method (ISH). The in situ hybridization method of the present invention includes a fluorescence in situ hybridization method (FISH) and a dual color in situ hybridization method (DISH).

In the present invention, the term "HER2 low-expressing cancer" is not particularly limited as long as it is recognized as HER2 low-expressing cancer by those skilled in the art. Preferred examples of the HER2 low-expressing cancer can include cancer given a score of 2+ for the expression of HER2 in an immunohistochemical method and determined as negative for the expression of HER2 in an in situ hybridization method, and cancer given a score of 1+ for the expression of HER2 in an immunohistochemical method.

The method for scoring the degree of HER2 expression by the immunohistochemical method, or the method for determining positivity or negativity to HER2 expression by the in situ hybridization method is not particularly limited as long as it is recognized by those skilled in the art. Examples of the method can include a method described in the 4th edition of the guidelines for HER2 testing, breast cancer (developed by the Japanese Pathology Board for Optimal Use of HER2 for Breast Cancer).

The therapeutic agent and the treatment method of the present invention can be preferably used for the treatment of inoperable or recurrent cancer.

The therapeutic agent and the treatment method of the present invention can contain a pharmaceutically acceptable formulation component for use.

In other words, the therapeutic agent of the present invention can also be used as a pharmaceutical composition for treatment of resistant cancer comprising the antibody-drug conjugate used in the present invention, a salt thereof, or a hydrate thereof as an active component, and a pharmaceutically acceptable formulation component.

The pharmaceutical composition for treatment of the present invention exhibits excellent antitumor activity against cancer that exhibits resistance to an existing anticancer drug (i.e., resistant cancer), particularly, cancer that has acquired resistance to an existing anticancer drug (i.e., secondary resistant cancer). Thus, the pharmaceutical composition for treatment of the present invention exerts a remarkable antitumor effect when applied to a patient group with cancer having resistance to an existing anticancer drug (patients having a history of treatment with an existing anticancer drug) among cancer patients.

The definition of the term "existing anticancer drug" is as mentioned above, and is preferably an antibody-drug conjugate comprising an anti-HER2 antibody such as trastuzumab emtansine (T-DM1), or an anti-HER2 antibody itself such as trastuzumab or pertuzumab.

The pharmaceutical composition for treatment of the present invention is administered instead of these existing anticancer drugs or in combination with these existing anticancer drugs to a cancer patient to thereby exhibit a high therapeutic effect on cancer that has acquired resistance to these existing anticancer drugs.

With regard to the pharmaceutical composition for treatment of the present invention, the dose per administration of the antibody-drug conjugate used in the present invention is preferably in a range of 0.8 mg/kg to 8 mg/kg, more preferably 5.4 mg/kg, 6.4 mg/kg, 7.4 mg/kg, or 8 mg/kg, and still more preferably 5.4 mg/kg or 6.4 mg/kg.

The dosing interval of the pharmaceutical composition for treatment of the present invention can be once every 1 week (q1w), once every 2 weeks (q2w), once every 3 weeks (q3w), or once every 4 weeks (q4w), but is preferably once every 3 weeks.

The pharmaceutical composition for treatment of the present invention can be preferably used when the resistant cancer is lung cancer, urothelial cancer, colorectal cancer, prostate cancer, ovarian cancer, pancreatic cancer, breast cancer, bladder cancer, gastric cancer, gastrointestinal stromal tumor, uterine cervix cancer, esophageal cancer, squamous cell carcinoma, peritoneal cancer, liver cancer, hepatocellular cancer, colon cancer, rectal cancer, colorectal cancer, endometrial cancer, uterine cancer, salivary gland cancer, kidney cancer, vulval cancer, thyroid cancer, penis cancer, leukemia, malignant lymphoma, plasmacytoma, myeloma, or sarcoma, can be more preferably used when the resistant cancer is breast cancer, gastric cancer, colorectal cancer, or non-small cell lung cancer, and can be still more preferably used when the resistant cancer is breast cancer or gastric cancer.

The therapeutic agent and the pharmaceutical composition for treatment of the present invention can delay development of cancer cells, inhibit growth thereof, and further kill cancer cells. These effects can allow cancer patients to be free from symptoms caused by cancer or achieve improvement in QOL of cancer patients and attains a therapeutic effect by sustaining the lives of the cancer patients. Even if the anti-HER2 antibody-drug conjugate of the present invention does not accomplish killing cancer cells, it can achieve higher QOL of cancer patients while achieving longer-term survival, by inhibiting or controlling the growth of cancer cells.

In such drug therapy, it can be used as a drug alone and in addition, it can be used as a drug in combination with an additional therapy in adjuvant therapy and can be combined with surgical operation, radiotherapy, hormone therapy, or the like. Furthermore, it can also be used as a drug for drug therapy in neoadjuvant therapy.

In addition to the therapeutic use as described above, a prophylactic effect of suppressing the growth of small metastatic cancer cells and further killing them can also be expected. Particularly, when the expression of HER2 is confirmed in primary cancer cells, inhibition of cancer metastasis or a prophylactic effect can be expected by administering the anti-HER2 antibody-drug conjugate used in the present invention. For example, an effect of inhibiting and killing cancer cells in a body fluid in the course of metastasis or an effect of, for example, inhibiting and killing small cancer cells immediately after implantation in any tissue can be expected. Accordingly, inhibition of cancer metastasis or a prophylactic effect can be expected, particularly, after surgical removal of cancer.

The anti-HER2 antibody-drug conjugate used in the present invention can be expected to exert a therapeutic effect by application as systemic therapy to patients, and additionally, by local application to cancer tissues.

The therapeutic agent and the pharmaceutical composition for treatment of the present invention can be preferably administered to a mammal, but it can be more preferably administered to a human.

The therapeutic agent and the pharmaceutical composition for treatment of the present invention may comprise at least one pharmaceutically acceptable formulation component for administration. The pharmaceutically acceptable formulation component can be suitably selected and applied from formulation additives or the like that are generally used in the art, in view of the dosage or administration concentration of the antibody-drug conjugate used in the present invention. The pharmaceutically acceptable formulation component typically includes at least one pharmaceutical carrier (for example, sterilized liquid). Herein, the liquid includes, for example, water and oil (petroleum oil and oil of animal origin, plant origin, or synthetic origin). The oil may be, for example, peanut oil, soybean oil, mineral oil, or sesame oil. Water is a more typical carrier when the therapeutic agent and the pharmaceutical composition for treatment of the present invention are intravenously administered. Saline solution, an aqueous dextrose solution, and an aqueous glycerol solution can be also used as a liquid carrier, in particular, for an injection solution. A suitable pharmaceutical vehicle can be selected from ones known in the art. If desired, the pharmaceutically acceptable formulation component may also include a trace amount of a moisturizing agent, an emulsifying agent, or a pH buffering agent. Examples of suitable pharmaceutically acceptable formulation component are disclosed in "Remington's Pharmaceutical Sciences" by E. W. Martin. The formulations correspond to an administration mode.

Various delivery systems are known and they can be used for administering the therapeutic agent and the pharmaceutical composition for treatment of the present invention. Examples of the administration route can include intradermal, intramuscular, intraperitoneal, intravenous, and subcutaneous routes, but not limited thereto. The administration can be made by injection or bolus injection, for example. According to a specific preferred embodiment, the administration of the therapeutic agent and the pharmaceutical composition for treatment of the present invention is performed by injection. Parenteral administration is a preferred administration route.

According to a representative embodiment, the therapeutic agent and the pharmaceutical composition for treatment of the present invention are prescribed, as a composition suitable for intravenous administration to human, according to the conventional procedures. The composition for intravenous administration is typically a solution in a sterile and isotonic aqueous buffer solution. If necessary, the therapeutic agent and the pharmaceutical composition for treatment of the present invention may contain a solubilizing agent and local anesthetics to alleviate pain at injection site (for example, lignocaine). Generally, the ingredient above is provided individually as any one of lyophilized powder or an anhydrous concentrate contained in a container which is obtained by sealing in an ampoule or a sachet having an amount of the active agent or as a mixture in a unit dosage form. When the therapeutic agent and the pharmaceutical composition for treatment of the present invention are to be administered by injection, they may be administered from an injection bottle containing water or saline of sterile pharmaceutical grade. When the therapeutic agent and the pharmaceutical composition for treatment of the present invention are administered by injection, an ampoule of sterile water or saline for injection may be provided such that the aforementioned ingredients are admixed with each other before administration.

The therapeutic agent and the pharmaceutical composition for treatment of the present invention may be a pharmaceutical composition comprising only the anti-HER2 antibody-drug conjugate used in the present invention or a pharmaceutical composition comprising the anti-HER2 antibody-drug conjugate used in the present invention and at least one cancer treating agent other than the anti-HER2 antibody-drug conjugate used in the present invention. The anti-HER2 antibody-drug conjugate used in the present invention can be administered with an existing anticancer drug. The anticancer effect may be enhanced accordingly. The existing anticancer drug used for such purpose may be administered to an individual simultaneously with, separately from, or subsequently to the antibody-drug conjugate of the present invention, and may be administered while varying the administration interval for each. The definition of the term "existing anticancer drug" is as mentioned above.

The therapeutic agent and the pharmaceutical composition for treatment of the present invention can be formulated into a lyophilization formulation or a liquid formulation as a formulation having the selected composition and required purity. When formulated as a lyophilization formulation, it may be a formulation comprising suitable formulation additives that are used in the art. Also for a liquid formulation, it can be formulated as a liquid formulation comprising various formulation additives that are used in the art.

EXAMPLES

The present invention is specifically described in view of the examples shown below. However, the present invention is not limited to these. Further, it is by no means interpreted in a limited way.

Production Example: Preparation of Antibody-Drug Conjugate

An antibody-drug conjugate represented by the following formula (hereinafter, referred to as an "antibody-drug conjugate (1)" or "ADC (1)") was produced according to a production method described in Patent Literature 8 (WO 2015/115091).

[Formula 28]

Anti-HER2 antibody

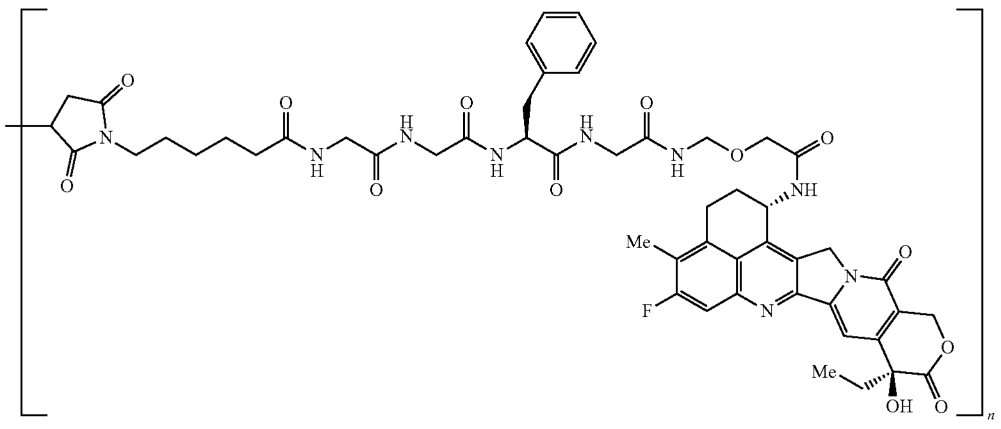

Here, the drug-linker structure was conjugated to the antibody via a thioether bond, and n is in a range of 7 to 8.

Evaluation Example 1: Antitumor Test

Mouse: 6- to 12-week-old female immunodeficient Crl: Nu(Ncr)-Foxn1$^{Nu}$ mice (Charles River Laboratories Japan, Inc.) were subjected to the experiment.

Assay and calculation expression: The major axis and minor axis of tumor were measured twice a week by using an electronic digital caliper, and the tumor volume ($mm^3$) was calculated. The calculation expression is as shown below.

$$\text{Tumor volume } (mm^3) = 0.52 \times \text{Major axis (mm)} \times [\text{Minor axis (min)}]^2$$

Antibody-drug conjugate (1): An antibody-drug conjugate of DAR=7.6 was used. The antibody-drug conjugate (1) was diluted with a solvent (10 mM histidine, 10% trehalose, 0.02% polysorbate 20, pH 5.5). Trastuzumab emtansine (T-DM1) was diluted with saline. The dilution of the antibody-drug conjugate (1) or the dilution of T-DM1 was used at a volume of 10 mL/kg for intravenous administration to the tail vein of each mouse.

Tumor excised from a patient with HER2-positive breast cancer that acquired resistance after treatment with T-DM1 was maintained at several passages by transplantation to female immunodeficient mice. Then, ST1616B/TDR and ST1360B/TDR were obtained as tumor that acquired high resistance to T-DM1 by the continuous administration of T-DM1 to the mice. ST1616B/TDR is tumor derived from a patient who received T-DM1 by continuous administration for 13 months, and ST1360B/TDR is a tumor derived from a patient who received T-DM1 by continuous administration for 3 months. Both of these tumors overexpressed HER2 (which given a score of 3+ in immunohistochemical staining (IHC)).

A tumor section of the solid tumor was subcutaneously transplanted to the side of the body of each female immunodeficient mouse, and the mice were randomly grouped when the tumor volume reached about 200 $mm^3$. The date of grouping was defined as Day 0. The antibody-drug conjugate (1) was intravenously administered at a dose of 3 mg/kg or 10 mg/kg to the tail vein of each mouse on Day 0. T-DM1 was intravenously administered at a dose of 10 mg/kg to the tail vein of each mouse on Days 0, 7, 14, and 21. An administration group of only the solvent used in the dilution of the antibody-drug conjugate (1) was established as a control group.

Figure 4:
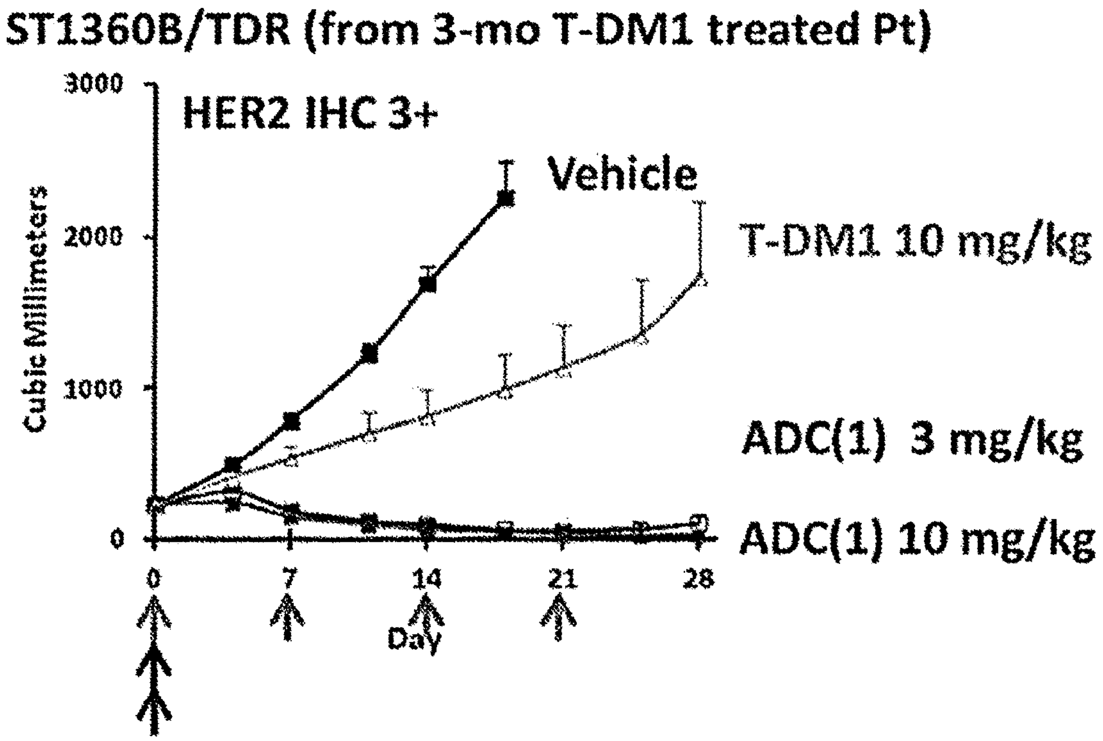
FIG. 4 is a diagram showing the antitumor effect of an antibody-drug conjugate (1) or T-DM1 on a nude mouse with subcutaneously transplanted tumor of HER2-positive human breast cancer ST1360B/TDR that acquired secondary resistance to T-DM1. In the drawing, the abscissa depicts days after initial administration, and the ordinate depicts tumor volume.

The results are shown in FIG. 3 or 4. The administration of T-DM1 did not inhibit the growth of the ST1616B/TDR tumor and the ST1360B/TDR tumor. By contrast, the administration of the antibody-drug conjugate (1) at both 3 mg/kg and 10 mg/kg remarkably inhibited the growth of the tumor. Weight loss of the mice was not observed in any of the drug administration groups.

These results demonstrated that the antibody-drug conjugate (1) has remarkable antitumor activity against tumor that has acquired resistance to T-DM1 (i.e., secondary resistant cancer). It is also evident that the antibody-drug conjugate (1) has favorable safety profile.

Evaluation Example 2: Clinical Study

Antibody-drug conjugates are promising medicines effective for efficient and specific drug delivery to oncogene-expressing tumor cells. The antibody-drug conjugate (1) is a novel HER2-targeting antibody-drug conjugate having a topoisomerase I inhibitor (Table 1). DAR of the antibody-drug conjugate (1) used in clinical studies was in a range of to 8, and the value is close to 8. Preclinical data demonstrated that the HER2 targeting thereof is very specific. In preclinical models, the antibody-drug conjugate (1) exhibited much wider antitumor spectra and a higher effect on T-DM1 resistant tumor and HER2 low-expressing tumor than those of trastuzumab emtansine (T-DM1).

Dose escalation part (Part 1) study and dose expansion part (Part 2) study are ongoing at Phase 1 for HER2-positive breast cancer, gastric cancer, and HER2-expressing solid cancer different therefrom as described below.

TABLE 1

| | ADC (1) | T-DM1 |
|---|---|---|
| Antibody | Anti-HER2 monoclonal antibody | Trastuzumab (Tmab) |
| Drug | Topoisomerase I inhibitor (Dxd) | Tubulin inhibitor (DM1) |
| DAR* | 7-8 | 3.5 |

*DAR: Average drug-to-antibody Ratio

Protocol:

Open-label, Phase 1 dose escalation study.

The maximum tolerated dose (MTD) is determined by the mCRM method conforming to the principles of EWOC.

The antibody-drug conjugate (1) is intravenously administered once every three weeks until intolerable toxicity or exacerbation of a pathological condition is observed.

Dose-limiting toxicity (DLT) is determined at Cycle 1 (Days 1 to 21).

Part 1 study: Dose escalation study (conducted in Japan)

Breast cancer or gastric adenocarcinoma/esophagogastric junction adenocarcinoma

The number of test subjects is set to at least 18, on the assumption that 16% of the test subjects (i.e., ⅙ of the test subjects) have HER2 expression (IHC 2+, 3+).

Part 2 study: Dose expansion study (conducted in Japan and the USA)

Part 2a; the number of test subjects: 40, HER2 overexpressing breast cancer having a history of treatment with T-DM1.

Part 2b; the number of test subjects: 40, HER2 overexpressing gastric adenocarcinoma/esophagogastric junction adenocarcinoma having a history of treatment with trastuzumab.

Part 2c; the number of test subjects: 20, HER2 low-expressing breast cancer.

Part 2d; the number of test subjects: 20, HER2-expressing solid cancer except for breast cancer or gastric adenocarcinoma.

Primary Objective:

Evaluation of the safety and tolerability of the antibody-drug conjugate (1).

The maximum tolerated dose and phase 2 study recommended dose of the antibody-drug conjugate (1) are determined. Secondary objective and exploratory objective:

Evaluation of the pharmacokinetics of the antibody-drug conjugate (1).

Evaluation of the efficacy of the antibody-drug conjugate

Objective response rate (ORR; complete response (CR)+partial response (PR)).

Disease control rate (DCR; CR+PR+stable disease (SD)).

Duration of response, duration of SD, response time, progression-free survival.

Evaluation of a human anti-human antibody for the antibody-drug conjugate (1).

Study Results

Part 1 study: Dose escalation study (conducted in Japan)

(1) Analysis of Test Subject

The statuses of the test subjects are as shown in Table 2.

TABLE 2

| Details of test subjects | |
|---|---|
| Enrolled test subjects/treated test subjects | 23/22 |
| Median age (range) | 66 (38-79) |
| The number of previous chemotherapy | 5 (1-11) |
| Tumor type | |
| Breast cancer | 16 (73%) |
| Gastric cancer | 5 (23%) |
| Esophagogastric junction adenocarcinoma | 1 (5%) |
| HER2 status | |
| IHC | |
| 0 | 1 (5%) |
| 1+ | 3 (14%) |
| 2+ | 3 (14%) |
| 3+ | 15 (68%) |

TABLE 2-continued

| FISH | |
|---|---|
| Non-amplified | 2 (9%) |
| Amplified | 2 (9%) |
| Not examined | 18 (82%) |
| Previous chemotherapy | |
| Anti-HER2 Therapy | 18 (82%) |
| Trastuzumab | 18 (82%) |
| Pertuzumab | 5 (23%) |
| Lapatiaib | 4 (18%) |
| T-DM1 | 13 (59%) |

(2) Pharmacokinetics

Figure 5:
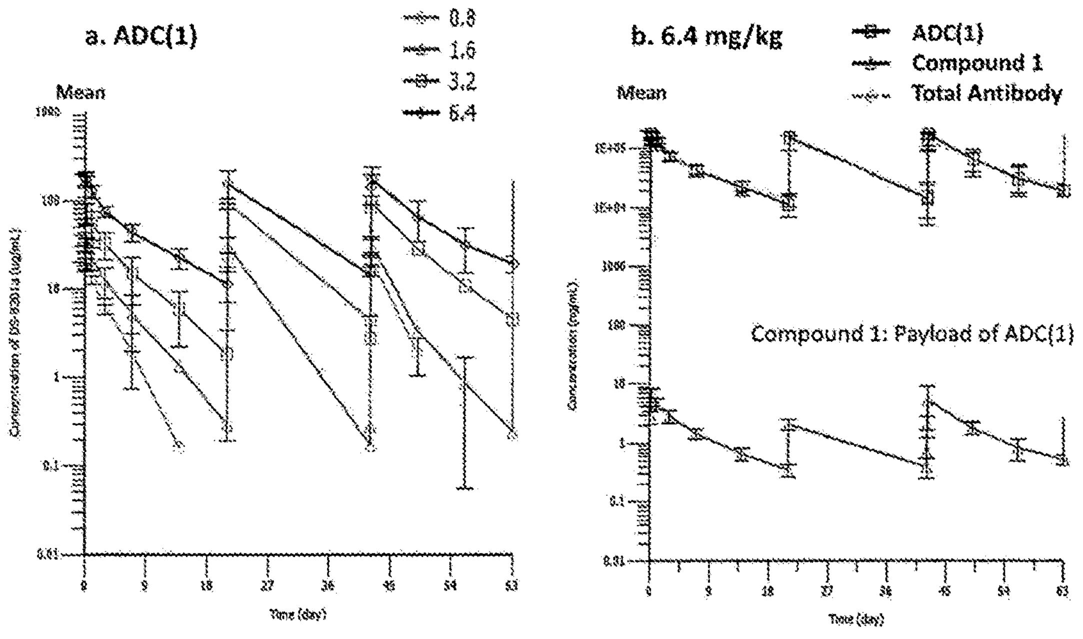
FIG. 5 is a diagram showing the pharmacokinetics of the antibody-drug conjugate (1) in a clinical study. Panel (a) shows the pharmacokinetics of various doses of ADC (1), and Panel (b) shows a comparison of the pharmacokinetics of ADC (1) and Compound 1 at a 6.4 mg/kg dose.

The antibody-drug conjugate (1) was administered once every three weeks (q3w) at any dose of 0.8 mg/kg, 1.6 mg/kg, 3.2 mg/kg, 5.4 mg/kg, 6.4 mg/kg, and 8 mg/kg. The pharmacokinetics of the antibody-drug conjugate (1) measured from these administrations is shown in FIG. 5.

The exposure of the antibody-drug conjugate (1) was higher than the dosage ratio at the doses of 3.2 mg/kg or larger, and $T_{1/2}$ was prolonged at the doses of 3.2 mg/kg or larger.

The compound described as "Compound 1" in the drawing is similar in $T_{1/2}$ to the antibody-drug conjugate (1) due to the flip-flop phenomenon (data not shown). Compound 1 has the following structure.

[Formula 29]

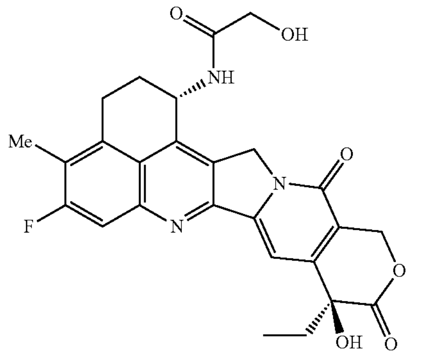

The median Cmin (10700 ng/mL) of the antibody-drug conjugate (1) administered at 6.4 mg/kg at Cycle 1 exceeded the target exposure (4260 ng/ml) based on the whole concentration of the active component in preclinical settings and was almost the same as the launched dose 3.6 mg/kg of T-DM1. The target dose of the antibody-drug conjugate (1) was 5.0 mg/kg.

(3) Safety and Tolerability

Figure 6:
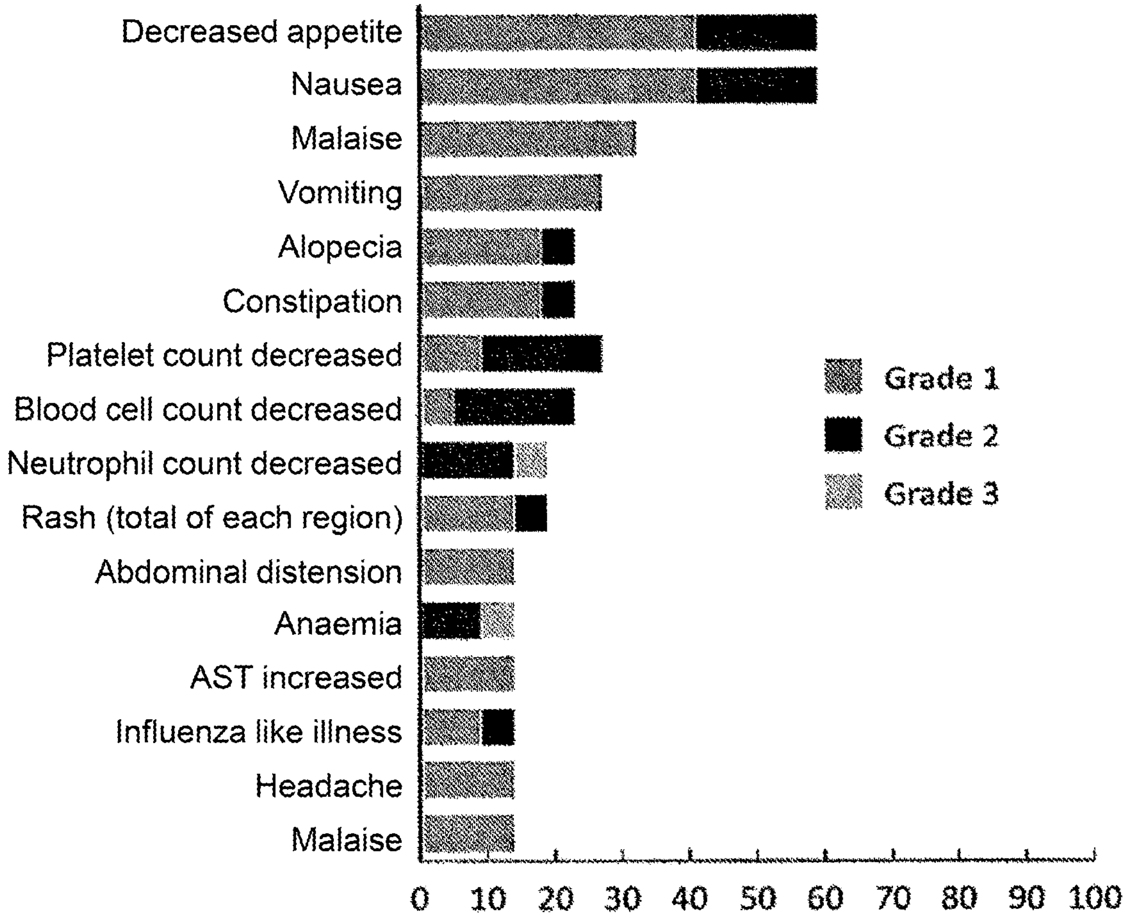
FIG. 6 is a diagram showing the safety and tolerability of the antibody-drug conjugate (1) in a clinical study.

The results about safety and tolerability are shown in FIG. 6.

MTD was not reached in cohorts that received 0.8 mg to 8 mg/kg.

None of the dose levels lead to dose-limiting toxicity, grade 4, and cardiotoxicity.

The most commonly observed adverse events (AEs) were mild to moderate gastrointestinal and hematological events.

Seven adverse events of grade 3 (hypokalemia (1), anaemia (1), neutrophil count decreased (1), lymphocyte count decreased (2), alkali phosphatase level increased (1), cholangitis (1)) occurred in 4 out of 22 test subjects (18%).

At Cycle 2 or later, adverse events were responsible for dose reduction in 6 test subjects in cohorts that received 6.4 mg/kg (n=4/6) and 8.0 mg/kg (n=2/3), but did not lead to the discontinuation of administration.

(4) Efficacy

Figure 7:
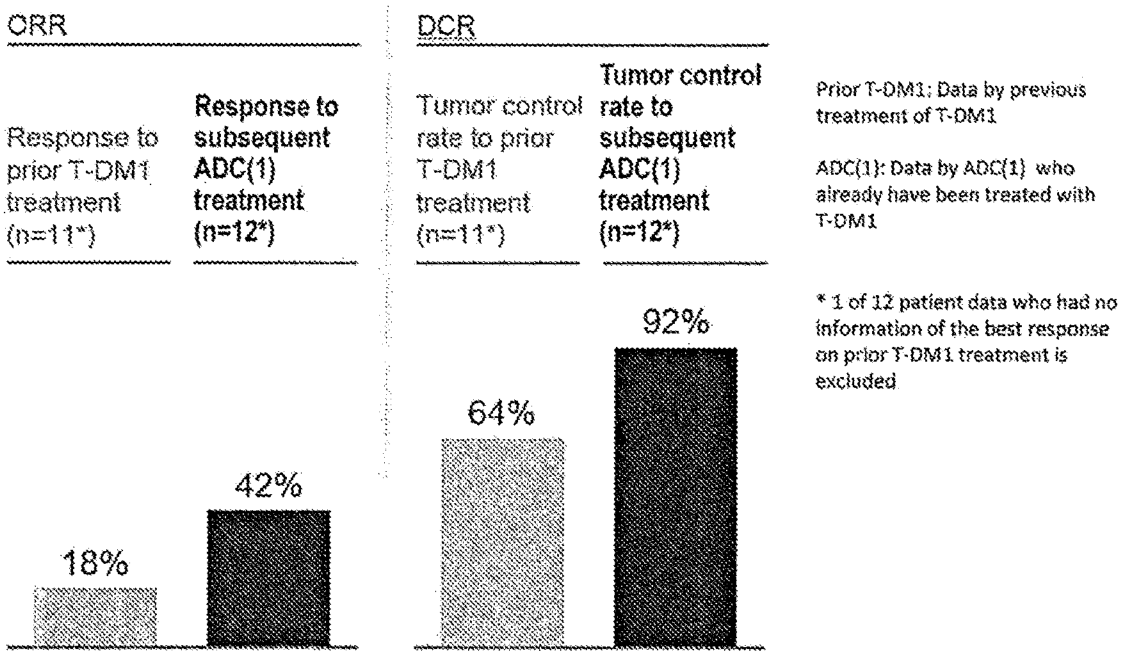
FIG. 7 is a diagram showing ORR (objective response rate) and DCR (disease control rate) as to the efficacy of the antibody-drug conjugate (1) in a clinical study.
Figure 8:
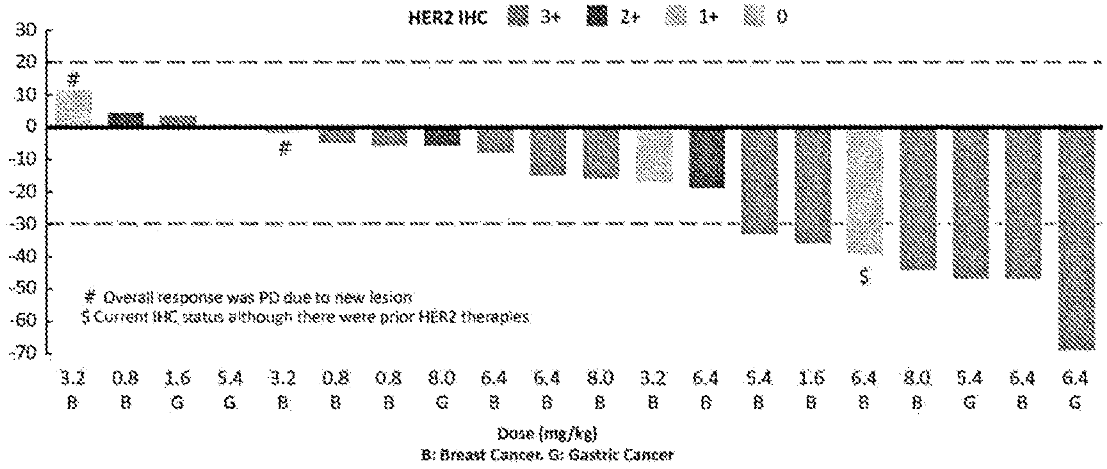
FIG. 8 is a diagram showing best % change from baseline in tumor size as to the efficacy of the antibody-drug conjugate (1) in a clinical study.
Figure 9:
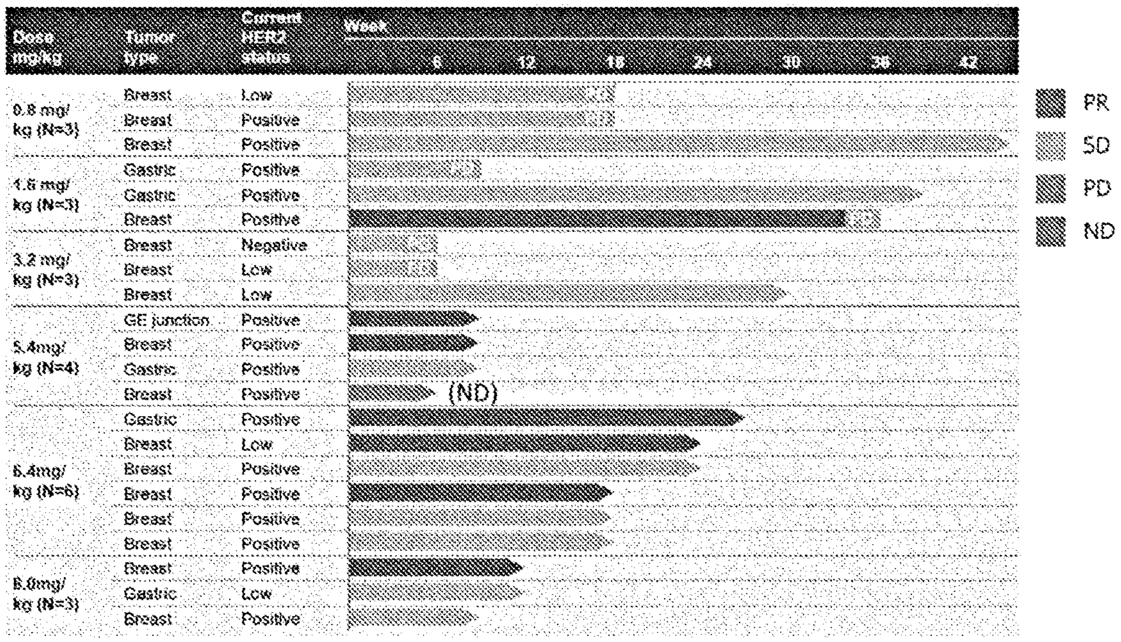
FIG. 9 is a diagram showing a treatment period and a therapeutic effect as to the efficacy of the antibody-drug conjugate (1) in a clinical study.

The efficacy is shown in FIGS. 7, 8 and 9.

ORR of 35% (7 PRs) and DCR of 90% were achieved in 20 evaluable test subjects including 12 test subjects previously treated with T-DM1 and 5 test subjects having HER2 low-expressing tumor (FIGS. 8 and 9).

The antibody-drug conjugate (1) achieved ORR of 42% and DCR of 92% for patients with breast cancer non-responsive or intolerable to standard treatment involving T-DM1 (FIG. 7). The therapeutic effect of T-DM1 in the prior treatment was ORR of 18% and DCR of 64%. Thus, the antibody-drug conjugate (1) was more effective than treatment with T-DM1.

One of the cases that achieved PR (partial response) had a score of IHC1+ at the time of enrollment (FIG. 8).

A great majority of the cases that achieved PR received the doses of 5.4 mg/kg or lager (FIGS. 8 and 9).

Part 2 study: Dose expansion study (conducted in Japan and the USA)

(1) Analysis of Test Subject

The number of test subjects in each cohort, and the dose of the antibody-drug conjugate (1) in part 2 study are as shown in Table 3. For all the cohorts, the antibody-drug conjugate (1) was administered once every 3 weeks.

TABLE 3

| | The number of test subjects | Dose | |
|---|---|---|---|
| Part 2a | 43/100 | 5.4 mg/kg<br>6.4 mg/kg | HER2-overexpressing breast cancer having history of treatment with T-DM1 |
| Part 2b | 41/40 | 5.4 mg/kg<br>6.4 mg/kg | HER2-overexpressing gastric cancer having history of treatment with trastuzumab |
| Part 2c | 10/20 | 6.4 mg/kg | HER2 low-expressing breast cancer |
| Part 2d | 25/20 | 6.4 mg/kg | HER2-expressing solid cancer except for breast cancer and gastric cancer |

(2) Efficacy (2-1)

Figure 10:
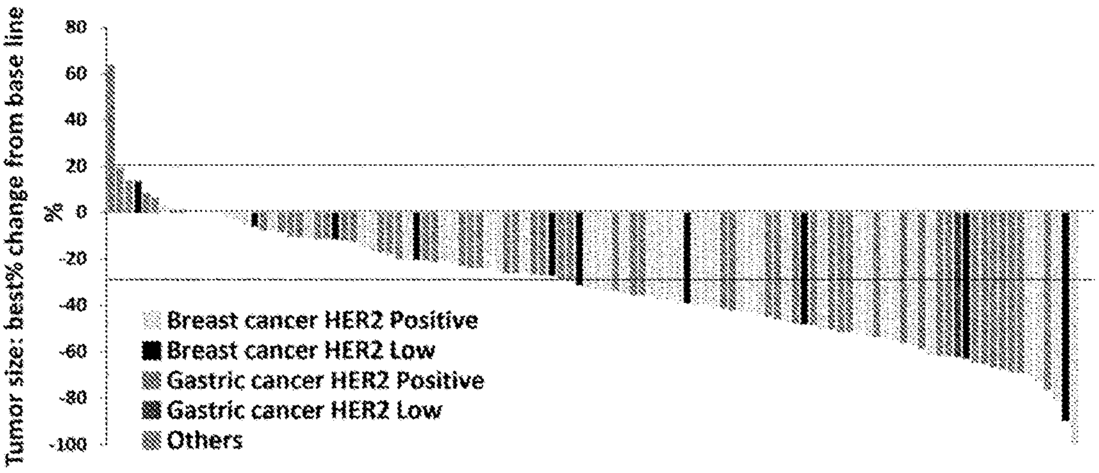
FIG. 10 is a diagram showing best % change from baseline in tumor size as to the efficacy of the antibody-drug conjugate (1) in a clinical study.

Best % change from baseline in tumor size is shown in FIG. 10 as to efficacy in the overall part 2 study. In the drawing, "Breast cancer HER2 Positive" represents a cohort of HER2-overexpressing breast cancer, "Breast cancer HER2 Low" represents a cohort of HER2 low-expressing breast cancer, "Gastric cancer HER2 Positive" represents a cohort of HER2-overexpressing gastric cancer, "Gastric cancer HER2 Low" represents a cohort of HER2 low-expressing gastric cancer, and "Others" represents HER2-expressing solid cancer except for breast cancer and gastric cancer. The antibody-drug conjugate (1) was found to exhibit an excellent tumor-shrinking effect on any type of cancer regardless of whether to HER2-overexpressing cancer or HER2 low-expressing cancer.

(2-2)

Time-dependent change in tumor shrinkage (%) is shown in

Figure 11:
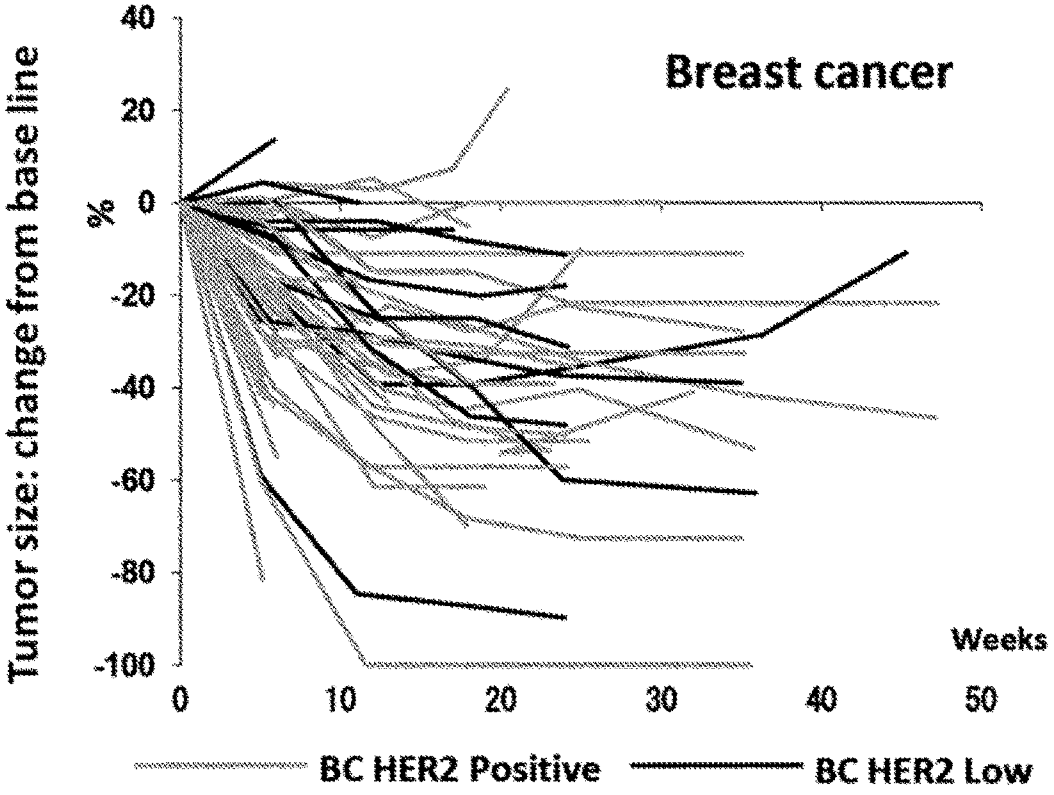
FIG. 11 is a diagram showing time-dependent change in tumor shrinkage (%) as to the efficacy of the antibody-drug conjugate (1) on breast cancer in a clinical study.
Figure 12:
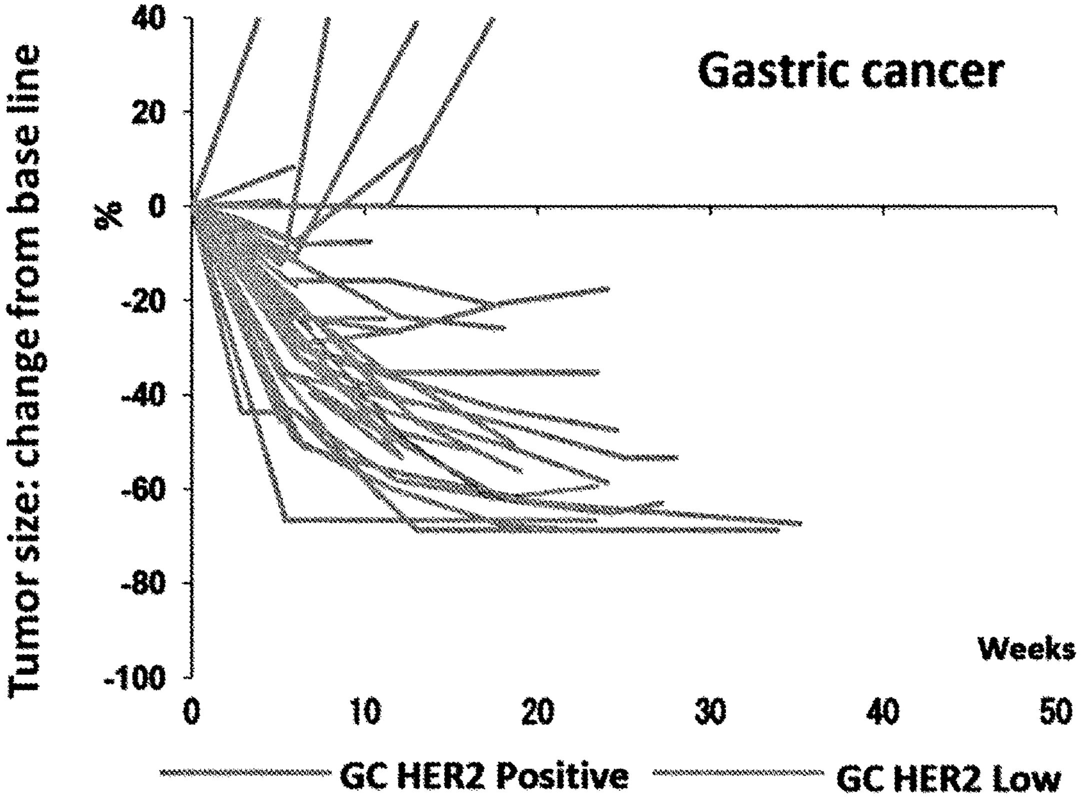
FIG. 12 is a diagram showing time-dependent change in tumor shrinkage (%) as to the efficacy of the antibody-drug conjugate (1) on gastric cancer in a clinical study.

FIG. 11 as to the efficacy of the antibody-drug conjugate (1) on breast cancer. In the drawing, "Breast cancer HER2 Positive" represents a cohort of HER2-overexpressing breast cancer, and "Breast cancer HER2 Low" represents a cohort of HER2 low-expressing breast cancer. Also, time-dependent change in tumor shrinkage (%) is shown in FIG.

12 as to the efficacy of the antibody-drug conjugate (1) on gastric cancer. In the drawing, "Gastric cancer HER2 Positive" represents a cohort of HER2-overexpressing gastric cancer, and "Gastric cancer HER2 Low" represents a cohort of HER2 low-expressing gastric cancer. The antibody-drug conjugate (1) was found to exhibit an excellent tumor shrinkage-maintaining effect on any type of cancer regardless of whether to HER2-overexpressing cancer or HER2 low-expressing cancer.

(2-3)

ORR (objective response rate) and DCR (disease control rate) are shown in Table 4 as to efficacy in the part 2 study. The antibody-drug conjugate (1) exhibited high ORR and DCR for all the cohorts. The antibody-drug conjugate (1) exhibited high ORR and DCR, particularly, for breast cancer patients having a history of treatment with trastuzumab emtansine (T-DM1), breast cancer patients having a history of treatment with combined use of trastuzumab emtansine and pertuzumab, and gastric cancer patients having a history of treatment with irinotecan (CPT-11).

TABLE 4

| | ORR (the number of test subjects) | DCR (the number of test subjects) |
|---|---|---|
| Overall | 40.2% (39/97) | 91.8% (89/97) |
| Breast cancer | 42.2% (19/45) | 97.8% (44/45) |
| Breast cancer (having history of treatment with T-DM1) | 45.7% (16/35) | 100.0% (35/35) |
| Breast cancer (having history of treatment with T-DM1 + pertuzumab) | 46.7% (14/30) | 100.0% (30/30) |
| Gastric cancer | 44.4% (16/36) | 88.9% (32/36) |
| Gastric cancer (having history of treatment with CPT-11) | 44.4% (8/18) | 94.4% (17/18) |

(2-4)

The test subjects of the part 2d study (HER2-expressing solid cancer except for breast cancer and gastric cancer) included patients with colorectal cancer (11 subjects), non-small cell lung cancer (5 subjects), salivary gland cancer (4 subjects), Paget's disease (2 subjects), esophageal cancer (1 subject), and bile duct cancer (1 subject). ORR of 33% and DCR of 91% were achieved in 12 evaluable patients. Two out of the 5 colorectal cancer patients achieved PR. Two out of the 4 salivary gland cancer achieved PR.

(2-5)

The results of the part 2d study are shown in Table 5. The antibody-drug conjugate (1) achieved ORR of 31.8% and DCR of 81.8% for 22 evaluable patients in the overall part 2d study. Among them, ORR of 20.0% and DCR of 80.0% were achieved for the cohort of colorectal cancer. ORR of 20.0% and DCR of 60.0% were achieved for the cohort of non-small cell lung cancer. ORR of 75.0% and DCR of 100.0% were achieved for the cohort of salivary gland cancer. ORR of 33.3% and DCR of 100.0% were achieved for the cohort of other cancers (Paget's disease, esophageal cancer, and bile duct cancer).

TABLE 5

| | ORR (the number of test subjects) | DCR (the number of test subjects) |
|---|---|---|
| Overall part 2d test | 31.8% (7/22) | 81.8% (18/22) |
| Colorectal cancer | 20.0% (2/10) | 80.0% (8/10) |
| Non-small cell lung cancer | 20.0% (1/5) | 60.0% (3/5) |
| Salivary gland cancer | 75.0% (3/4) | 100.0% (4/4) |
| Others (Paget's disease, esophageal cancer, and bile duct cancer) | 33.3% (1/3) | 100.0% (3/3) |

Figure 13:
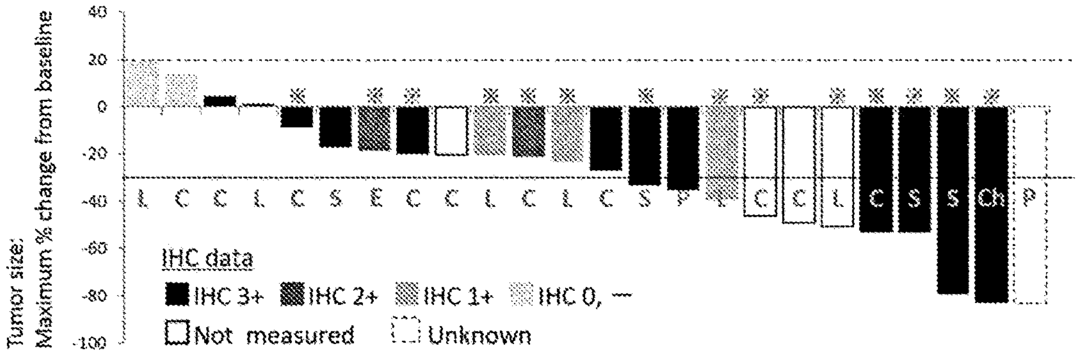
FIG. 13 is a diagram showing best % change from baseline in tumor size as to the efficacy of the antibody-drug conjugate (1) on HER2-expressing solid cancer (except for breast cancer and gastric cancer) in a clinical study. In the drawing, "C" represents a cohort of colorectal cancer, "L" represents a cohort of non-small cell lung cancer, "S" represents a cohort of salivary gland cancer, "P" represents a cohort of Paget's disease, "Ch" represents a cohort of bile duct cancer, and "E" represents a cohort of esophageal cancer. In the drawing, "*" shows that the treatment is ongoing.

Best % change from baseline in tumor size is shown in FIG. 13 as to the efficacy of the antibody-drug conjugate (1) in the part 2d study (in the drawing, "C" represents a cohort of colorectal cancer, "L" represents a cohort of non-small cell lung cancer, "S" represents a cohort of salivary gland cancer, "P" represents a cohort of Paget's disease, "Ch" represents a cohort of bile duct cancer, and "E" represents a cohort of esophageal cancer; in the drawing, "*" represents that the treatment is ongoing).

Figure 14:
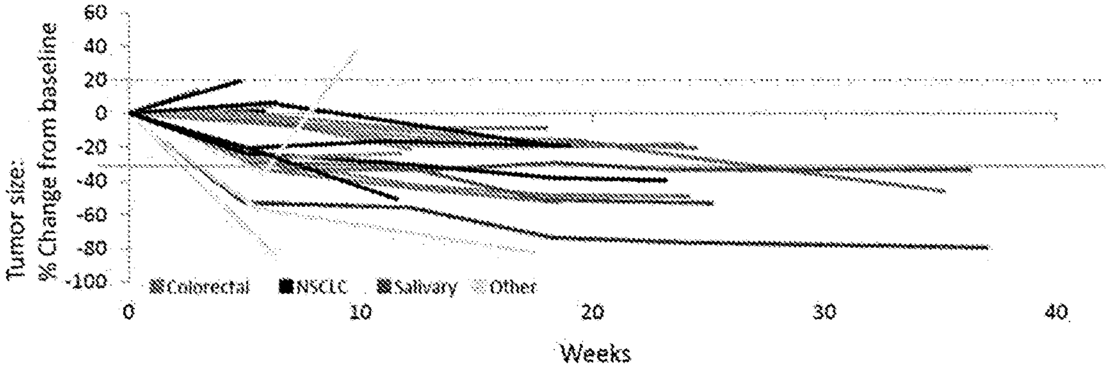
FIG. 14 is a diagram showing time-dependent change in tumor shrinkage (%) as to the efficacy of the antibody-drug conjugate (1) on HER2-expressing solid cancer (except for breast cancer and gastric cancer) in a clinical study. In the drawing, "Colorectal" represents a cohort of colorectal cancer, "NSCLC" represents a cohort of non-small cell lung cancer, "Salivary" represents a cohort of salivary gland cancer, and "Other" represents a cohort of other cancers.

Time-dependent change in tumor shrinkage (%) is further shown in FIG. 14 (in the drawing, "Colorectal" represents a cohort of colorectal cancer, "NSCLC" represents a cohort of non-small cell lung cancer, "Salivary" represents a cohort of salivary gland cancer, and "Other" represents a cohort of other cancers).

The antibody-drug conjugate (1) was found to exhibit an excellent tumor-shrinking effect on any type of cancer regardless of whether to HER2-overexpressing cancer or HER2 low-expressing cancer.

(3) Safety and Tolerability

The results about safety and tolerability are shown in Table 6. The most commonly observed adverse events (AEs) were gastrointestinal toxicity such as nausea, decreased appetite, and vomiting. Adverse events of grade 3 or higher were found to be few. Although myelosuppression such as platelet count decreased and neutrophil count decreased was also observed, adverse events of grade 3 or higher were also found to be few for these.

TABLE 6

| | Grade 1 (%) | Grade 2 (%) | Grade 3 (%) | Grade 4 (%) | All (%) |
|---|---|---|---|---|---|
| Platelet count decreased | 13.5 | 9.0 | 8.3 | 3.8 | 34.6 |
| Anemia | 3.0 | 12.0 | 14.3 | 1.5 | 30.8 |
| Neutrophil count decreased | 0.8 | 9.8 | 12.0 | 3.0 | 25.6 |
| White blood cell count decreased | 0.8 | 12.8 | 9.0 | 1.5 | 24.1 |
| Nausea | 51.9 | 13.5 | 1.5 | 0.0 | 66.9 |
| Decreased appetite | 33.8 | 20.3 | 3.8 | 0.0 | 57.9 |
| Vomiting | 31.6 | 3.8 | 1.5 | 0.0 | 36.8 |
| Diarrhoea | 19.5 | 5.3 | 0.8 | 0.0 | 25.6 |
| Constipation | 18.8 | 3.0 | 0.0 | 0.0 | 21.8 |
| Alopecia | 21.1 | 6.0 | 0.0 | 0.0 | 27.1 |
| Malaise | 18.0 | 4.5 | 0.8 | 0.0 | 24.1 |

CONCLUSION

The antibody-drug conjugate (1) exhibited high tolerability in the part 1 study (dose escalation study) without reaching MTD.

The antibody-drug conjugate (1) achieved ORR of 35% and DCR of 90% for 20 evaluable test subjects.

The antibody-drug conjugate (1) exhibited a higher response rate for breast cancer patients previously treated with T-DM1 than that of T-DM1 in prior treatment.

In the part 2 study (dose expansion study), the antibody-drug conjugate (1) was administered once every 3 weeks at doses of 5.4 mg/kg and 6.4 mg/kg. The antibody-drug conjugate (1) was found to exhibit an excellent antitumor effect on any type of cancer regardless of whether to HER2-overexpressing cancer or HER2 low-expressing cancer. Adverse events of grade 3 or higher were confirmed to be few, demonstrating that the antibody-drug conjugate (1) exhibits favorable safety profile.

These results demonstrated that the antibody-drug conjugate (1) has an excellent anticancer effect even on cancer that has acquired resistance by prior treatment with an anticancer drug. Examples of such prior treatment can include anti-HER2 therapy (treatment with an existing anti-HER2 drug, or treatment with a combination of an existing anti-HER2 drug and any of other anticancer drugs, etc.). Examples of the anti-HER2 therapy can include administration of an antibody such as trastuzumab or pertuzumab, and administration of an anti-HER2 antibody-drug conjugate T-DM1. For the anti-HER2 drug used in such prior treatment, cancer as a treatment subject must be confirmed HER2-positive (i.e., HER2 overexpression) by examination before administration. Thus, the anti-HER2 drug is administered in the expectation of its effect on the cancer in terms of the mechanism of action under which the anti-HER2 drug becomes effective by recognizing HER2. However, the anti-HER2 drug, when continuously administered, is confirmed to temporarily have an anticancer effect as expected, but observed to lead to a pathological condition in which its anticancer effect is no longer confirmed due to some mechanism. Under such a situation, the antibody-drug conjugate (1) used in the present invention was confirmed to have an excellent anticancer effect even on cancer for which the administration of an anti-HER2 drug in prior treatment is no longer effective. Specifically, the antibody-drug conjugate (1) was confirmed to exhibit an excellent anticancer effect even on cancer that acquired resistance (secondary resistant cancer) by the administration of an existing anti-HER2 drug in prior treatment.

Moreover, the clinical studies demonstrated that the antibody-drug conjugate (1) also exhibits an excellent therapeutic effect on HER2 low-expressing cancer or solid cancer other than breast cancer and gastric cancer (e.g., colorectal cancer, non-small cell lung cancer, salivary gland cancer, Paget's disease, esophageal cancer, and bile duct cancer). These cancers are cancers, albeit expressing HER2, on which the therapeutic effect of an existing anti-HER2 drug is originally not confirmed (in other words, HER2-expressing cancer having resistance or refractoriness intrinsic to the cancer to an existing anti-HER2 drug independently of treatment with the existing anti-HER2 drug).

These results demonstrated that the therapeutic agent and the pharmaceutical composition for treatment comprising the antibody-drug conjugate used in the present invention, and the treatment method comprising administering the antibody-drug conjugate of the present invention are excellent in the treatment of HER2-expressing cancer having resistance or refractoriness to an existing anti-HER2 drug.

Free Text of Sequence Listing

SEQ ID NO: 1—Amino acid sequence of a heavy chain of the humanized anti-HER2 monoclonal antibody SEQ ID NO: 2—Amino acid sequence of a light chain of the humanized anti-HER2 monoclonal antibody

The invention claimed is:

1. A method for treating HER2-expressing cancer having resistance to an existing anti-HER2 drug, comprising administering a dose per administration of a range of 5.4 mg/kg to 6.4 mg/kg of an antibody-drug conjugate in which a linker and a drug represented by the following formula are conjugated to an anti-HER2 antibody to a human patient in need of the treatment of the HER2-expressing cancer having resistance to an existing anti-HER2 drug:

-(Succinimid-3-yl-N)—$CH_2CH_2CH_2CH_2CH_2$—C(═O)-GGFG (SEQ ID NO: 5)-NH—$CH_2$—O—$CH_2$—C(═O)—(NH-DX)

wherein (Succinimid-3-yl-N)- has a structure represented by the following formula:

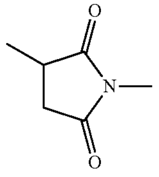

which is connected to the anti-HER2 antibody at position 3 thereof via a thioether bond and is connected to the methylene group in the linker structure containing this structure on the nitrogen atom at position 1, (NH-DX) represents a group represented by the following formula:

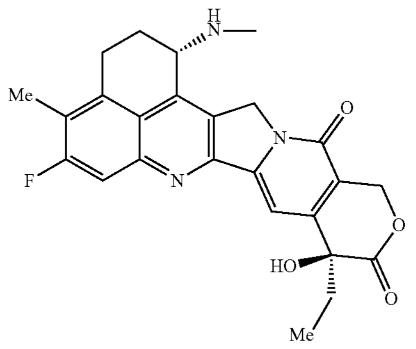 [SMILES: CC[C@@]1(O)C(=O)OCc2c1cc1n(c2=O)Cc2c-1nc1cc(F)c(C)c3c1c2[C@@H](NC)CC3]

wherein the nitrogen atom of the amino group at position 1 is the connecting position, and -GGFG- represents the tetrapeptide residue of -Gly-Gly-Phe-Gly- (SEQ ID NO: 5);

wherein the anti-HER2 antibody comprises (i) a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2; or (ii) a heavy chain consisting of the amino acid sequence represented by SEQ ID NO: 1 and a light chain consisting of the amino acid sequence represented by SEQ ID NO: 2.

2. The method according to claim 1, wherein the existing anti-HER2 drug is at least one selected from the group consisting of trastuzumab emtansine, trastuzumab, pertuzumab, and lapatinib.

3. The method according to claim 1, wherein the existing anti-HER2 drug is trastuzumab emtansine.

4. The method according to claim 1, wherein the existing anti-HER2 drug is trastuzumab.

5. The method according to claim 1, wherein the human patient has a history of treatment with an existing anticancer drug.

6. The method according to claim 5, wherein the existing anticancer drug comprises trastuzumab emtansine.

7. The method according to claim 5, wherein the existing anticancer drug comprises trastuzumab.

8. The method according to claim 5, wherein the existing anticancer drug comprises irinotecan.

9. The method according to claim 1, wherein an average number of units of the drug-linker structure conjugated per antibody molecule of the antibody-drug conjugate is in a range of 7 to 8.

10. The method according to claim 1, wherein an average number of units of the drug-linker structure conjugated per antibody molecule of the antibody-drug conjugate is in a range of 7.5 to 8.

11. The method according to claim 1, wherein the anti-HER2 antibody comprises a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

12. The method according to claim 1, wherein the anti-HER2 antibody comprises a heavy chain consisting of the amino acid sequence represented by SEQ ID NO: 1 and a light chain consisting of the amino acid sequence represented by SEQ ID NO: 2.

13. The method according to claim 1, wherein the antibody-drug conjugate is administered once every 3 weeks.

14. The method according to claim 1, wherein the cancer is at least one selected from the group consisting of breast cancer, gastric cancer, colorectal cancer, esophageal cancer, salivary gland cancer, pancreatic cancer, ovarian cancer, uterine cancer, lung cancer, and sarcoma.

15. The method according to claim 1, wherein the cancer is breast cancer.

16. The method according to claim 1, wherein the cancer is gastric cancer.

17. The method according to claim 1, wherein the cancer is colorectal cancer.

18. The method according to claim 1, wherein the cancer is salivary gland cancer.

19. The method according to claim 1, wherein the HER2-expressing cancer is HER2-overexpressing cancer.

20. The method according to claim 1, wherein the antibody-drug conjugate is administered together with a pharmaceutically acceptable formulation component.

21. The method according to claim 1, wherein the resistance is acquired by the cancer due to treatment with the existing anti-HER2 drug.

22. The method according to claim 1, wherein the dose per administration of the antibody-drug conjugate is 5.4 mg/kg.

23. The method according to claim 1, wherein the dose per administration of the antibody-drug conjugate is 6.4 mg/kg.

24. The method according to claim 9, wherein the anti-HER2 antibody comprises a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

25. The method according to claim 9, wherein the anti-HER2 antibody comprises a heavy chain consisting of the amino acid sequence represented by SEQ ID NO: 1 and a light chain consisting of the amino acid sequence represented by SEQ ID NO: 2.

26. The method according to claim 10, wherein the anti-HER2 antibody comprises a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

27. The method according to claim 10, wherein the anti-HER2 antibody comprises a heavy chain consisting of the amino acid sequence represented by SEQ ID NO: 1 and a light chain consisting of the amino acid sequence represented by SEQ ID NO: 2.

28. A method for treating HER2-expressing cancer having resistance to an existing anti-HER2 drug, comprising administering a dose per administration of a range of 5.4 mg/kg to 6.4 mg/kg of an antibody-drug conjugate represented by the following Formula

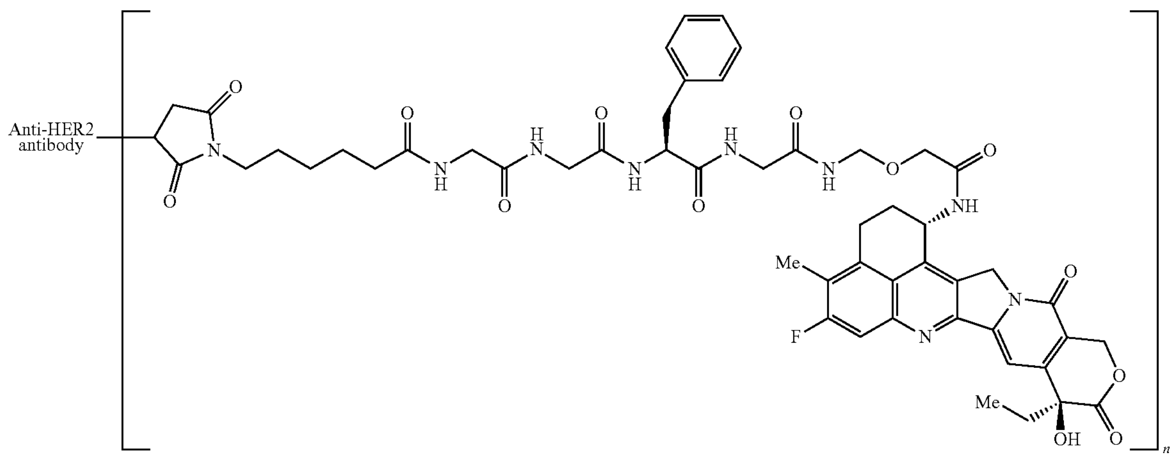

to a human patient in need of the treatment of the HER2-expressing cancer having resistance to an existing anti-HER2 drug;

wherein in the Formula, a drug-linker is conjugated to the anti-HER2 antibody via a thioether bond, and n represents an average number of units of the drug-linker structure conjugated per antibody molecule of the antibody-drug conjugate;

wherein the average number of units of the drug-linker structure conjugated per antibody molecule of the antibody-drug conjugate is 7 to 8;

wherein the anti-HER2 antibody comprises (i) a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2; or (ii) a heavy chain consisting of the amino acid sequence represented by SEQ ID NO: 1 and a light chain consisting of the amino acid sequence represented by SEQ ID NO: 2;

wherein the antibody-drug conjugate is administered once every 3 weeks; and wherein the cancer is at least one selected from the group consisting of breast cancer, gastric cancer, colorectal cancer, esophageal cancer, salivary gland cancer, pancreatic cancer, ovarian cancer, uterine cancer, lung cancer, and sarcoma.

29. The method according to claim 1, wherein an average number of units of the drug-linker structure conjugated per antibody molecule of the antibody-drug conjugate is in a range of 7 to 8; and wherein the dose per administration of the antibody-drug conjugate is 5.4 mg/kg.

30. The method according to claim 1, wherein an average number of units of the drug-linker structure conjugated per antibody molecule of the antibody-drug conjugate is in a range of 7 to 8; and wherein the dose per administration of the antibody-drug conjugate is 6.4 mg/kg.

31. The method according to claim 1, wherein an average number of units of the drug-linker structure conjugated per antibody molecule of the antibody-drug conjugate is in a range of 7.5 to 8; and wherein the dose per administration of the antibody-drug conjugate is 5.4 mg/kg.

32. The method according to claim 1, wherein an average number of units of the drug-linker structure conjugated per antibody molecule of the antibody-drug conjugate is in a range of 7.5 to 8; and wherein the dose per administration of the antibody-drug conjugate is 6.4 mg/kg.

* * * * *

```
                          SEQUENCE LISTING


<160> NUMBER OF SEQ ID NOS: 14

<210> SEQ ID NO 1
<211> LENGTH: 450
<212> TYPE: PRT
<213> ORGANISM: Artificial Sequence
<220> FEATURE:
<223> OTHER INFORMATION: amino acid sequence of the heavy chain of
      Trastuzumab

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125
```

-continued

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 2
<211> LENGTH: 214
<212> TYPE: PRT
<213> ORGANISM: Artificial Sequence
<220> FEATURE:
<223> OTHER INFORMATION: amino acid sequence of the light chain of
      Trastuzumab

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30
```

-continued

```
Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 3
<211> LENGTH: 4
<212> TYPE: PRT
<213> ORGANISM: Artificial Sequence
<220> FEATURE:
<223> OTHER INFORMATION: Amino acid sequence of Lp

<400> SEQUENCE: 3

Asp Gly Gly Phe
1


<210> SEQ ID NO 4
<211> LENGTH: 4
<212> TYPE: PRT
<213> ORGANISM: Artificial Sequence
<220> FEATURE:
<223> OTHER INFORMATION: Amino acid sequence of Lp

<400> SEQUENCE: 4

Glu Gly Gly Phe
1


<210> SEQ ID NO 5
<211> LENGTH: 4
<212> TYPE: PRT
<213> ORGANISM: Artificial Sequence
<220> FEATURE:
<223> OTHER INFORMATION: Amino acid sequence of Lp

<400> SEQUENCE: 5

Gly Gly Phe Gly
1


<210> SEQ ID NO 6
<211> LENGTH: 4
```

<212> TYPE: PRT
<213> ORGANISM: Artificial Sequence
<220> FEATURE:
<223> OTHER INFORMATION: Amino acid sequence of Lp

<400> SEQUENCE: 6

Ser Gly Gly Phe
1

<210> SEQ ID NO 7
<211> LENGTH: 4
<212> TYPE: PRT
<213> ORGANISM: Artificial Sequence
<220> FEATURE:
<223> OTHER INFORMATION: Amino acid sequence of Lp

<400> SEQUENCE: 7

Lys Gly Gly Phe
1

<210> SEQ ID NO 8
<211> LENGTH: 5
<212> TYPE: PRT
<213> ORGANISM: Artificial Sequence
<220> FEATURE:
<223> OTHER INFORMATION: Amino acid sequence of Lp

<400> SEQUENCE: 8

Asp Gly Gly Phe Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Amino acid sequence of Lp

<400> SEQUENCE: 9

Gly Gly Phe Gly Gly
1               5

<210> SEQ ID NO 10
<211> LENGTH: 6
<212> TYPE: PRT
<213> ORGANISM: Artificial Sequence
<220> FEATURE:
<223> OTHER INFORMATION: Amino acid sequence of Lp

<400> SEQUENCE: 10

Asp Asp Gly Gly Phe Gly
1               5

<210> SEQ ID NO 11
<211> LENGTH: 6
<212> TYPE: PRT
<213> ORGANISM: Artificial Sequence
<220> FEATURE:
<223> OTHER INFORMATION: Amino acid sequence of Lp

<400> SEQUENCE: 11

Lys Asp Gly Gly Phe Gly
1               5

<210> SEQ ID NO 12
<211> LENGTH: 7
<212> TYPE: PRT

-continued

```
<213> ORGANISM: Artificial Sequence
<220> FEATURE:
<223> OTHER INFORMATION: Amino acid sequence of Lp

<400> SEQUENCE: 12

Gly Gly Phe Gly Gly Gly Phe
1               5


<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 13

His His His His His His
1               5


<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Phe Ala
1
```